(12) United States Patent
Abreu

(10) Patent No.: US 10,383,573 B2
(45) Date of Patent: Aug. 20, 2019

(54) APPARATUS CONFIGURED TO SUPPORT A DEVICE ON A HEAD

(71) Applicant: GEELUX HOLDINGS, LTD., Tortola (VG)

(72) Inventor: Marcio Marc Abreu, Bridgeport, CT (US)

(73) Assignee: Geelux Holdings, Ltd., Tortola (VG)

( * ) Notice: Subject to any disclaimer, the term of this patent is extended or adjusted under 35 U.S.C. 154(b) by 612 days.

(21) Appl. No.: 15/087,605

(22) Filed: Mar. 31, 2016

(65) Prior Publication Data

US 2016/0287173 A1    Oct. 6, 2016

Related U.S. Application Data

(60) Provisional application No. 62/141,001, filed on Mar. 31, 2015.

(51) Int. Cl.

| A61B 5/00 | (2006.01) |
| G02C 11/00 | (2006.01) |
| A61B 5/01 | (2006.01) |
| A61B 5/0476 | (2006.01) |
| A61B 5/145 | (2006.01) |
| A61B 5/1455 | (2006.01) |

(52) U.S. Cl.
CPC .......... *A61B 5/6803* (2013.01); *A61B 5/4821* (2013.01); *G02C 11/10* (2013.01); *A61B 5/0006* (2013.01); *A61B 5/01* (2013.01); *A61B 5/0476* (2013.01); *A61B 5/1455* (2013.01); *A61B 5/14532* (2013.01); *A61B 2560/0266* (2013.01); *A61B 2560/0425* (2013.01)

(58) Field of Classification Search
USPC .......... 381/380, 381, 370; 351/155, 47, 114, 351/153, 106, 110; 2/11, 181.8, 205, 452
See application file for complete search history.

(56) References Cited

U.S. PATENT DOCUMENTS

| 4,784,149 | A | 11/1988 | Berman et al. | |
| 5,617,477 | A * | 4/1997 | Boyden | H04R 3/12 381/309 |
| 5,673,692 | A | 10/1997 | Schulze et al. | |
| 5,752,280 | A * | 5/1998 | Hill | A42B 3/185 2/453 |
| 5,984,874 | A | 11/1999 | Cerwin | |
| 6,292,685 | B1 | 9/2001 | Pompei | |
| 8,721,562 | B2 | 5/2014 | Abreu | |
| 2003/0179157 | A1 * | 9/2003 | Stanton | G02B 27/017 345/8 |
| 2012/0316459 | A1 * | 12/2012 | Abreu | A61B 5/0002 600/549 |

(Continued)

OTHER PUBLICATIONS

Notification of Transmittal of the International Search Report and the Written Opinion of the International Searching Authority; PCT/US2016/025313 dated Jul. 12, 2016.

(Continued)

*Primary Examiner* — Curtis A Kuntz
*Assistant Examiner* — Julie X Dang
(74) *Attorney, Agent, or Firm* — Studebaker & Brackett PC

(57) ABSTRACT

The described apparatuses can include support by at least a portion of a forehead in combination with at least one of a nose, an ear, and a head, or present an adjustable apparatus to provide improved fit of a head-positioned apparatus.

13 Claims, 125 Drawing Sheets

(56) References Cited

U.S. PATENT DOCUMENTS

| | | | |
|---|---|---|---|
| 2013/0124039 A1 | 5/2013 | Abreu | |
| 2013/0258270 A1* | 10/2013 | Cazalet | G02C 11/10 |
| | | | 351/114 |
| 2013/0258271 A1* | 10/2013 | Cazalet | G02C 5/16 |
| | | | 351/155 |
| 2014/0342338 A1 | 11/2014 | Imran et al. | |
| 2015/0216479 A1 | 8/2015 | Abreu | |
| 2016/0270726 A1 | 9/2016 | Abreu | |

OTHER PUBLICATIONS

A Rejection Decision issued by the Brazilian Patent Office dated Aug. 17, 2016, which corresponds to Brazilian Patent Application No. 122016006774-2 and is related to U.S. Appl. No. 15/087,605, with partial English language translation.

International Search Report dated Jul. 12, 2016 in corresponding PCT Application No. PCT/US2016/025313 (3 pp).

Written Opinion dated Jul. 12, 2016 in corresponding PCT Application No. PCT/US2016/025313 (4 pp).

\* cited by examiner

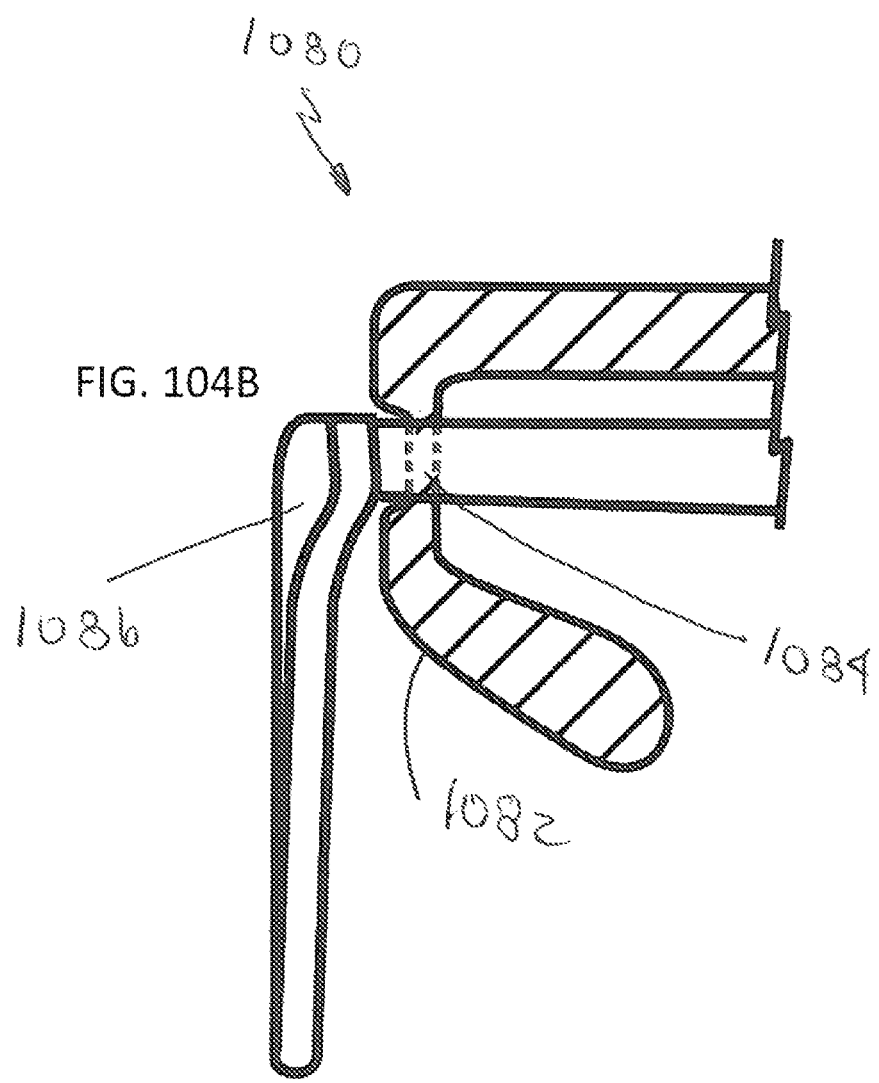

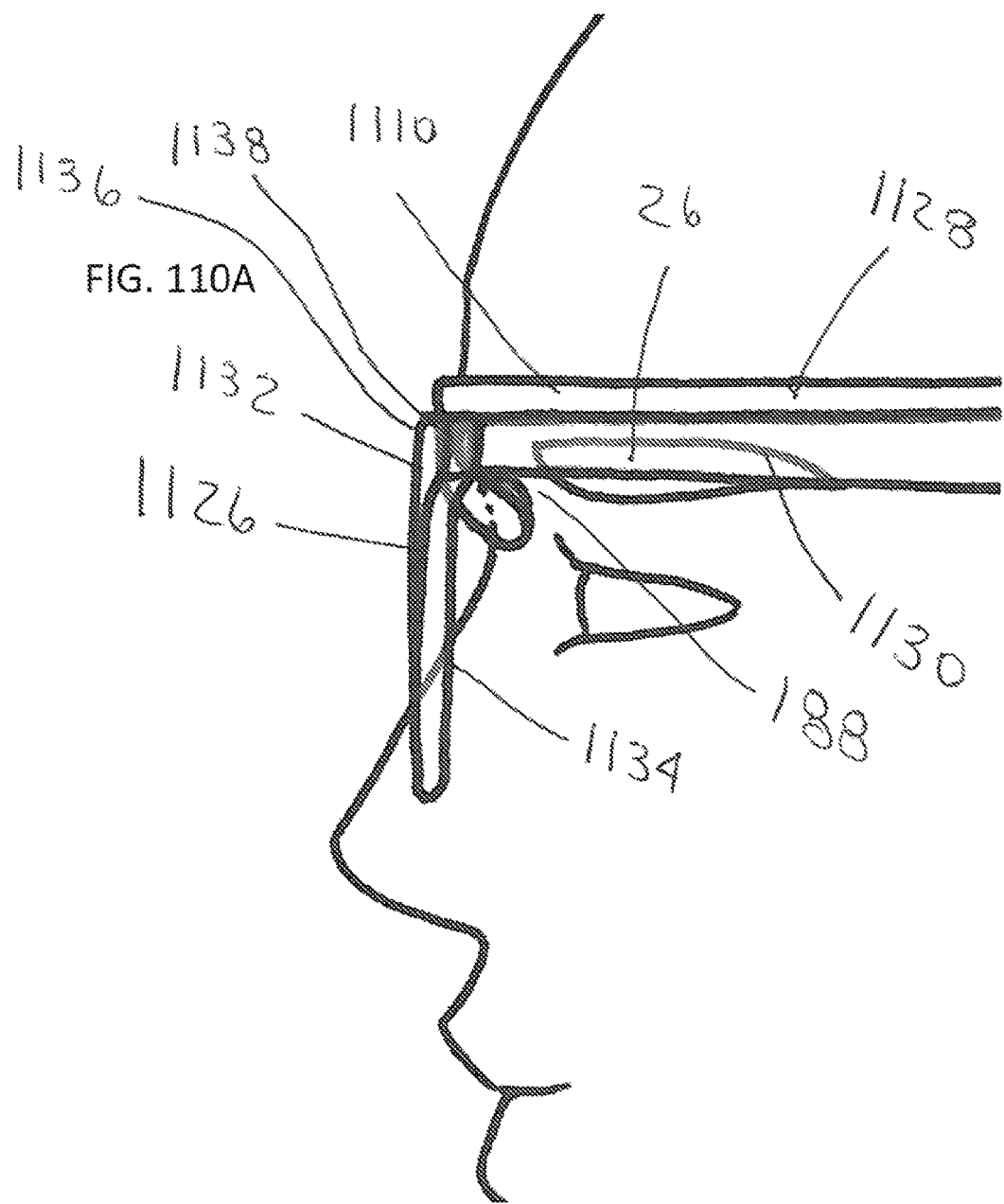

APPARATUS CONFIGURED TO SUPPORT A DEVICE ON A HEAD

CROSS-REFERENCE TO RELATED APPLICATIONS

This application claims the benefit of priority to U.S. Provisional Patent Application No. 62/141,001, filed on Mar. 31, 2015, which is hereby incorporated by reference in its entirety.

TECHNICAL FIELD

This disclosure relates to apparatuses configured to support at least one device on a human head.

BACKGROUND

Many devices are configured to interface with a human head, including prescription eyeglasses, sunglasses, headphones, earbuds, etc. These devices include a conventional supporting mechanism that interfaces with one or more portions of the human head, such as a nose and an ear.

SUMMARY

This disclosure provides an apparatus supported by a human head, comprising a first end, a second end, a connecting portion, and at least one device supported on the apparatus. The first end is configured to be supported on the head adjacent to a first ear. The second end is configured to be supported on the head adjacent to a second ear. The connecting portion extends from the first end to the second end, and the connecting portion is configured to grip at least temples of the head to support the connecting portion on a forehead of the head at a location above a pair of eyebrows.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 104B shows a view of a seventy-second apparatus in accordance with an exemplary embodiment of the present disclosure.

FIG. 110A shows a further view of the seventy-sixth apparatus of FIG. 109.

FIG. 113 shows a cross-sectional view of the seventy-eighth apparatus of FIG. 112 along the lines 113-113.

FIG. 114 shows a view of a user wearing the seventy-eighth apparatus of FIG. 112.

FIG. 115 shows a view of a seventy-ninth apparatus in accordance with an exemplary embodiment of the present disclosure.

FIG. 116 shows a view of an eightieth apparatus in accordance with an exemplary embodiment of the present disclosure.

FIG. 117 shows a view of an eighty-first apparatus in accordance with an exemplary embodiment of the present disclosure.

FIG. 118 shows a view a user wearing the eighty-first apparatus of FIG. 117.

DETAILED DESCRIPTION

Figure 1:
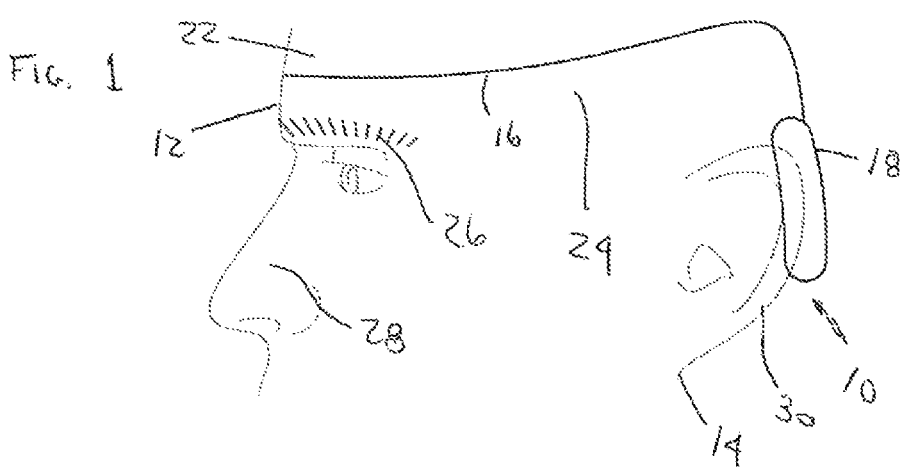
FIG. 1 shows a side view of a first apparatus in accordance with an exemplary embodiment of the present disclosure.

Conventional apparatuses to position devices on a head include eyeglasses, which further include monocles, sunglasses, over-the-ear devices, in-the-ear devices, headphones, and the like. These conventional devices are configured to be supported by an ear, a nose, a portion of an ocular cavity (monocles are so supported), or a combination of the ear and nose. Conventionally, headbands and hats use a head as a support, without the support of ears and a nose. In contrast to conventional apparatuses, the apparatuses of the present disclosure can include support by at least a portion of a forehead in combination with at least one of a nose, an ear, and a head, or present an adjustable apparatus to provide improved fit of a head-positioned apparatus.

In general it is not possible to wear conventional eyewear on top of another conventional eyewear. Moreover, in general it is not possible to wear conventional eyeglasses on top of sensing eyewear because the sensing eyewear has a sensor that needs to be in contact with skin or adjacent to the skin of the user. Applicant has disclosed a variety of sensing eyewear in previous disclosures, which uses essentially conventional frames. Applicant is a medical doctor, and when using his sensing eyewear in patients Applicant recognized that it was difficult if not impossible for patients to wear their conventional eyewear. Applicant then started to study and invent new frames of eyewear that can be used underneath or over conventional eyewear, including use with sensing eyewear and including the new eyewear frames of the present disclosure having sensors. Accordingly, the present disclosure describes new sensing eyewear that can be used jointly with conventional eyewear.

The new eyewear has a specialized configuration that includes specialized dimensions including the upper portion of the lens rim being located above the eyebrow, in contrast to conventional rims that are located either below the eyebrow or in few occasion on top of the eyebrow, but not on the forehead, as it is in the present disclosure. The present disclosure also describes new eyewear and new frames in which the frontal portion, or the upper lens rim and temples are made of thin wire or thin plastic (containing wires) and all hardware is located at the end of the temples, allowing thereby the eyewear of the present disclosure to be less noticeable, more functional, and cosmetically attractive since there would another frame on the face (conventional eyewear). Hence, the present disclosure allows two eyewear frames to be worn, but with the appearance of only one eyewear being used, since the sensing eyewear fades in the background. The sensing eyewear of the present disclosure preferably does not have lenses, but it should be understood that frames of the present disclosure includes lenses and/or contain anchoring means for lenses. The eyewear of the present disclosure can be worn alone or jointly with conventional eyewear and also underneath conventional eye wear. The frames of the present disclosure are adapted to be worn preferably underneath conventional eyewear.

In this manner a user can wear his/her conventional eyewear or prescription eyewear and still benefit from sensing eyewear functions, with the sensing eyewear being preferably positioned against the skin or adjacent to the skin. The method includes the step of positioning sensing eyewear on the face, adjusting the sensor on or adjacent to the ABTT terminus, and positioning conventional eyewear on top of the sensing eyewear. The sensing eyewear frame (also referred to herein as sensing frames) of the present disclosure has specialized weight distribution that includes minimal weight and thin frames on the front portion (right and left lens rim area) and in the temple portion (right and left temples) and heavy weight and thick frames containing hardware in the distal portion of the temples around the ear and in the end of the temples.

The upper portion of the ear is generally aligned with the eyebrow, and those two structures, eyebrow and ear, are used as anatomic landmarks for the specialized dimensions of the sensing frame of the present disclosure. Distance X indicates the distance from the eyebrow to the area where an upper frame is positioned on the forehead, which provides the dimension (height) of the upper portion of the frame of the present disclosure. In the context of this disclosure, the term "upper frame" specifically refers to any wire or frame portion that extends along or across the forehead in the area above the eyebrows. In addition, the term "temple" is applied to any wire or frame portion that extends along the side of the head from the forehead. In conventional eyewear there is no difference between the height of frame over the ear and height of the upper frame over the forehead, because the frame essentially is straight from the temple to the upper portion of the frame and lens rim. In sharp contrast, the upper frame of the sensing eyewear of the present disclosure is above the eyebrow and above the upper frame of conventional eyewear. The frame of the sensing eyewear of the present disclosure has a vertical dimension of the lens rim portion that is bigger than lens rim of conventional eyewear. It should be apparent that apparatuses of the present disclosure are configured to be supported above nose and above eyebrow along forehead, and along temples above tip of the ear, until the support goes down behind the ear or adjacent to the ear, or alternatively behind the head. It should be apparent, from the drawings herein, the variations of the frame of the present disclosure to achieve the sensing function and/or be worn underneath conventional eyeglasses.

Figure 27:
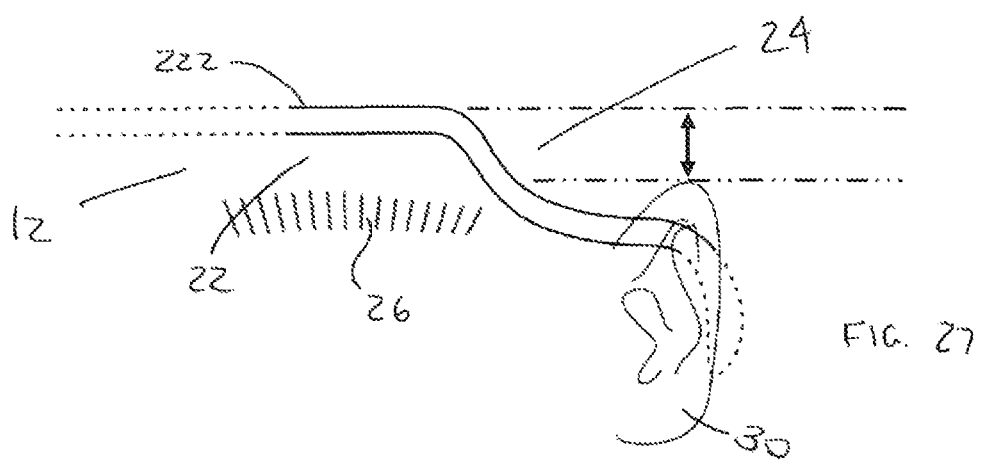
FIG. 27 shows another view of a position of an apparatus in accordance with an exemplary embodiment of the present disclosure.

Distance X is the distance from upper portion of the frame to the portion of the frame that is on top of tip of ear or aligned with the tip of the ear. Considering that the tip of the ear is essentially aligned with the eyebrow, distance X can also represent the distance from the middle of the eyebrow to the upper frame, or the vertical dimension from the middle of the eyebrow to the upper portion of the frame. Distance X can also be measured from the tip of the ear to the position of the upper frame as seen in FIG. 27. The preferred distance X is equal to or less than 35 mm, is more preferably equal to or less than 20 mm, is even more preferably equal to or less than 10 mm, and is most preferably equal to or less than 5 mm.

Many aspects of the disclosure and of the sensing frames of the present disclosure are described in terms of sequences of actions to be performed by elements of a computer system or other hardware capable of executing programmed instructions, for example, a general-purpose computer, special purpose computer, workstation, or other programmable data process apparatus. It should be recognized that in each of the embodiments, the various actions could be performed by specialized circuits (e.g., discrete logic gates interconnected to perform a specialized function), by program instructions (software), such as program modules, being executed by one or more processors (e.g., one or more microprocessors, a central processing unit (CPU), and/or application specific integrated circuit), or by a combination of both. For example, embodiments can be implemented in hardware, software, firmware, microcode, or any combination thereof. The instructions can be program code or code segments that perform necessary tasks and can be stored in a non-transitory machine-readable medium such as a storage medium or other storage(s). A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents.

The non-transitory machine-readable medium can additionally be considered to be embodied within any tangible form of computer readable carrier, such as solid-state memory, magnetic disk, and optical disk containing an appropriate set of computer instructions, such as program modules, and data structures that would cause a processor to carry out the techniques described herein. A computer-readable medium may include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (e.g., EPROM, EEPROM, or Flash memory), or any other tangible medium capable of storing information. It should be noted that the system of the present disclosure is illustrated and discussed herein as having various modules and units that perform particular functions.

It should be understood that these modules and units are merely described based on their function for clarity purposes, and do not necessarily represent specific hardware or software. In this regard, these modules, units and other components may be hardware and/or software implemented to substantially perform their particular functions explained herein. The various functions of the different components can be combined or segregated as hardware and/or software modules in any manner, and can be useful separately or in combination. Input/output or I/O devices or user interfaces including, but not limited to, keyboards, displays, pointing devices, and the like can be coupled to the system either directly or through intervening I/O controllers. Thus, the various aspects of the disclosure may be embodied in many different forms, and all such forms are contemplated to be within the scope of the disclosure.

Figure 2:
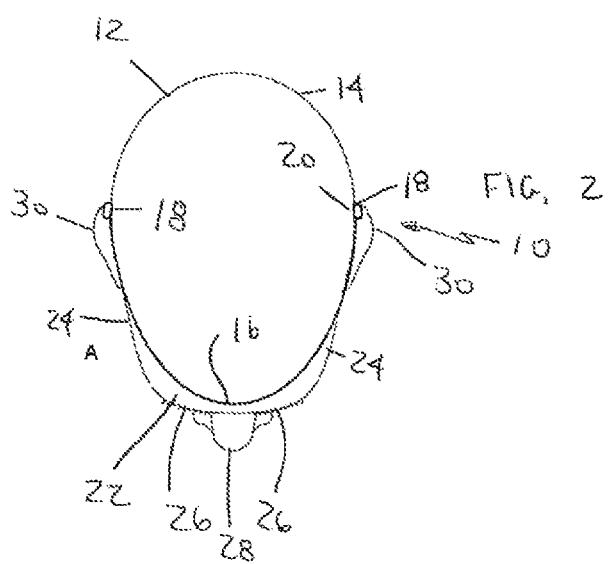
FIG. 2 shows a top view of the first apparatus of FIG. 1.
Figure 3:
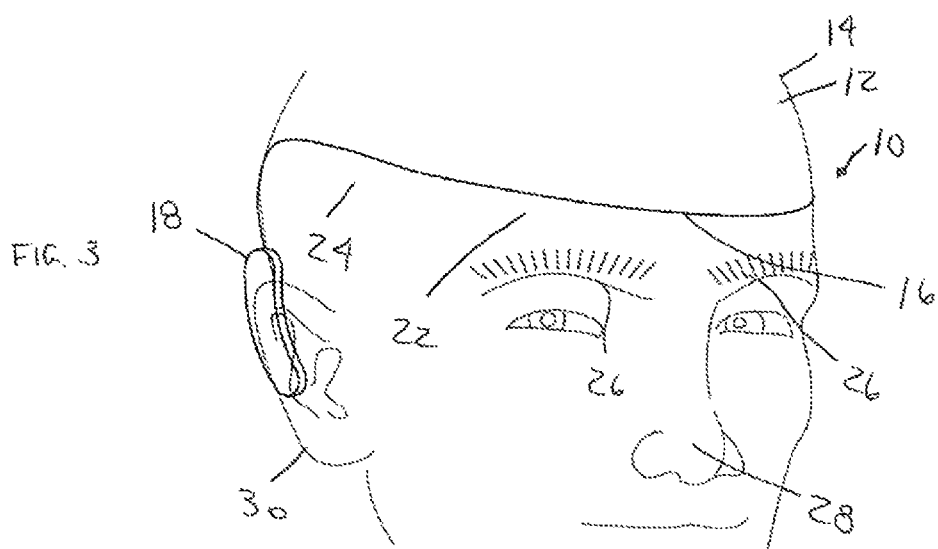
FIG. 3 shows a perspective view of the first apparatus of FIG. 1.

FIGS. 1-3 show a first apparatus in accordance with an exemplary embodiment of the present disclosure, indicated generally at 10. Apparatus 10 is configured to be positioned on a head 12 of a subject 14. Apparatus 10 is configured to include a curvilinear wire portion 16 and at least one device 18. Device 18 can be configured to include a frictional surface 20 to assist in holding apparatus 10 on head 12. Device 18 can be a speaker, a transmitter, or another device. It should be understand that when a plurality of devices are included in apparatus 10, or in any of the apparatuses presented herein, each device can provide a different function, independently. For example, one device can be configured to include a speaker, and the other device can be configured to include a transmitter. It should be understood that head 12 includes a plurality of features, including a forehead 22, temples 24, eyebrows 26, nose 28, and ear 30. Curvilinear wire portion 16 is configured to engage one or more portions of head 12 to support apparatus 10. In the exemplary embodiment of FIGS. 1-3, curvilinear wire portion 16 is configured to provide pressure against temples 24 of head 12, thus gripping or holding onto head 12. To provide such pressure, curvilinear wire portion 16 can be configured as a spring-like material that retains a predetermined shape unless curvilinear wire portion 16 is moved or stretched by the presence of an object or surface, such as temples 24.

Figure 4:
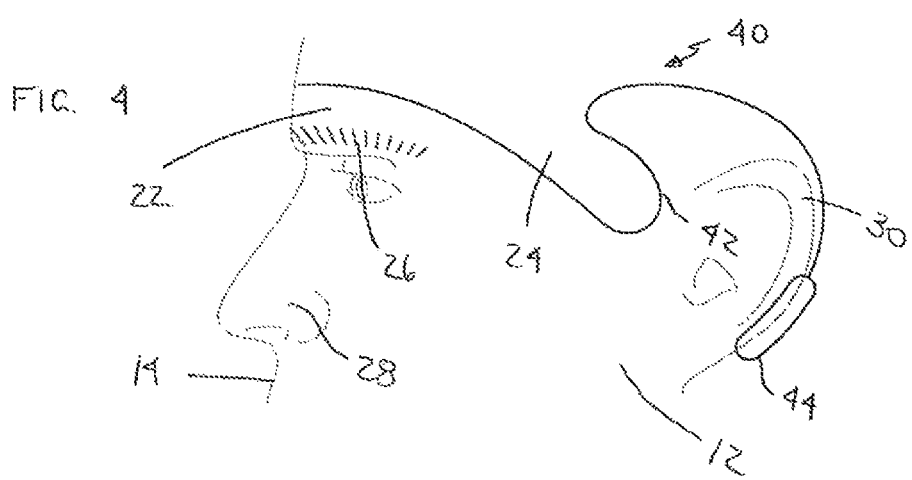
FIG. 4 shows a side view of a second apparatus in accordance with an exemplary embodiment of the present disclosure.
Figure 5:
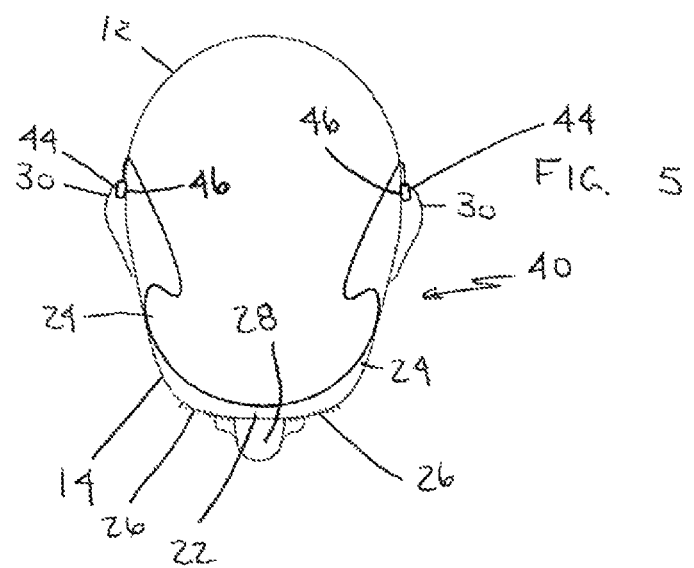
FIG. 5 shows a top view of the second apparatus of FIG. 4.
Figure 6:
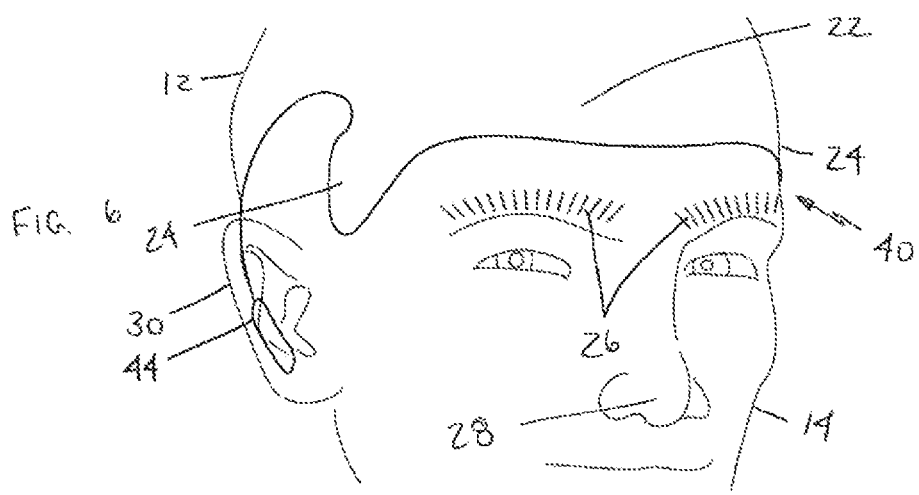
FIG. 6 shows a perspective view of the second apparatus of FIG. 4.

FIGS. 4-6 show a second apparatus in accordance with an exemplary embodiment of the present disclosure, indicated generally at 40. Apparatus 40 is configured to be positioned on head 12 of subject 14. Apparatus 40 is configured to include a curvilinear wire portion 42 and at least one device 44. Device 44 can be configured to include a frictional surface 46 to assist in holding apparatus 40 on head 12. Device 44 can be a speaker, a transmitter, or another device. Curvilinear wire portion 42 is configured to include a double loop that can also be described as an "S" curve or configuration on one side, and a mirrored or reverse "S" curve or configuration on an opposite side of head 12. The double loop portion of curvilinear wire portion 42 is configured to engage one or more portions of head 12 to support apparatus 40. In the exemplary embodiment of FIGS. 4-6, curvilinear wire portion 42 is configured to provide pressure against temples 24 of head 12, thus gripping or holding onto head 12. To provide such pressure, curvilinear wire portion 42 can be configured as a spring-like material that retains a predetermined shape unless curvilinear wire portion 42 is moved or stretched by the presence of an object or surface, such as temples 24.

Figure 7:
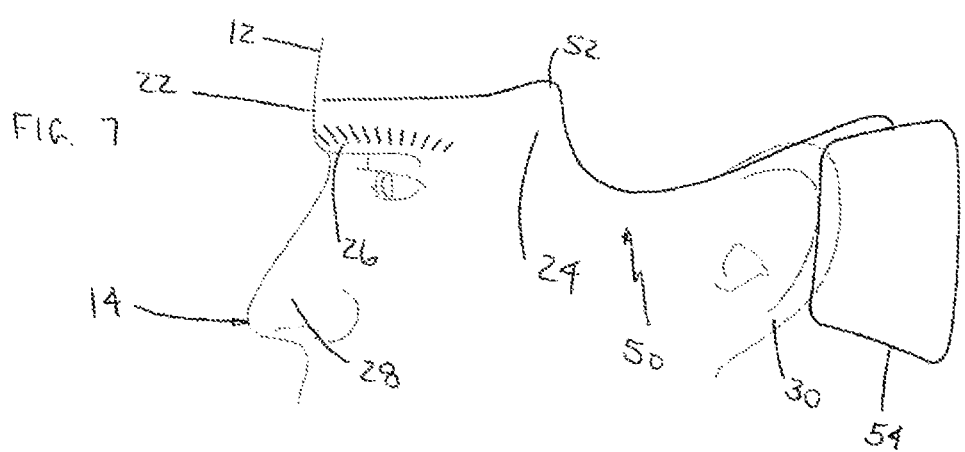
FIG. 7 shows a side view of a third apparatus in accordance with an exemplary embodiment of the present disclosure.
Figure 8:
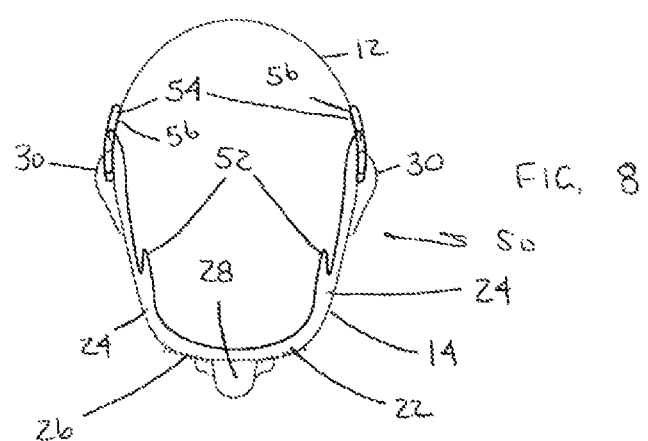
FIG. 8 shows a top view of the third apparatus of FIG. 7.
Figure 9:
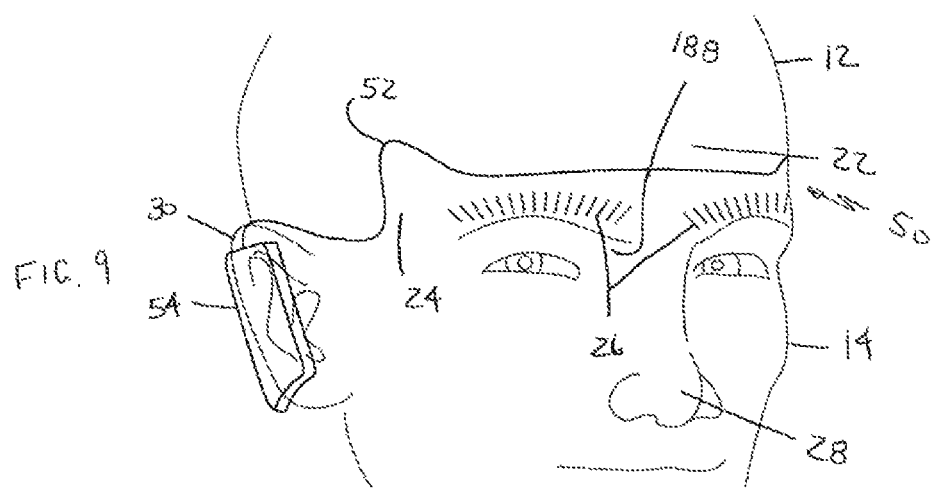
FIG. 9 shows a perspective view of the third apparatus of FIG. 7.

FIGS. 7-9 show a third apparatus in accordance with an exemplary embodiment of the present disclosure, indicated generally at 50. Apparatus 50 is configured to be positioned on head 12 of subject 14. Apparatus 50 is configured to include a curvilinear wire portion 52 and at least one device 54. Device 54 can be configured to include a frictional surface 56 to assist in holding apparatus 50 on head 12. Device 54 can be a speaker, a transmitter, or another device. Curvilinear wire portion 52 is configured to include a double curve on each side of head 12. The double curve portion of curvilinear wire portion 52 is configured to engage one or more portions of head 12 to support apparatus 50. In the exemplary embodiment of FIGS. 7-9, curvilinear wire portion 52 is configured to provide pressure against temples 24 of head 12, thus gripping or holding onto head 12. To provide such pressure, curvilinear wire portion 52 can be configured as a spring-like material that retains a predetermined shape unless curvilinear wire portion 52 is moved or stretched by the presence of an object or surface, such as temples 24.

Figure 10:
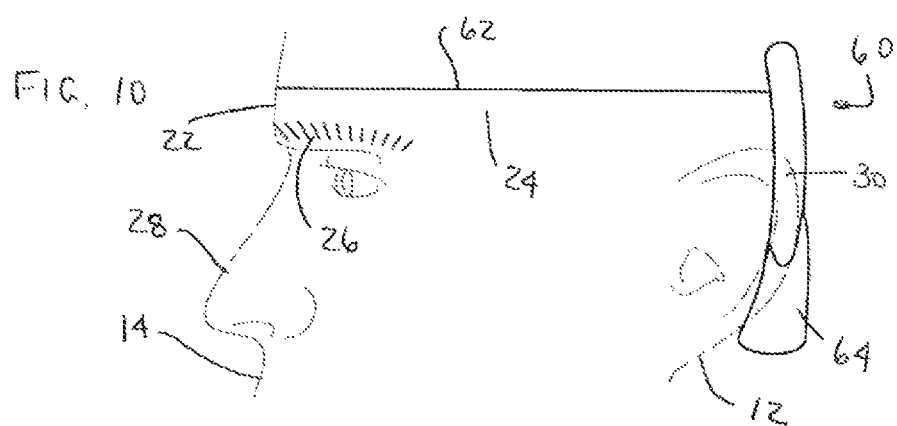
FIG. 10 shows a side view of a fourth apparatus in accordance with an exemplary embodiment of the present disclosure.
Figure 11:
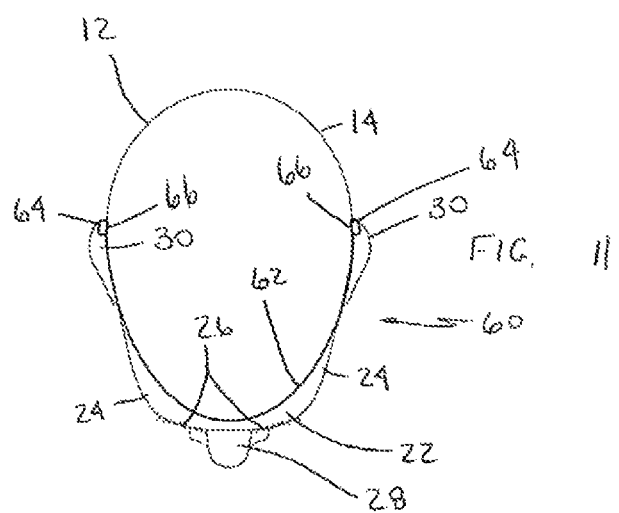
FIG. 11 shows a top view of the fourth apparatus of FIG. 10.
Figure 12:
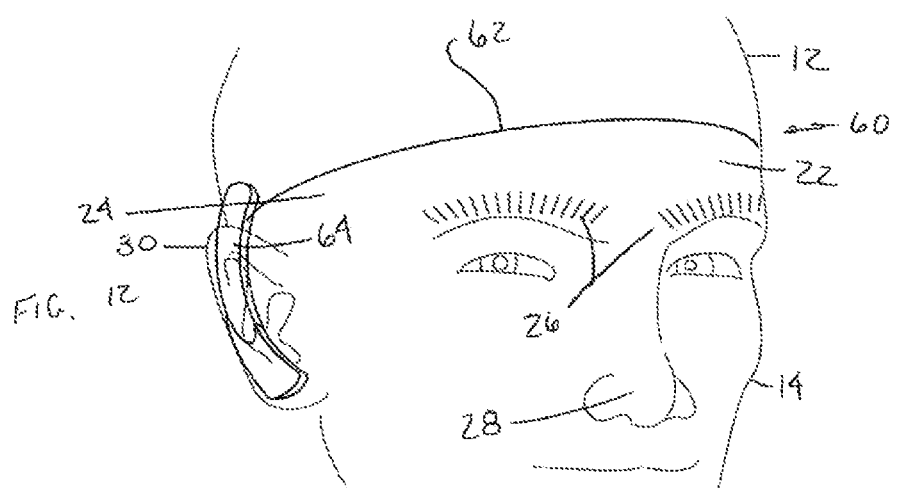
FIG. 12 shows a perspective view of the fourth apparatus of FIG. 10.

FIGS. 10-12 show a fourth apparatus in accordance with an exemplary embodiment of the present disclosure, indicated generally at 60. Apparatus 60 is configured to be positioned on head 12 of subject 14. Apparatus 60 is configured to include a wire portion 62 and at least one device 64. Device 64 can be configured to include a frictional surface 66 to assist in holding apparatus 60 on head 12. Device 64 can be a speaker, a transmitter, or another device. Wire portion 62 is configured as a substantially straight wire that extends from one side of head 12 to another side of head 12, connected to at least one device 64. In the exemplary embodiment of FIGS. 10-12, fourth apparatus 60 is configured to include two devices 64. In the context of this embodiment, substantially straight means generally flat or horizontal when viewing wire portion 62 from a side or front of head 12. Generally, flat or horizontal does not mean perfectly flat, but can include small curves or variations, though much less than the curves shown in the previous embodiments described herein. In the exemplary embodiment of FIGS. 10-12, wire portion 62 is configured to provide pressure against temples 24 of head 12, thus gripping or holding onto head 12. To provide such pressure, wire portion 62 can be configured as a spring-like material that retains a predetermined shape unless wire portion 62 is moved or stretched by the presence of an object or surface, such as temples 24.

Figure 13:
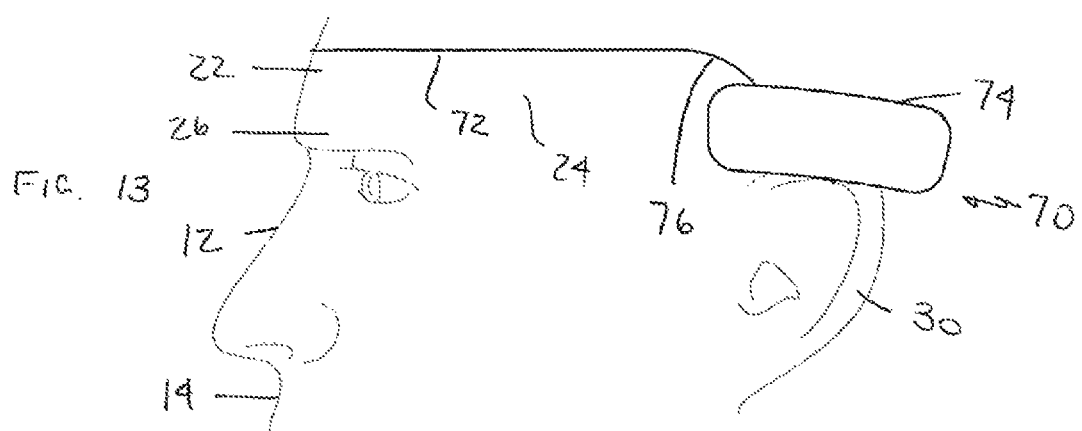
FIG. 13 shows a side view of a fifth apparatus in accordance with an exemplary embodiment of the present disclosure.

FIG. 13 shows a view of a fifth apparatus in accordance with an exemplary embodiment of the present disclosure, indicated generally at 70. As with previous embodiments, apparatus 70 is configured to be positioned on head 12 of subject 14. Apparatus 70 is configured to include a wire portion 72 and at least one device 74. Device 74 can be configured to rest on or grip at least a portion of ear 30 to assist in holding apparatus 70 on head 12. Device 74 can be a speaker, a transmitter, or another device. As with previous embodiments, wire portion 72 is configured to wrap around forehead 22 as a substantially straight wire that extends from one side of head 12 to another side of head 12, and is configured to include a curved portion 76 that is configured to include a downward curve to connect to device 74. Though not shown, an opposite side of wire portion 72 can be similarly configured to connect to a second device 74. In the context of this embodiment, substantially straight means generally flat or horizontal when viewing wire portion 72 from a side or front of head 12. Generally, flat or horizontal does not mean perfectly flat, but can include small curves or variations. In the exemplary embodiment of FIG. 13, wire portion 72 is configured to provide pressure against temples 24 of head 12, thus gripping or holding onto head 12. To provide such pressure, wire portion 72 can be configured as a spring-like material that retains a predetermined shape unless wire portion 72 is moved or stretched by the presence of an object or surface, such as temples 24.

Figure 14:
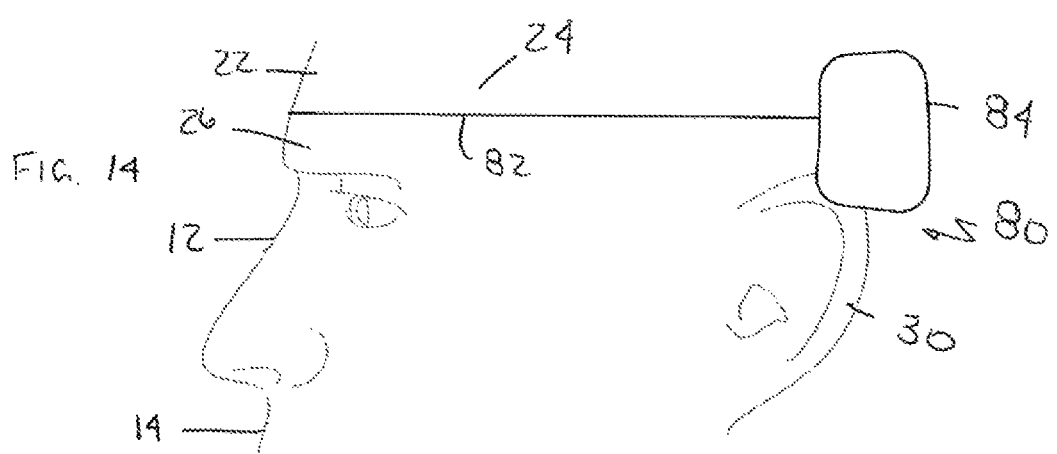
FIG. 14 shows a side view of a sixth apparatus in accordance with an exemplary embodiment of the present disclosure.

FIG. 14 shows a view of a sixth apparatus in accordance with an exemplary embodiment of the present disclosure, indicated generally at 80. As with previous embodiments, apparatus 80 is configured to be positioned on head 12 of subject 14. Apparatus 80 is configured to include a wire portion 82 and at least one device 84. Device 84 can be configured to rest on or grip at least a portion of ear 30 to assist in holding apparatus 80 on head 12. Device 84 can be a speaker, a transmitter, or another device. As with previous embodiments, wire portion 82 is configured to wrap around forehead 22 as a substantially straight wire that extends from one side of head 12 to another side of head 12. Though not shown, an opposite side of wire portion 82 can be similarly configured to connect to a second device 84. In the context of this embodiment, substantially straight means generally flat or horizontal when viewing wire portion 82 from a side or front of head 12. Generally, flat or horizontal does not mean perfectly flat, but can include small curves or variations. In the exemplary embodiment of FIG. 14, wire portion 82 is configured to provide pressure against temples 24 of head 12, thus gripping or holding onto head 12. To provide such pressure, wire portion 82 can be configured as a spring-like material that retains a predetermined shape unless wire portion 82 is moved or stretched by the presence of an object or surface, such as temples 24.

Figure 15:
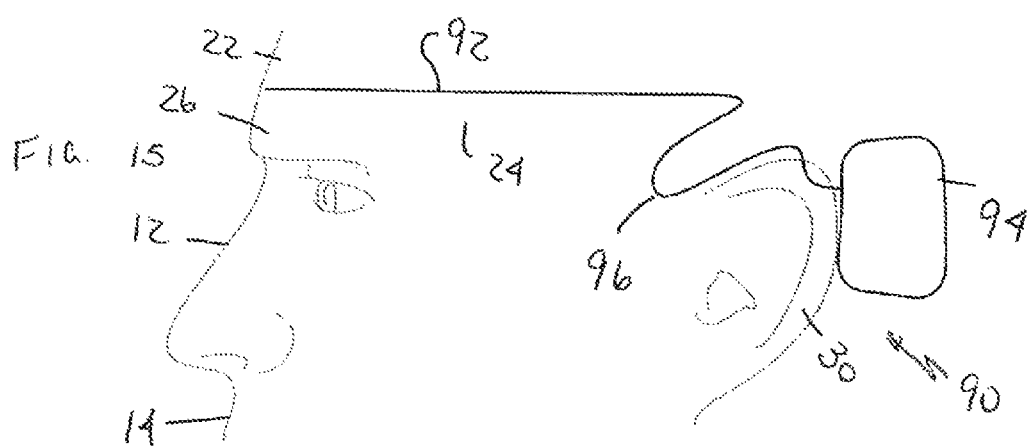
FIG. 15 shows a side view of a seventh apparatus in accordance with an exemplary embodiment of the present disclosure.

FIG. 15 shows a view of a seventh apparatus in accordance with an exemplary embodiment of the present disclosure, indicated generally at 90. As with previous embodiments, apparatus 90 is configured to be positioned on head 12 of subject 14. Apparatus 90 is configured to include a wire portion 92 and at least one device 94. As with previous embodiments, wire portion 92 is configured to wrap around forehead 22 as a substantially straight wire that extends from one side of head 12 to another side of head 12. Though not shown, an opposite side of wire portion 92 can be similarly configured to connect to a second device 94. In the context of this embodiment, substantially straight means generally flat or horizontal when viewing wire portion 92 from a side or front of head 12. Generally, flat or horizontal does not mean perfectly flat, but can include small curves or variations. In the exemplary embodiment of FIG. 15, wire portion 92 is configured to provide pressure against temples 24 of head 12, thus gripping or holding onto head 12. To provide such pressure, wire portion 92 can be configured as a spring-like material that retains a predetermined shape unless wire portion 92 is moved or stretched by the presence of an object or surface, such as temples 24. Wire portion 92 is further configured to include a curvilinear portion 96 that can be configured to support apparatus 90 on an upper portion of ear 30. Additionally, device 94 can be configured to rest on or grip at least a portion of head 12 to assist in holding apparatus 90 on head 12. Device 94 can be a speaker, a transmitter, or another device.

Figure 16:
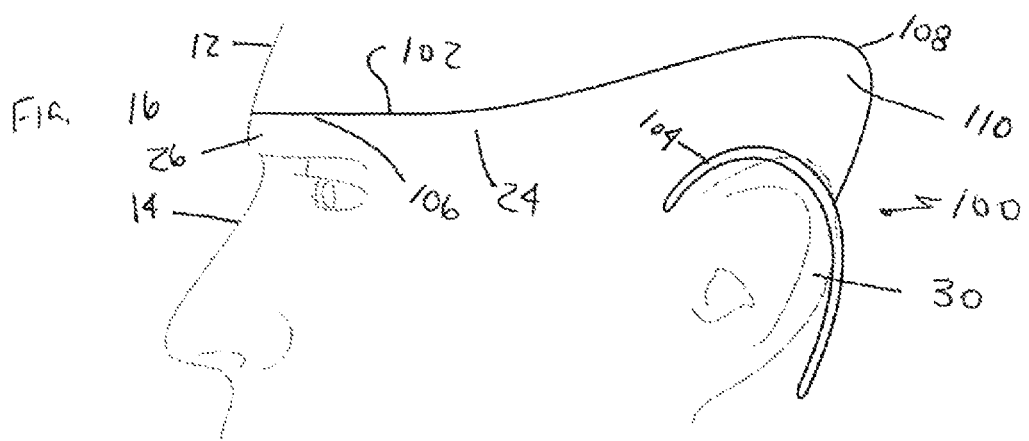
FIG. 16 shows a side view of an eighth apparatus in accordance with an exemplary embodiment of the present disclosure.

FIG. 16 shows a view of an eighth apparatus in accordance with an exemplary embodiment of the present disclosure, indicated generally at 100. As with previous embodiments, apparatus 100 is configured to be positioned on head 12 of subject 14. Apparatus 100 is configured to include a wire portion 102 and at least one device 104. As with previous embodiments, wire portion 102 is configured to wrap around forehead 22 from one side of head 12 to another side of head 12. Though not shown, an opposite side of wire portion 102 can be similarly configured to connect to a second device 104. In contrast to previous embodiments, wire portion 102 is configured with a relatively straight, flat, or horizontal portion 106 positioned on forehead 22 just above eyebrows 26, and a curved portion 108 configured to grip a back portion 110 of head 12. Curved portion 108 curves downwardly to connect to device 104. In the context of this embodiment, relatively straight means generally flat or horizontal when viewing wire portion 102 from a side or front of head 12. Generally, flat or horizontal does not mean perfectly flat, but can include small curves or variations. In the exemplary embodiment of FIG. 16, wire portion 102 is configured to provide pressure against temples 24 of head 12, thus gripping or holding onto head 12, as well as providing pressure against back portion 110 of head 12. To provide such pressure, wire portion 102 can be configured as a spring-like material that retains a predetermined shape unless wire portion 102 is moved or stretched by the presence of an object or surface, such as temples 24. Additionally, device 104 can be configured to rest on at least a portion of ear 30 to assist in supporting apparatus 100 on head 12. Device 104 can be a speaker, a transmitter, or another device.

Figure 17:
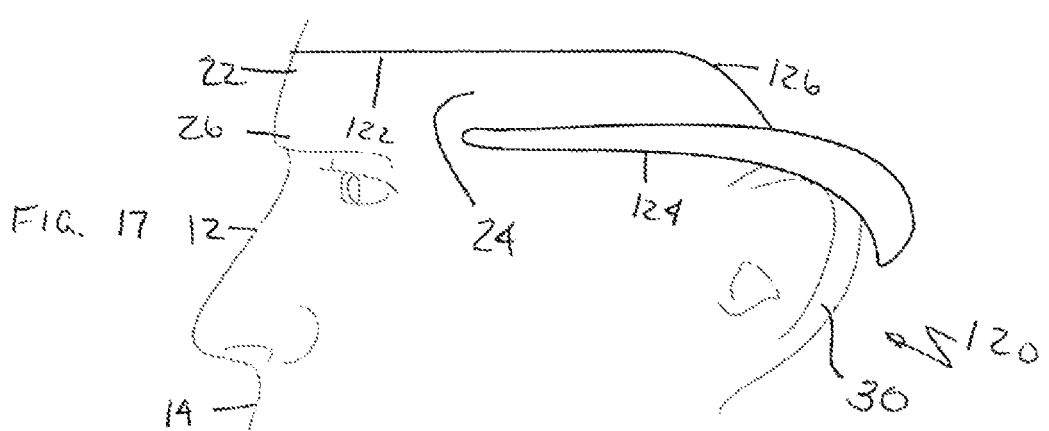
FIG. 17 shows a side view of a ninth apparatus in accordance with an exemplary embodiment of the present disclosure.

FIG. 17 shows a view of a ninth apparatus in accordance with an exemplary embodiment of the present disclosure, indicated generally at 120. As with previous embodiments, apparatus 120 is configured to be positioned on head 12 of subject 14. Apparatus 120 is configured to include a wire portion 122 and at least one device 124. As with previous embodiments, wire portion 122 is configured to wrap around forehead 22 from one side of head 12 to another side of head 12. Though not shown, an opposite side of wire portion 122 can be similarly configured to connect to a second device 124. Wire portion 122 is configured to wrap around forehead 22 as a substantially straight wire that extends from one side of head 12 to another side of head 12, and is configured to include a curved portion 126 that is configured to include a downward curve to connect to device 124. Though not shown, an opposite side of wire portion 122 can be similarly configured to connect to a second device 124. In the context of this embodiment, substantially straight means generally flat or horizontal when viewing wire portion 122 from a side or front of head 12. Generally, flat or horizontal does not mean perfectly flat, but can include small curves or variations. In the exemplary embodiment of FIG. 17, wire portion 122 is configured to provide pressure against temples 24 of head 12, thus gripping or holding onto head 12. To provide such pressure, wire portion 122 can be configured as a spring-like material that retains a predetermined shape unless wire portion 122 is moved or stretched by the presence of an object or surface, such as temples 24. Device 124 can be configured to be at least partially supported on or by a portion of ear 30. Device 124 is configured to extend longitudinally from behind ear 30 toward the front of head 12, ending in an area of temple 24.

Figure 18:
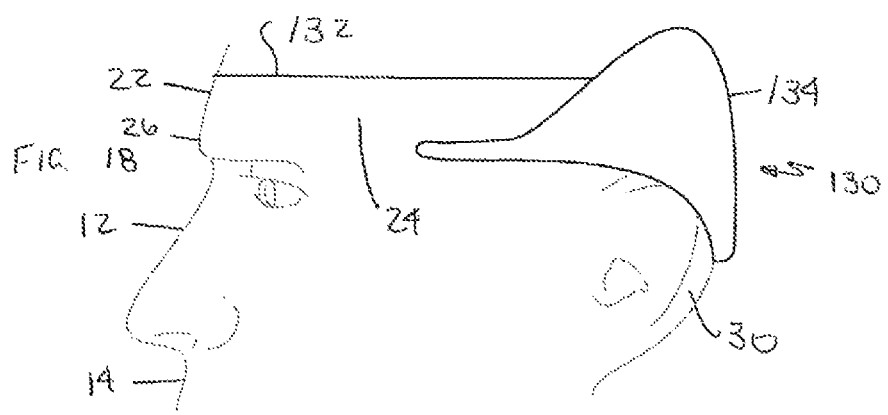
FIG. 18 shows a side view of a tenth apparatus in accordance with an exemplary embodiment of the present disclosure.

FIG. 18 shows a view of a tenth apparatus in accordance with an exemplary embodiment of the present disclosure, indicated generally at 130. As with previous embodiments, apparatus 130 is configured to be positioned on head 12 of subject 14. Apparatus 130 is configured to include a wire portion 132 and at least one device 134. As with previous embodiments, wire portion 132 is configured to wrap around forehead 22 from one side of head 12 to another side of head 12. Though not shown, an opposite side of wire portion 132 can be similarly configured to connect to a second device 134. Wire portion 132 is configured to wrap around forehead 22 as a substantially straight wire that extends from one side of head 12 to another side of head 12 to connect to device 134. Though not shown, an opposite side of wire portion 132 can be similarly configured to connect to a second device 134. In the context of this embodiment, substantially straight means generally flat or horizontal when viewing wire portion 132 from a side or front of head 12. Generally, flat or horizontal does not mean perfectly flat, but can include small curves or variations. In the exemplary embodiment of FIG. 18, wire portion 132 is configured to provide pressure against temples 24 of head 12, thus gripping or holding onto head 12. To provide such pressure, wire portion 132 can be configured as a spring-like material that retains a predetermined shape unless wire portion 132 is moved or stretched by the presence of an object or surface, such as temples 24. Device 134 can be configured to be at least partially supported on or by a portion of ear 30. Device 134 is configured to extend longitudinally from behind ear 30 toward the front of head 12, ending in an area of temple 24.

Figure 19:
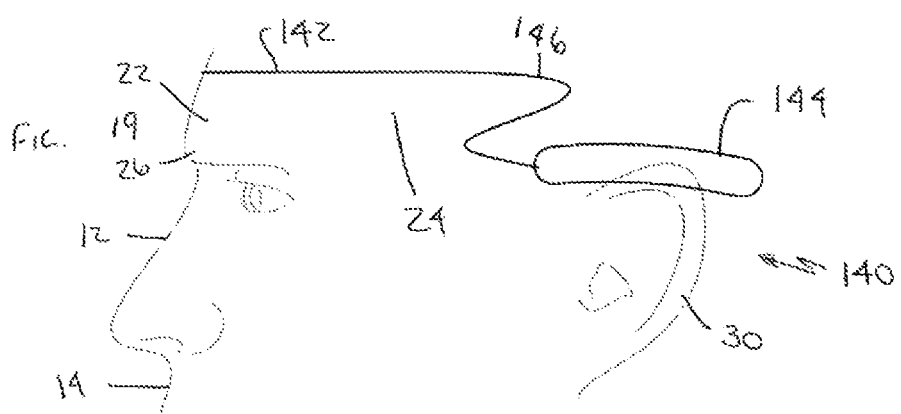
FIG. 19 shows a side view of an eleventh apparatus in accordance with an exemplary embodiment of the present disclosure.

FIG. 19 shows a view of an eleventh apparatus in accordance with an exemplary embodiment of the present disclosure, indicated generally at 140. As with previous embodiments, apparatus 140 is configured to be positioned on head 12 of subject 14. Apparatus 140 is configured to include a wire portion 142 and at least one device 144. As with previous embodiments, wire portion 142 is configured to wrap around forehead 22 from one side of head 12 to another side of head 12. Though not shown, an opposite side of wire portion 142 can be similarly configured to connect to a second device 144. Wire portion 142 is configured to wrap around forehead 22 as a substantially straight wire that extends from one side of head 12 to another side of head 12. Wire portion 142 includes a curvilinear portion 146 that connects the horizontal portion to device 144. Curvilinear portion 146 can be described as a reverse "S," since curvilinear portion 146 appears as a mirror image of the letter "S." However, curvilinear portion 146 on the opposite side of head 12 can be configured as a letter "S," rather than a reverse "S," with a connection to a second device 144. In the context of this embodiment, substantially straight means generally flat or horizontal when viewing wire portion 142 from a side or front of head 12. Generally, flat or horizontal does not mean perfectly flat, but can include small curves or variations. In the exemplary embodiment of FIG. 19, wire portion 142 is configured to provide pressure against temples 24 of head 12, thus gripping or holding onto head 12. To provide such pressure, wire portion 142 can be configured as a spring-like material that retains a predetermined shape unless wire portion 142 is moved or stretched by the presence of an object or surface, such as temples 24. Device 144 can be configured to be at least partially supported on or by a portion of ear 30. Device 144 is configured to extend longitudinally from behind ear 30 toward the front of head 12, ending in an area of temple 24.

Figure 20:
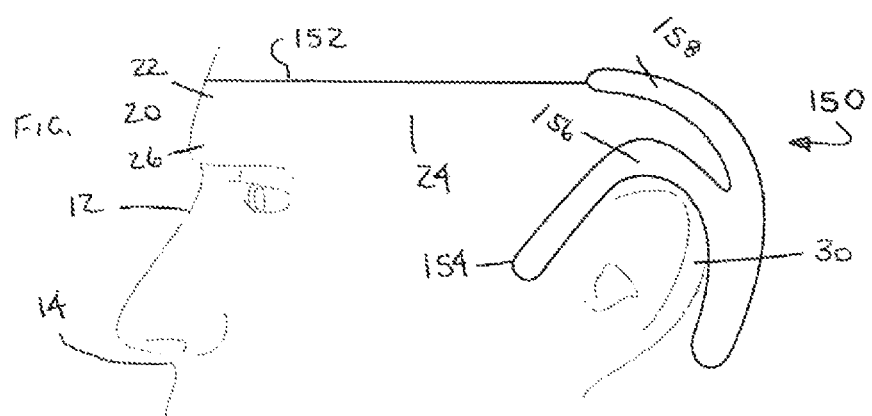
FIG. 20 shows a side view of a twelfth apparatus in accordance with an exemplary embodiment of the present disclosure.

FIG. 20 shows a view of a twelfth apparatus in accordance with an exemplary embodiment of the present disclosure, indicated generally at 150. As with previous embodiments, apparatus 150 is configured to be positioned on head 12 of subject 14. Apparatus 150 is configured to include a wire portion 152 and at least one device 154. As with previous embodiments, wire portion 152 is configured to wrap around forehead 22 from one side of head 12 to another side of head 12. Though not shown, an opposite side of wire portion 152 can be similarly configured to connect to a second device 154. Wire portion 152 is configured to wrap around forehead 22 as a substantially straight wire that extends from one side of head 12 to another side of head 12 that connects to device 154. In the context of this embodiment, substantially straight means generally flat or horizontal when viewing wire portion 152 from a side or front of head 12. Generally, flat or horizontal does not mean perfectly flat, but can include small curves or variations. In the exemplary embodiment of FIG. 20, wire portion 152 is configured to provide pressure against temples 24 of head 12, thus gripping or holding onto head 12. To provide such pressure, wire portion 152 can be configured as a spring-like material that retains a predetermined shape unless wire portion 152 is moved or stretched by the presence of an object or surface, such as temples 24. Device 154 is configured to include a first curvilinear portion 156 configured to wrap around ear 30. In this manner, apparatus 150 can be supported at least partially on or by a portion of ear 30. Device 154 further includes a second curvilinear portion 158 that extends upwardly away from first curvilinear portion 156 to form a "lazy y," with a first end 160 attached or connected to first curvilinear portion 156, and a second end 162 that extends toward temple 24 and forehead 22. Both first curvilinear portion 156 and second curvilinear portion 158 are configured to include an arced portion that curves in the same general direction, as can be readily seen in FIG. 20.

Figure 21:
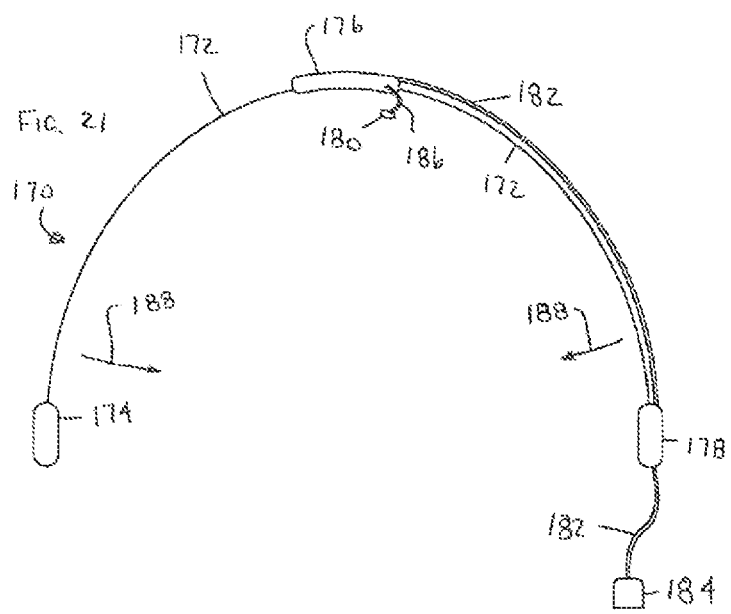
FIG. 21 shows a view of a thirteenth apparatus in accordance with an exemplary embodiment of the present disclosure.
Figure 22:
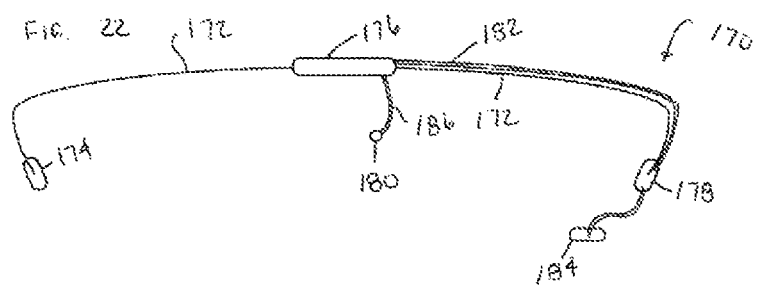
FIG. 22 shows another view of the thirteenth apparatus of FIG. 21.

FIGS. 21 and 22 show a thirteenth apparatus in accordance with an exemplary embodiment of the present disclosure, indicated generally at 170. As with previous embodiments, apparatus 170 is configured to be positioned on head 12 of subject 14. Apparatus 170 is configured to include a wire portion 172. As with previous embodiments, wire portion 172 is configured to wrap around forehead 22 from one side of head 12 to another side of head 12. Wire portion 172 is configured to wrap around forehead 22 as a substantially straight wire that extends from one side of head 12 to another side of head 12. In the context of this embodiment, substantially straight means generally flat or horizontal when viewing wire portion 172 from a side or front of head 12. Generally, flat or horizontal does not mean perfectly flat, but can include small curves or variations. In the exemplary embodiment of FIG. 20, wire portion 172 is configured to provide pressure against temples 24 of head 12, thus gripping or holding onto head 12. To provide such pressure, wire portion 172 can be configured as a spring-like material that retains a predetermined shape unless wire portion 172 is moved or stretched by the presence of an object or surface, such as temples 24. When wire portion 172 is so flexed, it exerts a force in a direction 188, which is toward temple 24 and head 12.

Apparatus 170 is further configured to include a plurality of pads, including first pad 174, second pad 176, and third pad 178, which are configured to provide a smooth contact between apparatus 170 and head 12. Apparatus 170 further yet includes a sensor 180, which is positioned on a flexible support wire 186. Sensor 180 is configured to be positionable on an ABTT terminus 188, which is shown in at least FIG. 9, by moving the position of ABTT sensor 180 on flexible support wire 186. ABTT terminus 180 is described more fully in co-pending U.S. patent application Ser. Nos. 14/512,421, 14/593,848, 14/594,122, and 14/603,353, incorporated herein by reference in their entirety. Sensor 180 can include a temperature sensor (or any other sensor or detector) and is configured to generate signals that represent the temperature of ABTT terminus 188. To provide those signals to a user or medical practitioner, apparatus 170 is configured to include a transmitter and/or connector 184 and an electrical wire extending between ABTT temperature sensor 180 and transmitter and/or connector 184.

Figure 23:
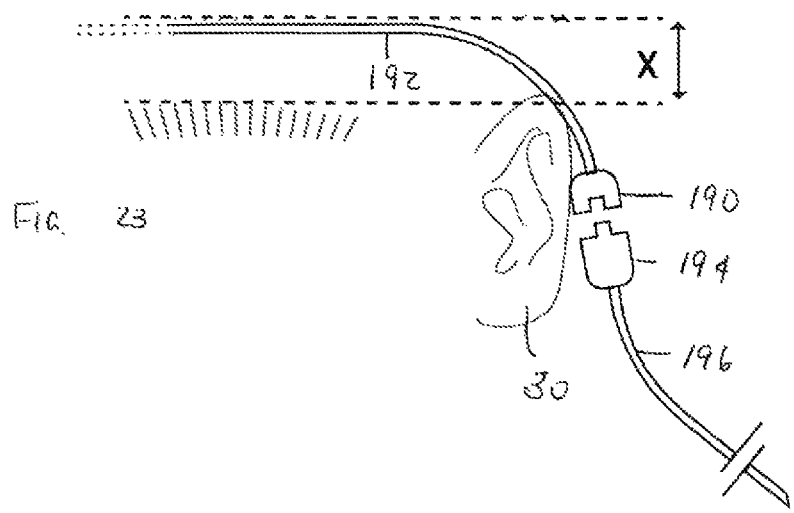
FIG. 23 shows a view of a connection apparatus in accordance with an exemplary embodiment of the present disclosure.

FIG. 23 shows a view of a connection apparatus or device 190 in accordance with an exemplary embodiment of the present disclosure. Connection apparatus 190 is positioned or mounted on a wire 192, which can be similar to any of the wires described in this disclosure. Connection apparatus 190 is configured to mate with another connection apparatus or device 194, which is connected to a separate electronic device (not shown) by an electrical wire 196.

Figure 24:
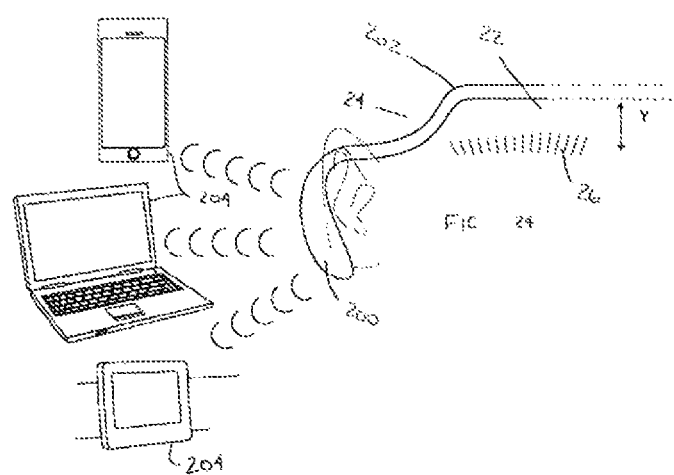
FIG. 24 shows a view of a transmitter apparatus in accordance with an exemplary embodiment of the present disclosure.

FIG. 24 shows a view of a transmitter apparatus 200 in accordance with an exemplary embodiment of the present disclosure. Transmitter apparatus 200 is configured to be positioned on a wire or support apparatus 202, which is configured to be positioned on forehead 22 a distance Y above eyebrow 26. Transmitter apparatus 200 is configured to transmit signals to a separate electronic device 204, which can be configured as a laptop, cell phone, tablet, watch, and the like.

Figure 25:
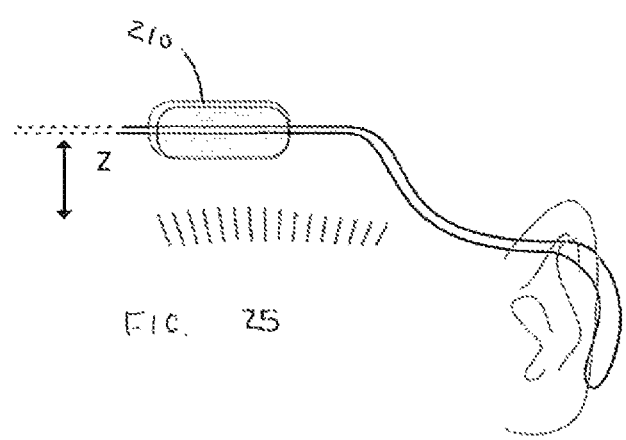
FIG. 25 shows a view of a sensor in accordance with an exemplary embodiment of the present disclosure.

FIG. 25 shows a view of a sensor 210 in accordance with an exemplary embodiment of the present disclosure. Sensor 210, which can be configured as one of a plurality of sensors, including ABTT temperature sensor 180, an EEG, a bispectral index (BIS) monitor, a spectral monitor, and the like. It should be understood that the configurations described herein that are positioned on a head are configured to mount a sensor such as sensor 210.

Figure 26:
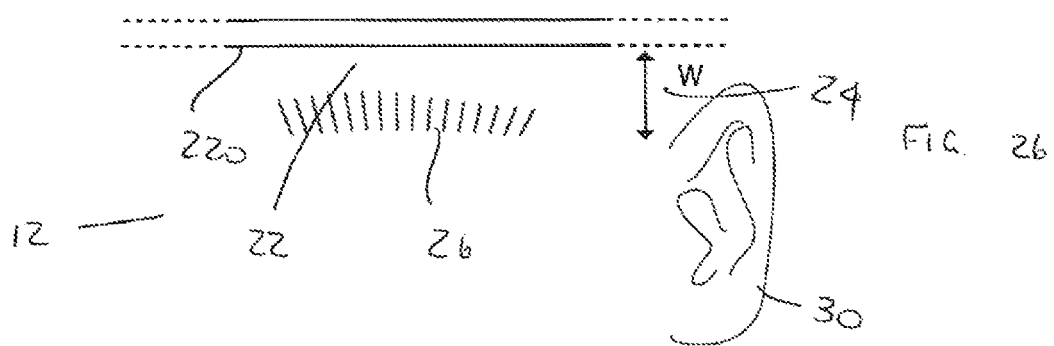
FIG. 26 shows a view of a position of an apparatus in accordance with an exemplary embodiment of the present disclosure.

FIG. 26 shows a view of a position of an apparatus wire 220 in accordance with an exemplary embodiment of the present disclosure. Wire 220 is positioned above ear 20 a distance W.

FIG. 27 shows another view of a position of an apparatus wire 222 in accordance with an exemplary embodiment of the present disclosure. Apparatus wire 222 is configured to be positioned a distance X below the top of ear 30.

Figure 28:
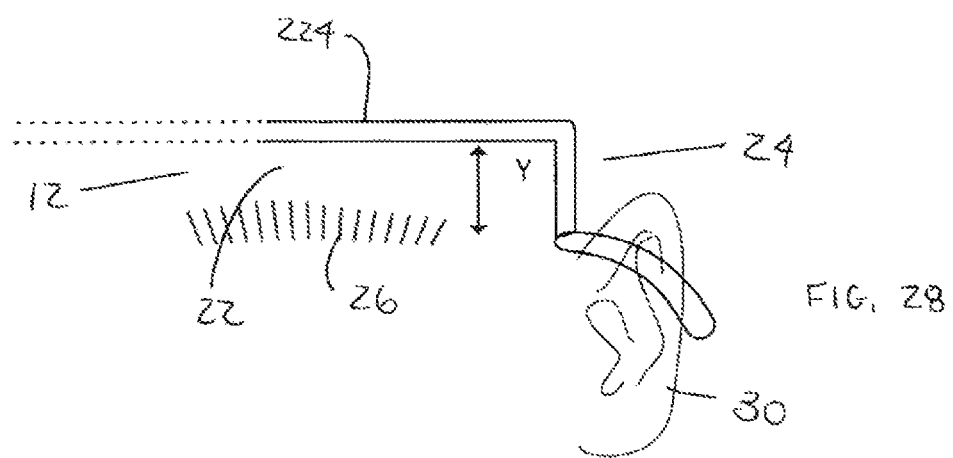
FIG. 28 shows yet another view of a position of an apparatus in accordance with an exemplary embodiment of the present disclosure.

FIG. 28 shows yet another view of a position of an apparatus wire 224 in accordance with an exemplary embodiment of the present disclosure. Apparatus wire 224 is configured to be positioned a distance Y above eyebrow 26.

Figure 29:
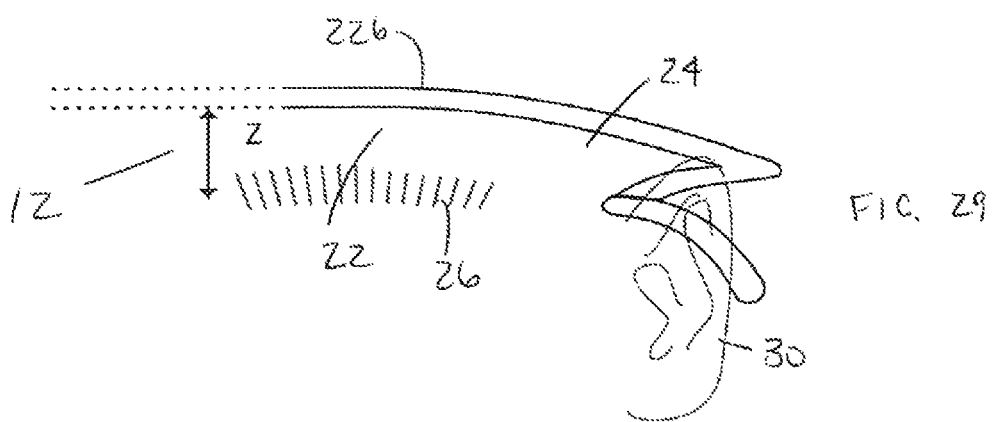
FIG. 29 shows a further view of a position of an apparatus in accordance with an exemplary embodiment of the present disclosure.

FIG. 29 shows a further view of a position of an apparatus wire 226 in accordance with an exemplary embodiment of the present disclosure. Apparatus wire 226 is configured to be positioned a distance Z above eyebrow 26.

Figure 30:
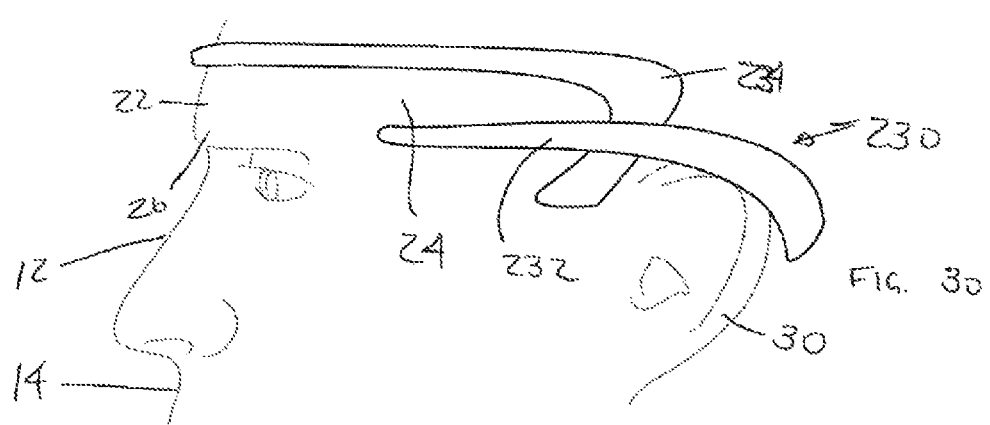
FIG. 30 shows a view of a fourteenth apparatus in accordance with an exemplary embodiment of the present disclosure.

FIG. 30 shows a view of a fourteenth apparatus in accordance with an exemplary embodiment of the present disclosure, indicated generally at 230. Apparatus 230 is configured to include a first support 232 supported at least partially on or over ear 30, extending from ear 30 to temple 24, and a second support 234 connected or attached to first support 232, and extending from temple 24 around forehead 22 to the far side of head 12, where second support 234 connects to another support that is similar to first support 232. First support 232 is movable by sliding upward and slightly back, which moves second support 234 upwardly. Conversely, moving first support 232 by sliding first support 232 downward and slightly forward moves second support 234 downwardly.

Figure 31:
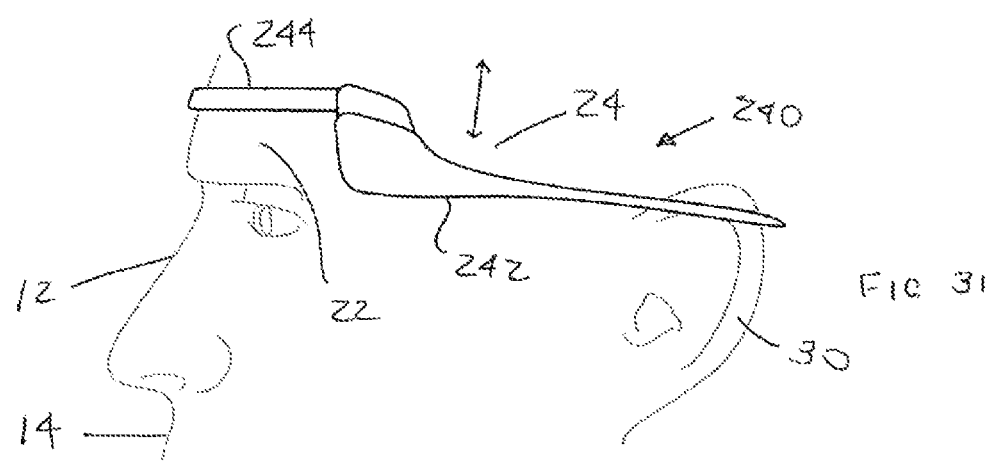
FIG. 31 shows a view of a fifteenth apparatus in accordance with an exemplary embodiment of the present disclosure.

FIG. 31 shows a view of a fifteenth apparatus in accordance with an exemplary embodiment of the present disclosure, indicated generally at 240. Apparatus 240 is configured to include a first support 242 supported at least partially on or over ear 30, extending from ear 30 beyond temple 24 to a location adjacent to forehead 22, and a second support 244 connected or attached to first support 242, which extends across forehead 22 to the far side of head 12, where second support 244 connects to another support that is similar to first support 242. First support 242 is movable by sliding upward and slightly back, which moves second support 244 upwardly. Conversely, moving first support 242 by sliding first support 242 downward and slightly forward moves second support 244 downwardly.

Figure 32:
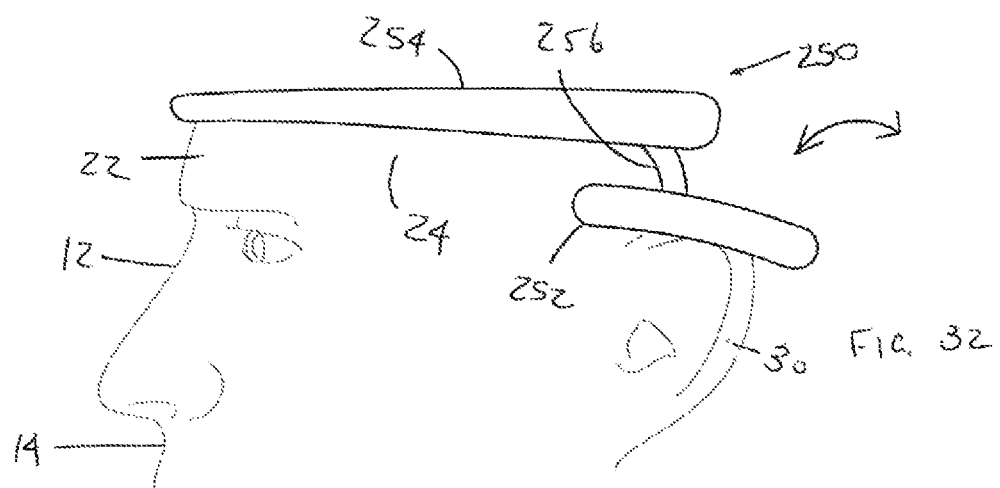
FIG. 32 shows a view of a sixteenth apparatus in accordance with an exemplary embodiment of the present disclosure.

FIG. 32 shows a view of a sixteenth apparatus in accordance with an exemplary embodiment of the present disclosure, indicated generally at 250. Apparatus 250 is configured to include a first support 252 supported at least partially on or over ear 30, extending from ear 30 toward temple 24, a second support 254 that extends from temple 24 across forehead 22 to the far side of head 12. Apparatus 250 further includes a connecting support 256 that extends between first support 252 and second support 254. First support 252 is movable by sliding upward and slightly back, which moves second support 254 upwardly. Conversely, moving first support 252 by sliding first support 252 downward and slightly forward moves second support 254 downwardly.

Figure 33:
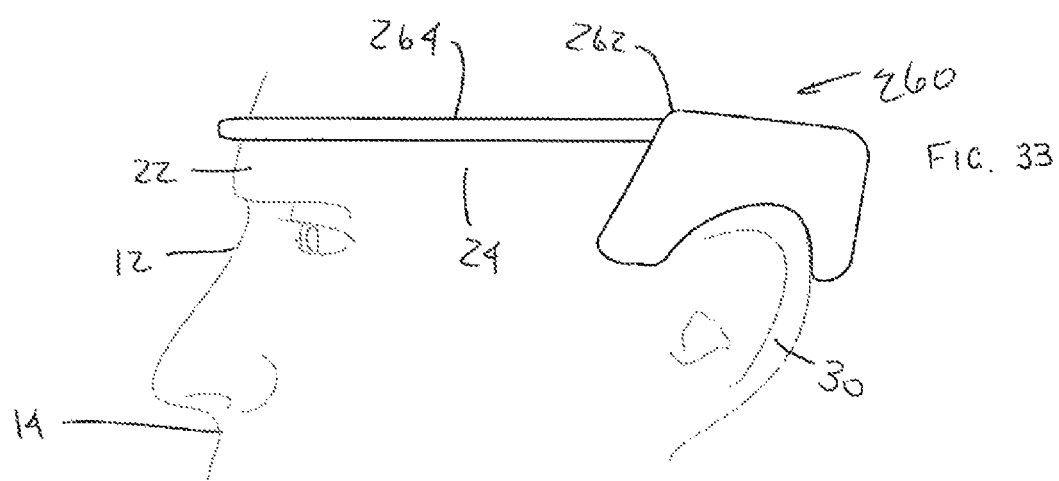
FIG. 33 shows a view of a seventeenth apparatus in accordance with an exemplary embodiment of the present disclosure.

FIG. 33 shows a view of a seventeenth apparatus in accordance with an exemplary embodiment of the present disclosure, indicated generally at 260. Apparatus 260 is configured to include a first support 262 supported at least partially on or over ear 30, extending from ear 30 toward temple 24, and a second support 264 that is connected or attached to first support 262 and extends across temple 24 and then across forehead 22 to the far side of head 12, second support 264 being thicker than wires described for previous embodiments. First support 262 is movable by sliding upward and slightly back, which moves second support 264 upwardly. Conversely, moving first support 262 by sliding first support 262 downward and slightly forward moves second support 264 downwardly.

Figure 34:
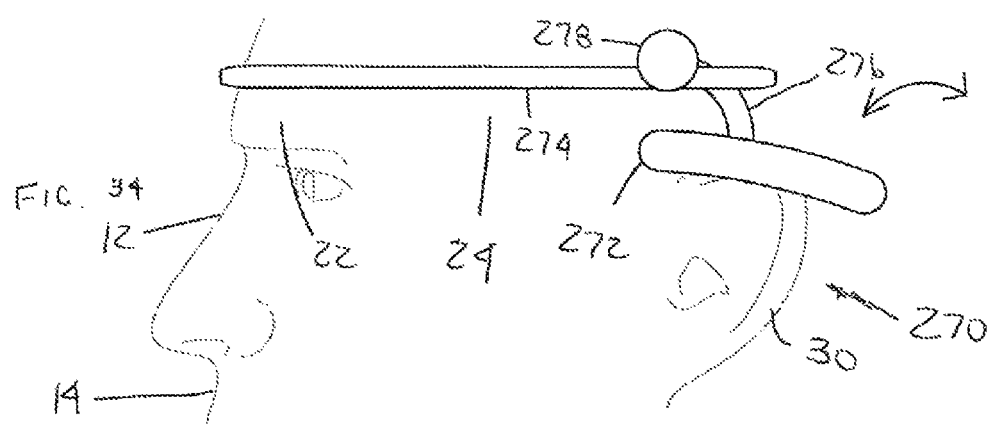
FIG. 34 shows a view of an eighteenth apparatus in accordance with an exemplary embodiment of the present disclosure.

FIG. 34 shows a view of an eighteenth apparatus in accordance with an exemplary embodiment of the present disclosure, indicated generally at 270. Apparatus 270 is configured to include a first support 272 supported at least partially on or over ear 30, and a second support 274 that extends across temple 24 and then across forehead 22 to the far side of head 12. Apparatus 270 is further configured to include a connecting support 276, which is connected to first support 272 at one end, and to a slide 278 at a second, opposite end. Slide 278 slidingly interfaces with second support 274. First support 272 is at a slight angle with respect to second support 274, such that when first support 272, via slide 278, moves along second support 274, apparatus 270 moves upwardly or downwardly on head 12.

Figure 35:
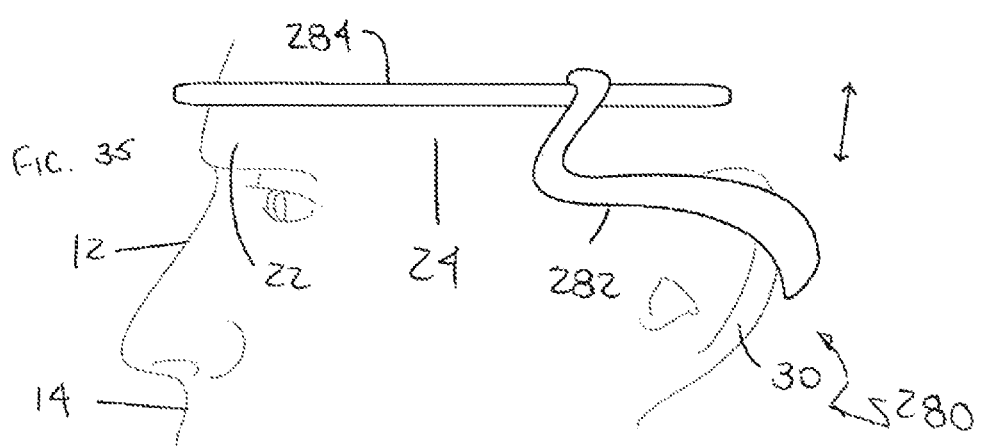
FIG. 35 shows a view of a nineteenth apparatus in accordance with an exemplary embodiment of the present disclosure.

FIG. 35 shows a view of a nineteenth apparatus in accordance with an exemplary embodiment of the present disclosure, indicated generally at 280. Apparatus 280 is configured to include a first support 282 supported at least partially on or over ear 30, extending from ear 30 toward temple 24, and a second support 284 that is connected or attached to first support 282 and extends across temple 24 and then across forehead 22 to the far side of head 12. First support 282 is movable by sliding upward and slightly back, which moves second support 284 upwardly. Conversely, moving first support 282 by sliding first support 282 downward and slightly forward moves second support 284 downwardly.

Figure 36:
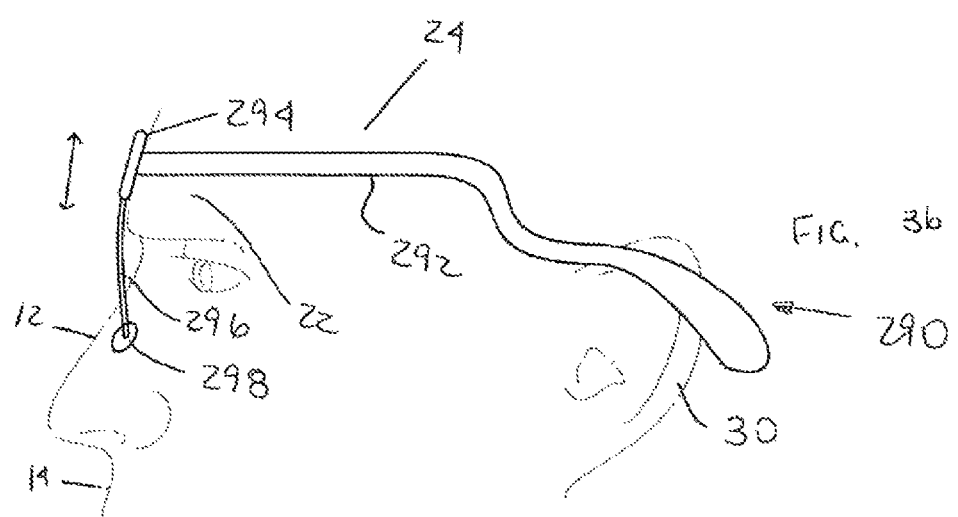
FIG. 36 shows a view of a twentieth apparatus in accordance with an exemplary embodiment of the present disclosure.

FIG. 36 shows a view of a twentieth apparatus in accordance with an exemplary embodiment of the present disclosure, indicated generally at 290. Apparatus 290 is configured to include a first support 292 supported at least partially on or over ear 30, extending from ear 30 across temple 24 and then across forehead 22 to the far side of head 12. First support 292 is supported by contact with temple 24, and partially by forehead 22. Apparatus 290 further includes a second support 294, which is positioned on first support 292, a third support 296, and a support pad 298. Third support 296 is slidingly engaged with second support 294, and movement of third support 296 with respect to second support 294 raises and lowers apparatus 290 on forehead 22, and to a lesser extent on temple 24.

Figure 37:
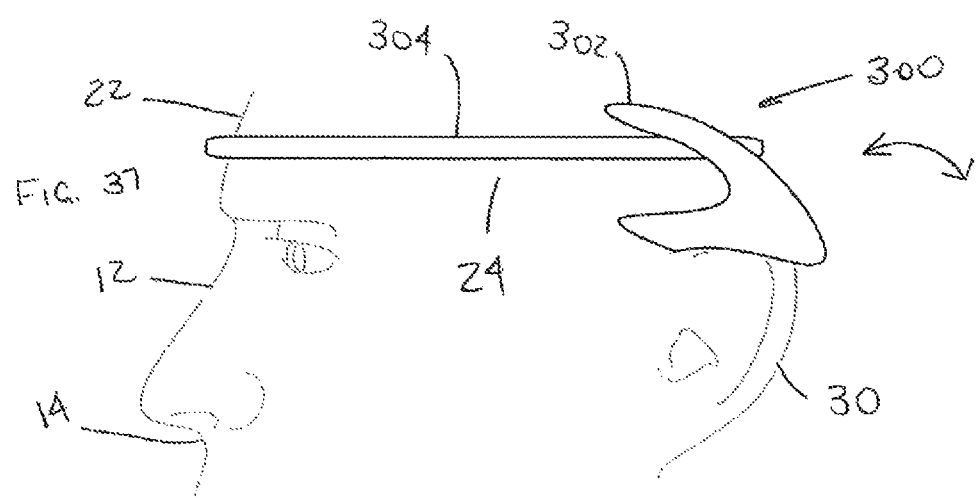
FIG. 37 shows a view of a twenty-first apparatus in accordance with an exemplary embodiment of the present disclosure.

FIG. 37 shows a view of a twenty-first apparatus in accordance with an exemplary embodiment of the present disclosure, indicated generally at 300. Apparatus 300 is configured to include a first support 302 supported at least partially on or over ear 30, and a second support 304 that is connected or attached to first support 282 and extends across temple 24 and then across forehead 22 to the far side of head 12. First support 302 is movable by sliding upward and slightly back, which moves second support 304 upwardly. Conversely, moving first support 302 by sliding first support 302 downward and slightly forward moves second support 304 downwardly.

Figure 38:
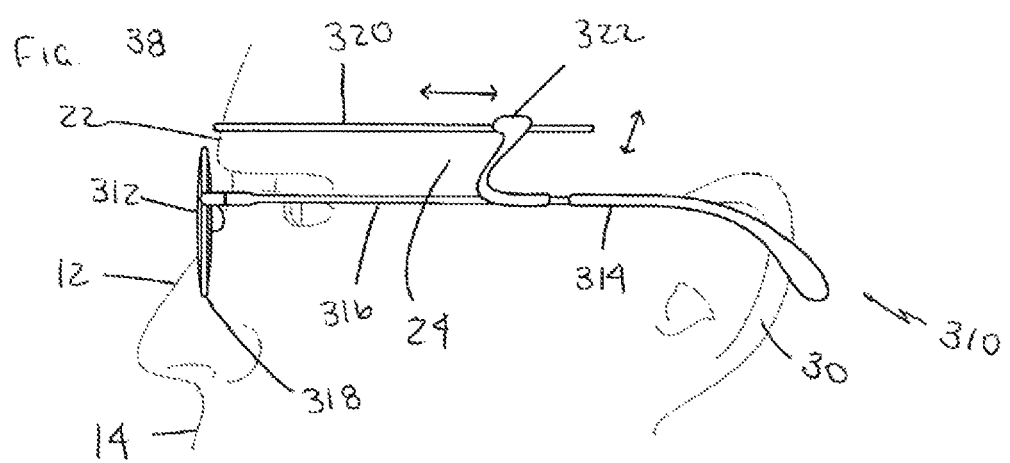
FIG. 38 shows a view of a twenty-second apparatus in accordance with an exemplary embodiment of the present disclosure.
Figure 39:
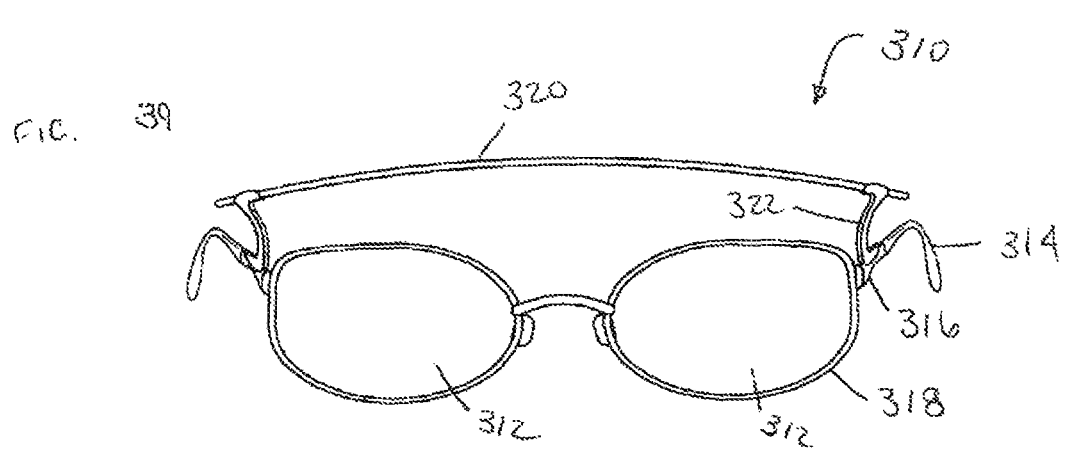
FIG. 39 shows another view of the twenty-second apparatus of FIG. 38.

FIGS. 38 and 39 show a view of a twenty-second apparatus in accordance with an exemplary embodiment of the present disclosure, indicated generally at 310. Apparatus 310 is configured as a pair of glasses supporting one or more lenses 312. Apparatus 310 is configured to include an ear support 314, which is configured to rest between ear 30 and head 12, a first frame support 316 extending from ear support 314, a lens support 318, which is connected to first frame support 316, a second frame support 320 configured to be positioned along left and right temples 24 and forehead 22, and a connecting support 322 that is movably attached to at least one of first frame support 316 and second frame support 320. Connecting support 322 is movable by sliding upward and slightly back, which moves second frame support 320 upwardly. Conversely, moving connecting support 322 by moving connecting support 322 downward slightly forward moves second frame support 320 downwardly.

Figure 40:
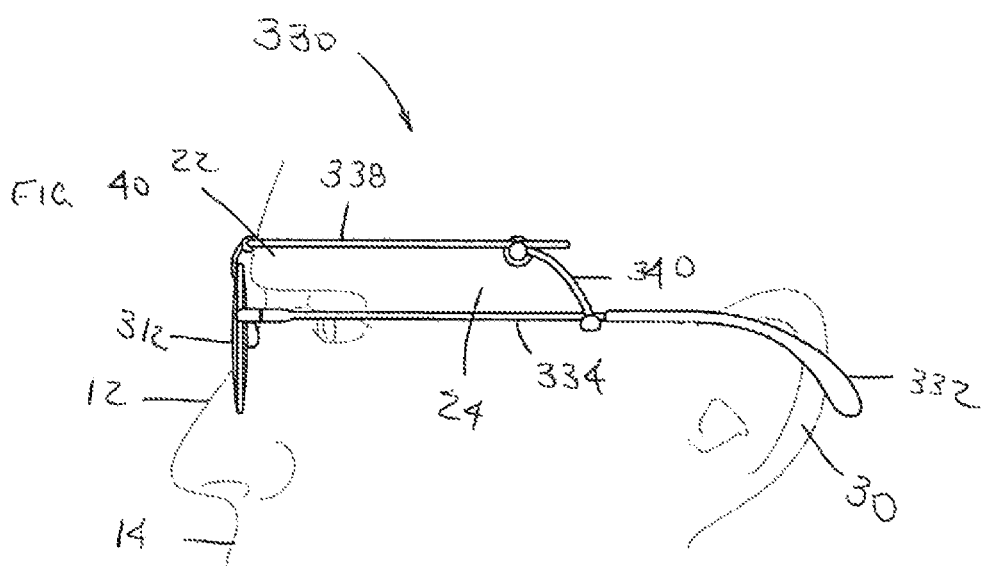
FIG. 40 shows a view of a twenty-third apparatus in accordance with an exemplary embodiment of the present disclosure.
Figure 41:
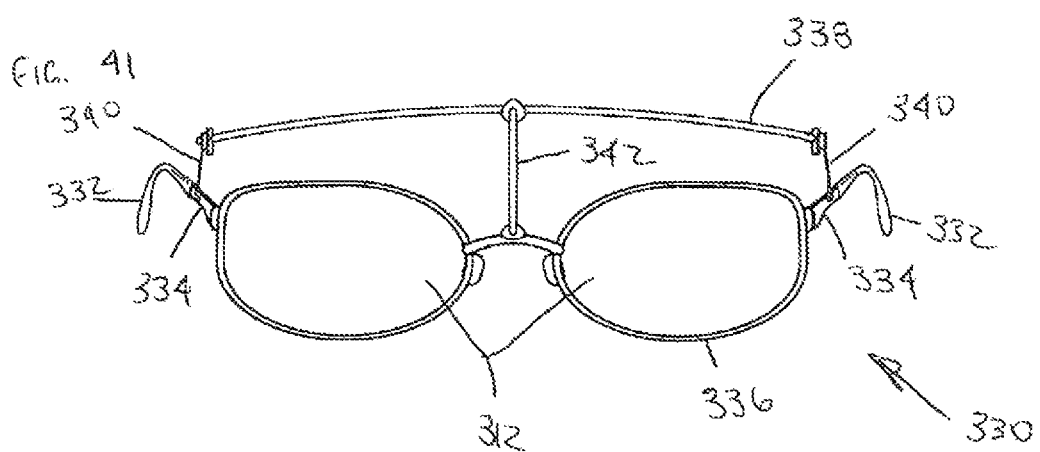
FIG. 41 shows another view of the twenty-third apparatus of FIG. 40.

FIGS. 40 and 41 show a view of a twenty-third apparatus in accordance with an exemplary embodiment of the present disclosure, indicated generally at 330. Apparatus 330 is configured as a pair of glasses supporting one or more lenses 312. Apparatus 330 is configured to include an ear support 332, which is configured to rest between ear 30 and head 12, a first frame support 334 extending from ear support 332, a lens support 336, which is connected to first frame support 334, a second frame support 338 configured to be positioned along left and right temples 24 and forehead 22, and a connecting support 340 that is movably attached to first frame support 334 and second frame support 338. Second frame support 338 is also attached or connected to lens support 336 by a front connecting support 342. Connecting support 340 is movable by sliding left or forward, or right or backward, which adjusts the orientation of apparatus 330 on head 12.

Figure 42:
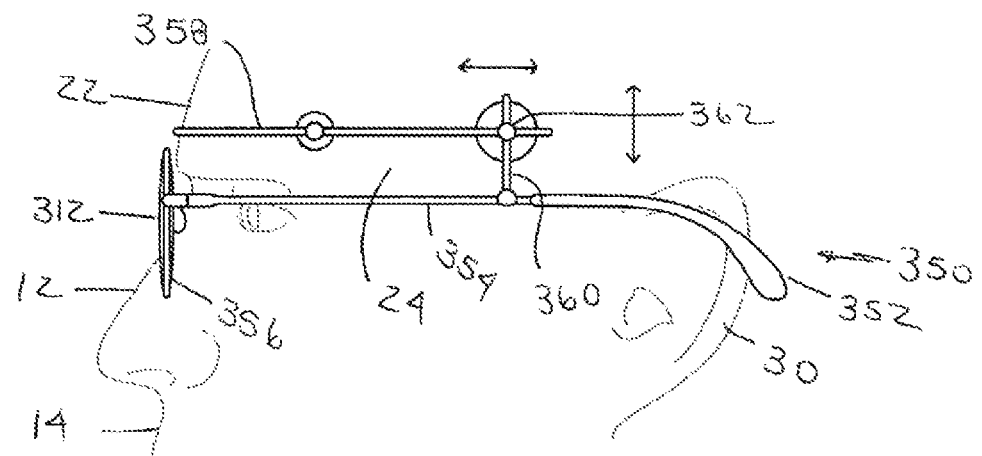
FIG. 42 shows a view of a twenty-fourth apparatus in accordance with an exemplary embodiment of the present disclosure.
Figure 43:
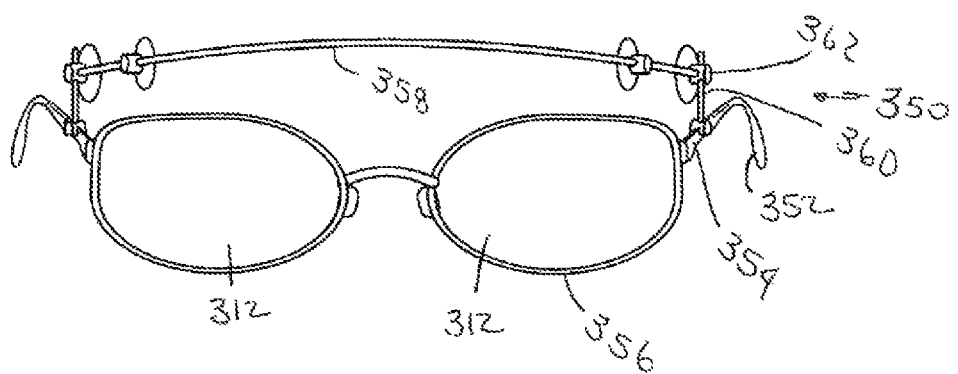
FIG. 43 shows another view of the twenty-fourth apparatus of FIG. 42.

FIGS. 42 and 43 show a view of a twenty-fourth apparatus in accordance with an exemplary embodiment of the present disclosure, indicated generally at 350. Apparatus 350 is configured as a pair of glasses supporting one or more lenses 312. Apparatus 350 is configured to include an ear support 352, which is configured to rest between ear 30 and head 12, a first frame support 354 extending from ear support 352, a lens support 356, which is connected to first frame support 354, a second frame support 358 configured to be positioned along left and right temples 24 and forehead 22, a connecting support 360 attached to first frame support 354 and second frame support 358, and a slider connection 362. Second frame support 358 and connecting support 360 are configured to engage slider connection 362 slidingly. The engagement of second frame support 358 with slider connection 362, which permits forward and rearward movement of second frame support 358 with respect to slider connection 362. The engagement of connecting support 360 with slider connection 362 permits vertical movement of second frame support 358, which is configured to move apparatus 350 up and down on head 12, thus enabling vertical positioning of apparatus 350.

Figure 44:
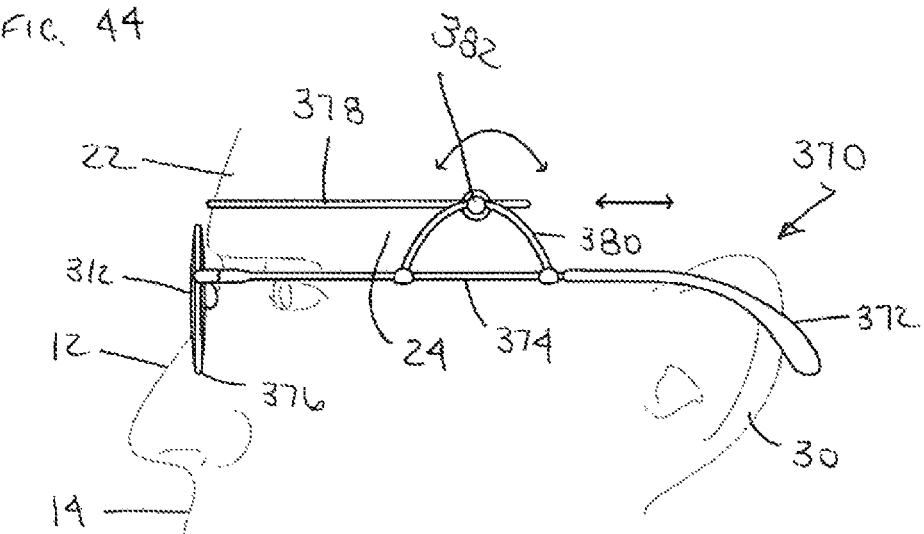
FIG. 44 shows a view of a twenty-fifth apparatus in accordance with an exemplary embodiment of the present disclosure.
Figure 45:
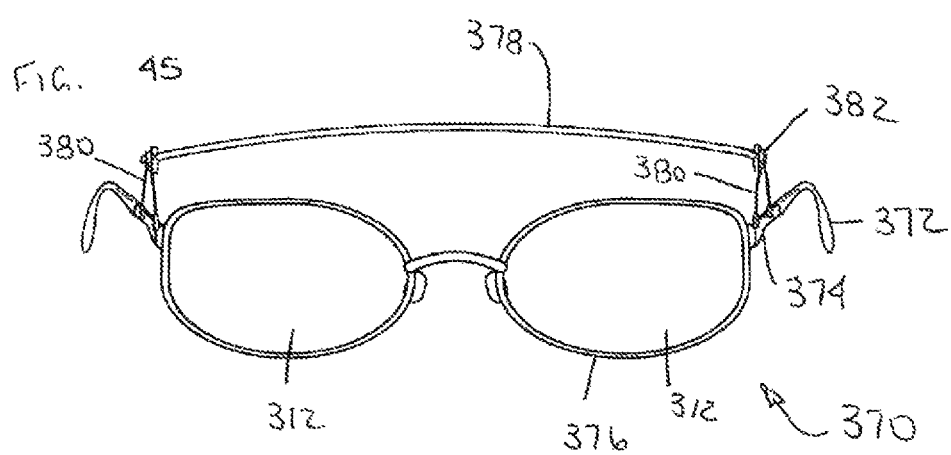
FIG. 45 shows another view of the twenty-fifth apparatus of FIG. 44.
Figure 46:
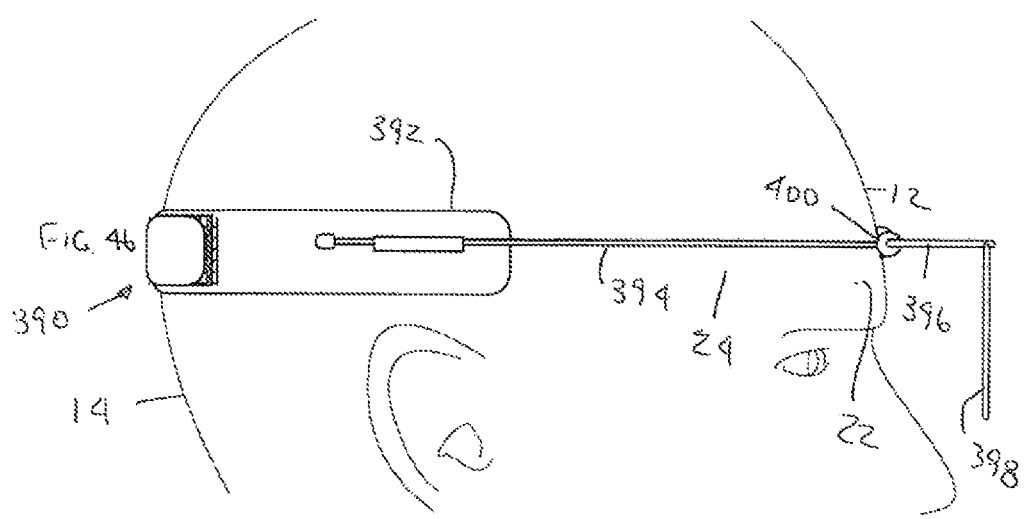
FIG. 46 shows a view of a twenty-sixth apparatus in accordance with an exemplary embodiment of the present disclosure.

FIGS. 44 and 45 show a view of a twenty-fifth apparatus in accordance with an exemplary embodiment of the present disclosure, indicated generally at 370. Apparatus 370 is configured as a pair of glasses supporting one or more lenses 312. Apparatus 370 is configured to include an ear support 372, which is configured to rest between ear 30 and head 12, a first frame support 374 extending from ear support 372, a lens support 376, which is connected to first frame support 374, a second frame support 378 configured to be positioned along left and right temples 24 and forehead 22, a connecting support 380 attached to first frame support 374 and second frame support 378, and a slider connection 382. Second frame support 378 and connecting support 380 are configured to engage slider connection 382 slidingly. The engagement of second frame support 378 with slider connection 382 permits forward and rearward movement of second frame support 378 with respect to slider connection 382. As second frame support 378 moves back and forward, it also provides vertical movement of second frame support 378 on forehead 22, which thus enables vertical positioning of apparatus 370 on head 12.

FIGS. 46-49 show views of a twenty-sixth apparatus in accordance with an exemplary embodiment of the present disclosure, indicated generally at 390. Apparatus 390 is configured as a pair of eyeglasses. Apparatus 390 is configured to include a strap 392, which is adjustable to secure apparatus 390 to head 12, a first frame support 394 extending from strap 392, a lens support 396, and at least one lens 398. Apparatus 390 is further configured to include at least one pad 400. Each lens 398 is configured to engage lens support 396 slidingly. It should be apparent that apparatus 390 is configured to be supported above ears 30 and above nose 28 along forehead 22, temples 24, and along the back of head 12. Lens support 396 is configured to include a groove, slot, slit, or other engaging feature 402. Each lens 398 is configured to include a mating feature 404 that is configured to engage groove 402.

Figure 50:
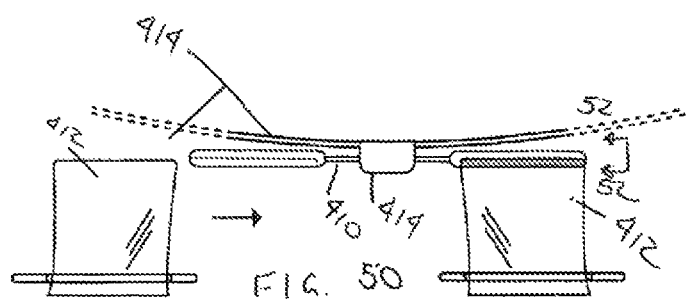
FIG. 50 shows a view of an attachment configuration compatible with the apparatus of FIGS. 46-49.
Figure 51:
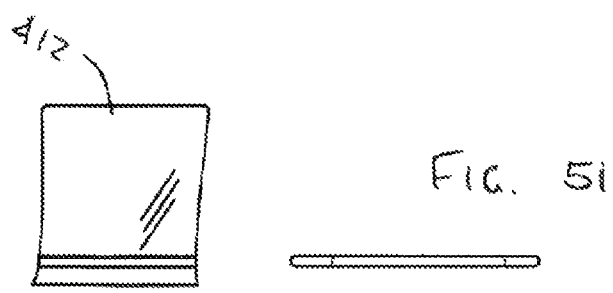
FIG. 51 shows a view of a lens compatible with the attachment configuration of FIG. 50.
Figure 52:
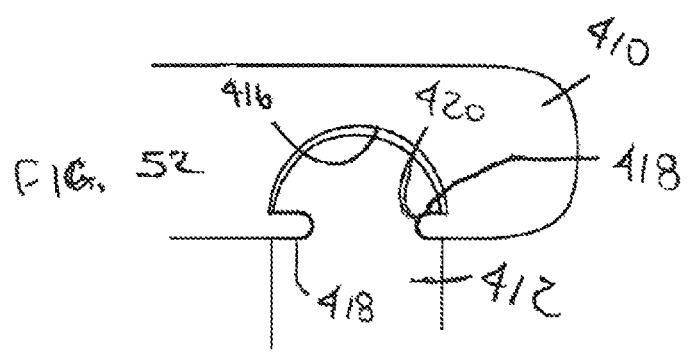
FIG. 52 shows a view from a side of the attachment configuration of FIG. 50, along the lines 52-52.

FIGS. 50-52 show a view of an attachment configuration compatible with the apparatuses of FIGS. 46-49. A lens support 410 is configured to support at least one lens 412. Lens support 410 is support by a frame support 414. Lens support 410 is configured to include a slot 416. Lens support 410 further includes at least one protrusion or finger that extends from lens support 410 into slot 416. Lens 412 is configured to include at least one mating lens slot 420. To attach lens 412 to lens support 410, lens slots 420 are slid onto protrusions 418 as an end of lens 412 is positioned into slot 416.

Figure 53:
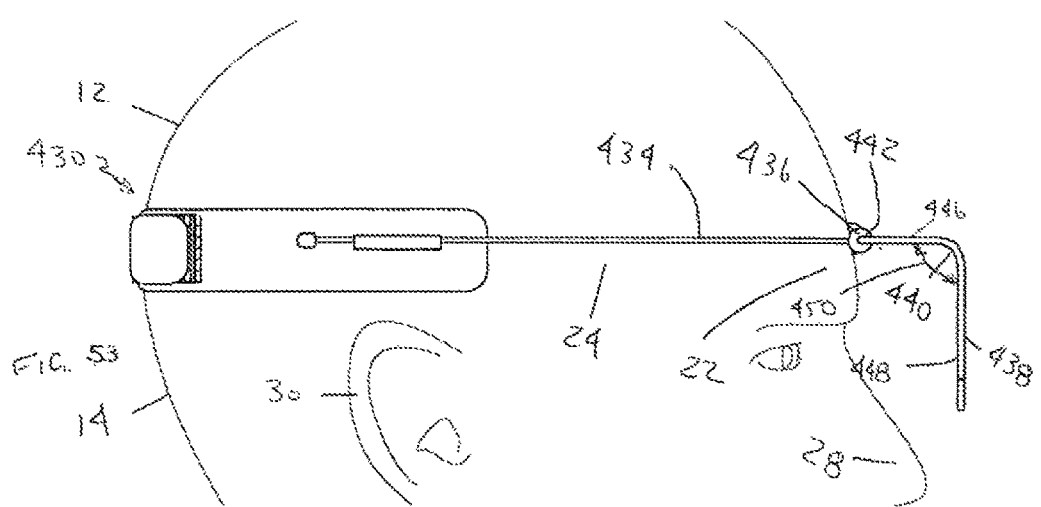
FIG. 53 shows a view of a twenty-seventh apparatus in accordance with an exemplary embodiment of the present disclosure.
Figure 54:
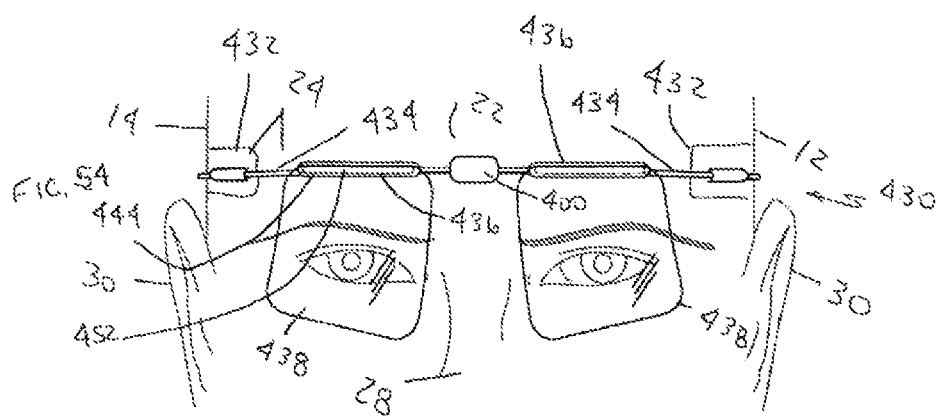
FIG. 54 shows another view of the twenty-seventh apparatus of FIG. 53.
Figure 55:
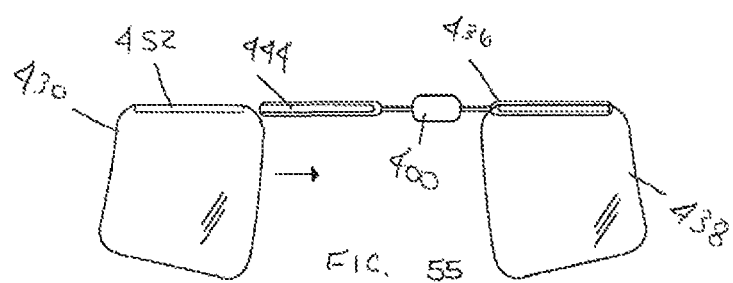
FIG. 55 shows a portion of the twenty-seventh apparatus of FIG. 53.

FIGS. 53-55 show a twenty-seventh apparatus in accordance with an exemplary embodiment of the present disclosure, indicated generally at 430. Apparatus 430 is configured to include a strap 432, which is adjustable to secure apparatus 430 to head 12, a first frame support 434 extending from strap 432, a lens support 436, and at least one lens 438. Apparatus 430 is further configured to include at least one pad 400. Each lens 438 is configured to include a curved portion 440, which forms each lens 438 into a first lens portion 446 and a second portion 448 at an angle 450, which may be 90 degrees, to the first portion. An end 442 of each lens 438 is configured to engage lens support 436 slidingly. It should be apparent that apparatus 430 is configured to be supported above ears 30 and above nose 28 along forehead 22, temples 24, and along the back of head 12. Lens support 436 is configured to include a groove, slot, slit, or other engaging feature 444. Each lens 438 is configured to include a mating feature 452 that is configured to engage slot 444.

Figure 56:
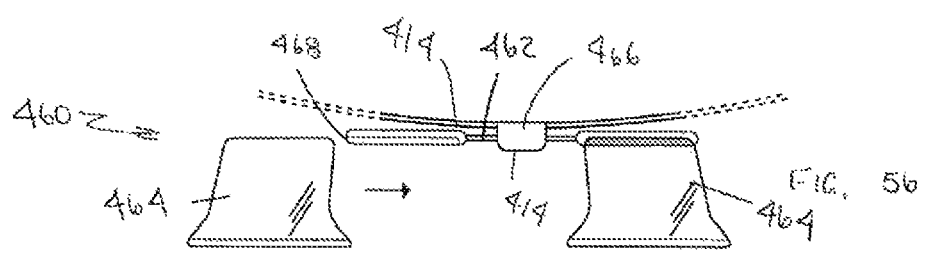
FIG. 56 shows a view of a twenty-eighth apparatus in accordance with an exemplary embodiment of the present disclosure.

FIG. 56 shows a view of a twenty-eighth apparatus in accordance with an exemplary embodiment of the present disclosure, indicated generally at 460. Apparatus 460 is configured to include a lens support 462, which is configured to support at least one lens 464. Lens support 462 is supported by a frame support 466. Lens support 462 is configured to include a slot 468. Slot 468 and the mating features of slot 468 and lens 464 are similar to the features of FIGS. 50-52.

Figure 57:
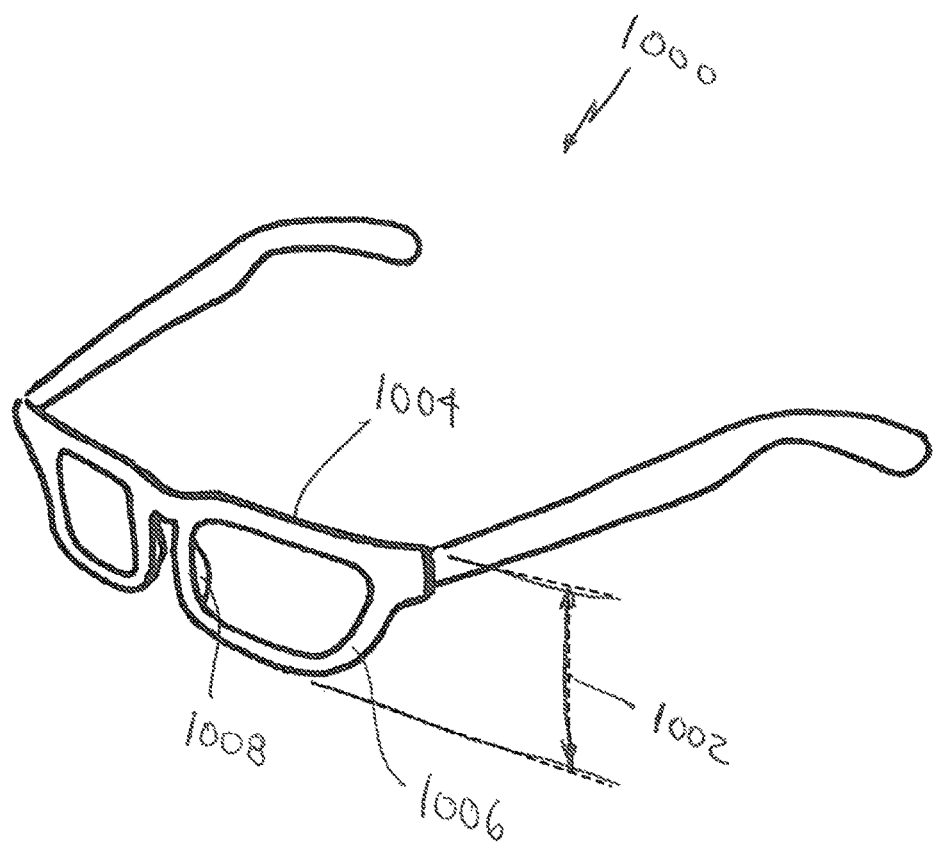
FIG. 57 shows a view of a prior art frame.
Figure 58:
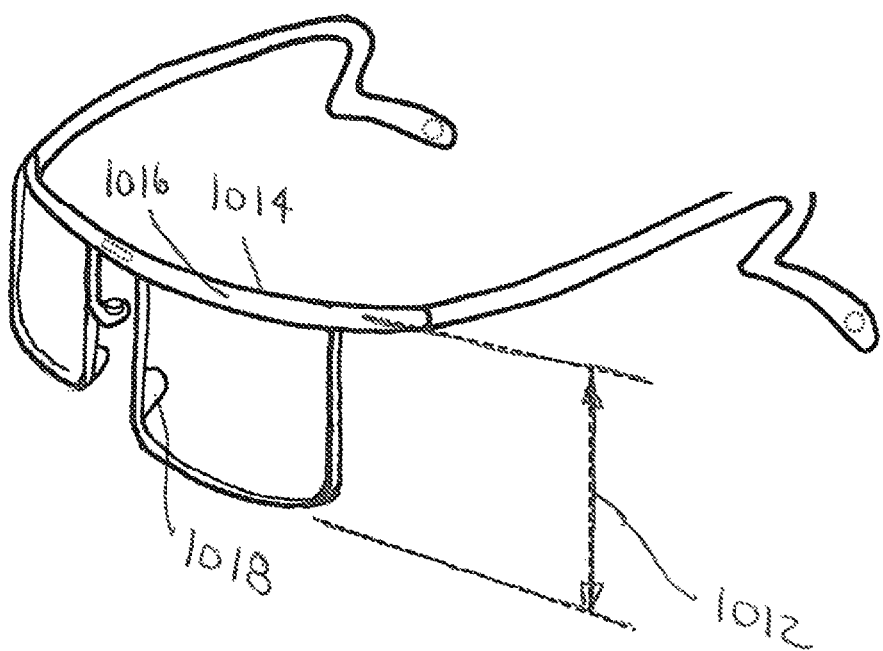
FIG. 58 shows a view of a twenty-ninth apparatus in the form of a sensing frame in accordance with an exemplary embodiment of the present disclosure.

FIGS. 57 and 58 show comparisons between conventional frames and an exemplary embodiment sensing frame of the present disclosure.

FIG. 57 shows a view of a conventional frame 1000, which includes a dimension 1002 from an upper or top portion 1004 of a front frame 1006 to a nose pad 1008.

FIG. 58 shows a sensing frame, indicated generally at 1010, in accordance with an exemplary embodiment of the present disclosure. Sensing frame 1010 includes a dimension 1012 from a top or upper portion 1014 of an upper frame 1016 to a nose pad 1018. Dimension 1012 of sensing frame 1010 of the present disclosure is longer than dimension 1002 of conventional frames of the prior art by virtue of the higher positioning of upper frame 1016 of the present disclosure with respect to forehead 22. Nose pads 1018 are located far from upper frame 1016 in the present disclosure, in contrast to nose pads 1008 of conventional frames 1000, which are located close to top portion 1004, as shown in FIG. 57.

Figure 58A:
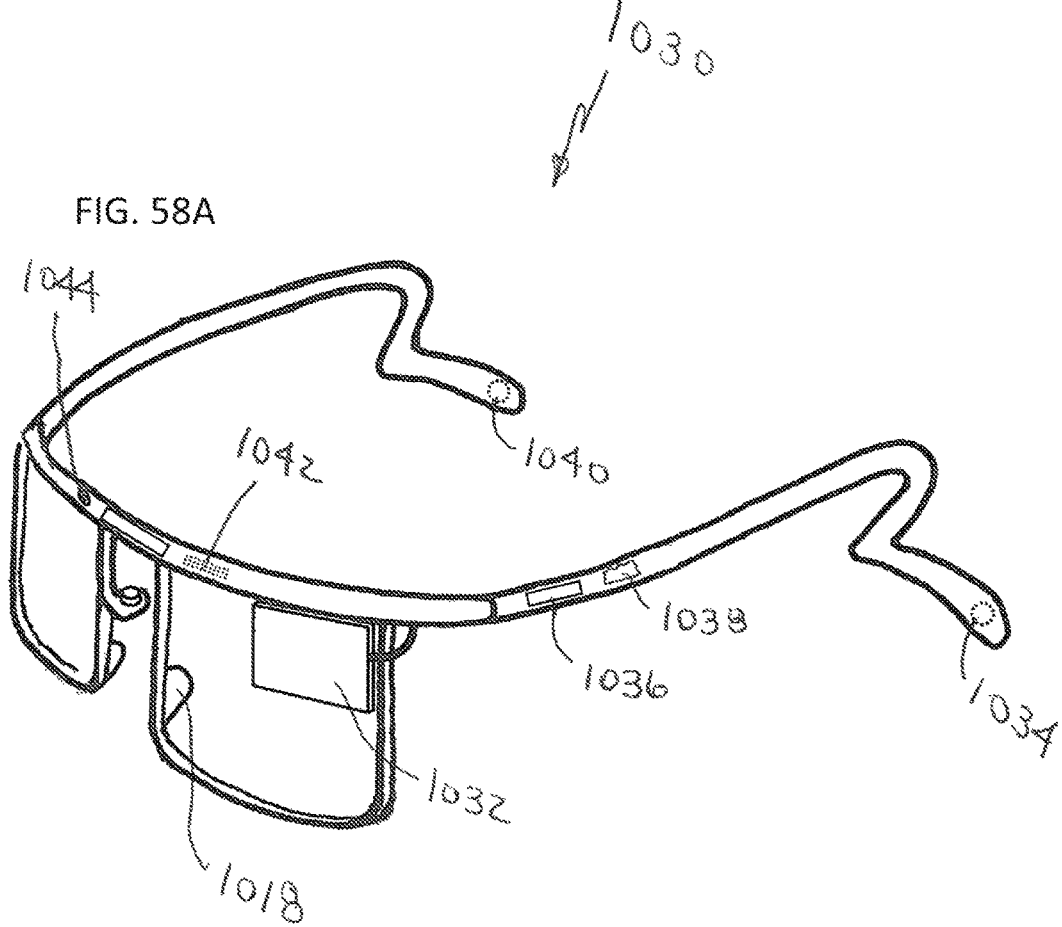
FIG. 58A shows a view of a thirtieth apparatus in accordance with an exemplary embodiment of the present disclosure.
Figure 58B:
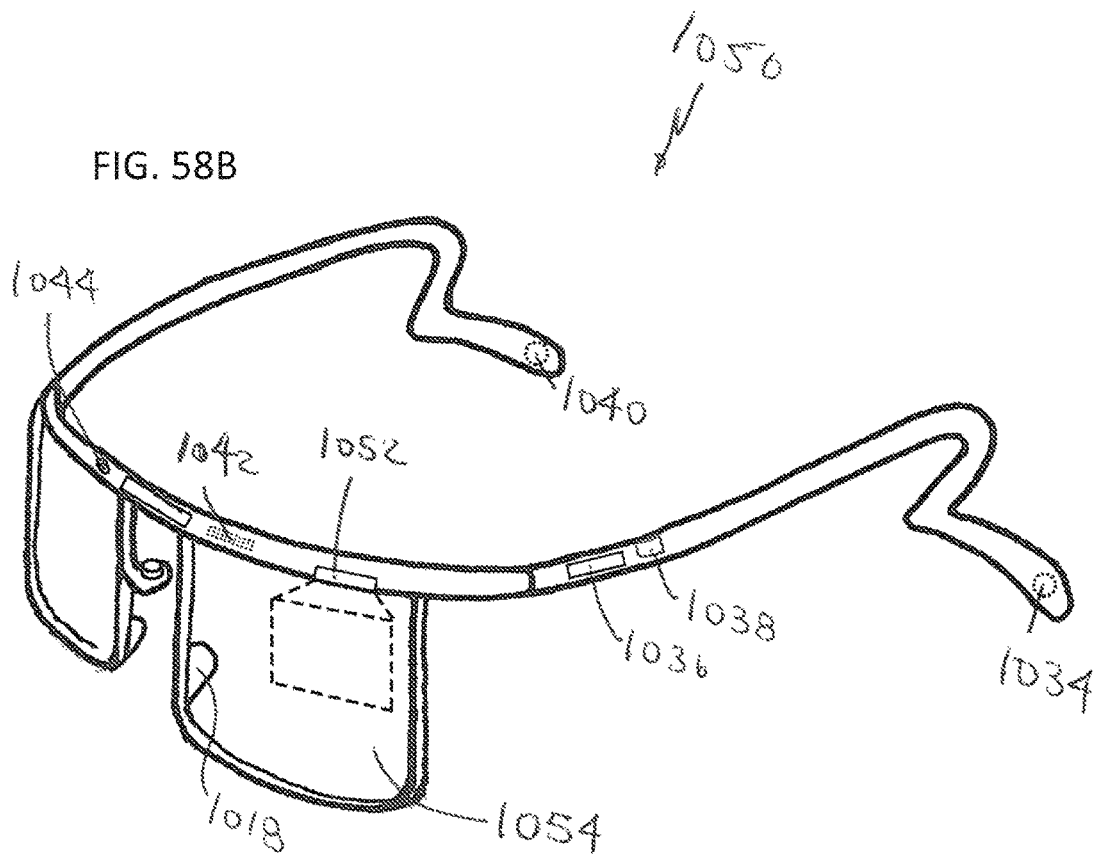
FIG. 58B shows a view of a thirty-first apparatus in accordance with an exemplary embodiment of the present disclosure.

By being, for example 1 cm above eyebrow 26, upper frame 1016 has an extra 1 cm of space for hardware, allowing thereby a unique configuration for having extra hardware, and to remain cosmetically and functionally attractive with a thin configuration. Accordingly, FIG. 58A shows a sensing frame 1030 in accordance with an exemplary embodiment that includes features of sensing frame 1010 of FIG. 58, and is labelled accordingly. Sensing frame 1030 includes multiple hardware that can include a screen or display 1032, a transmitter 1034, a processor 1036, a non-transitory memory 1038, a speaker 1040, a microphone 1042, and a camera 1044. FIG. 58B is another embodiment sensing frame, indicated generally at 1050, in accordance with an exemplary embodiment of the present disclosure. Sensing frame 1050 includes some features common to sensing frames 1010 and 1030, and is labelled accordingly. Sensing frame 1050 further includes a projector 1046 for projecting still images or video, such as onto a lens 1054.

Figure 59:
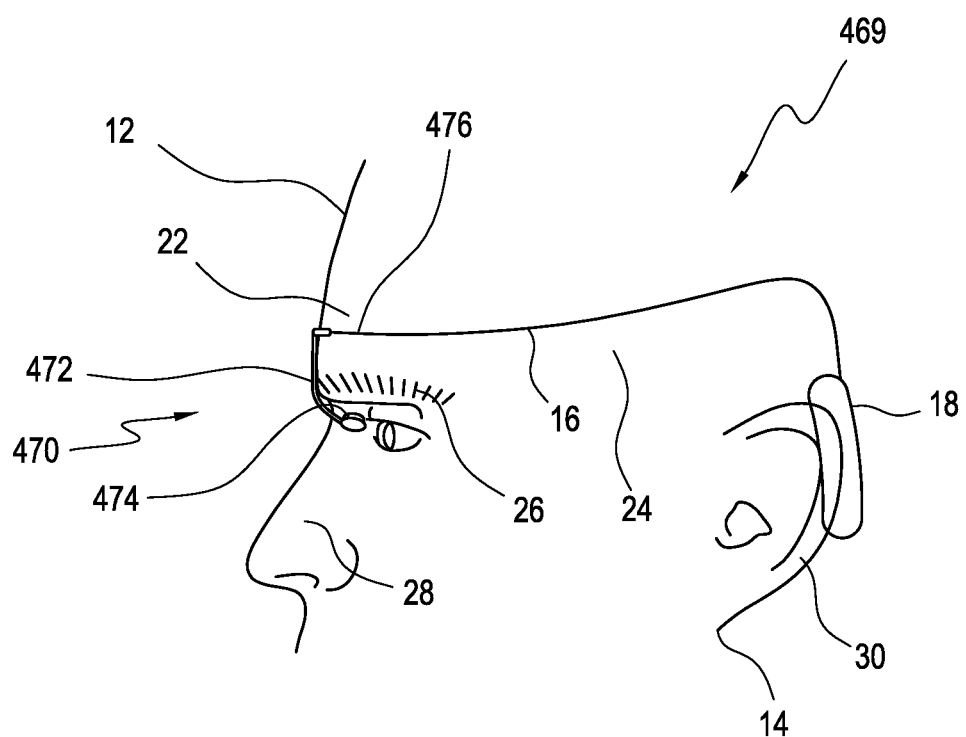
FIG. 59 shows a view of a thirty-second apparatus in accordance with an exemplary embodiment of the present disclosure.

FIG. 59 is the embodiment of FIG. 1 modified as a sensing frame 469 to include a sensor assembly 470 having an arm 472 and a sensor 474, arm 472 connecting sensor 474 to a forehead frame or upper frame portion 476 of curvilinear wire portion 16.

Figure 60:
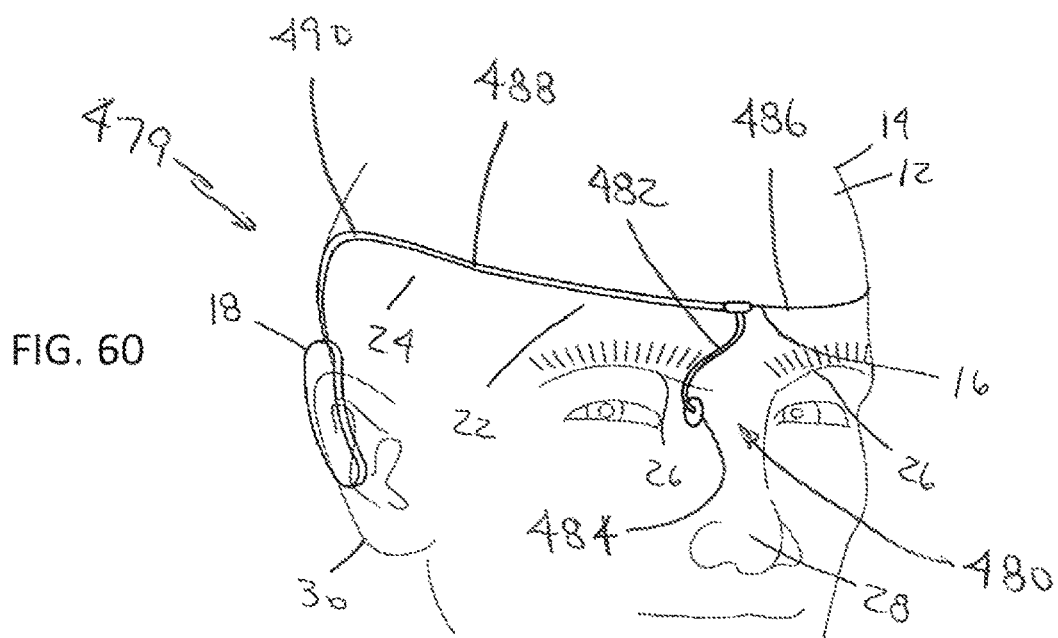
FIG. 60 shows a view of a thirty-third apparatus in accordance with an exemplary embodiment of the present disclosure.

FIG. 60 is the embodiment of FIG. 3 modified as a sensing frame 479 to include a sensor assembly 480 having an arm 482 and a sensor 484, arm 482 being connected to an upper or forehead frame 486 of curvilinear wire portion 16. Upper frame 486 contains wire 488 that connects sensor assembly 480 with electronics and a power source positioned in a housing of device 18 at the end of a temple portion 490 the curvilinear wire portion 16.

Figure 61:
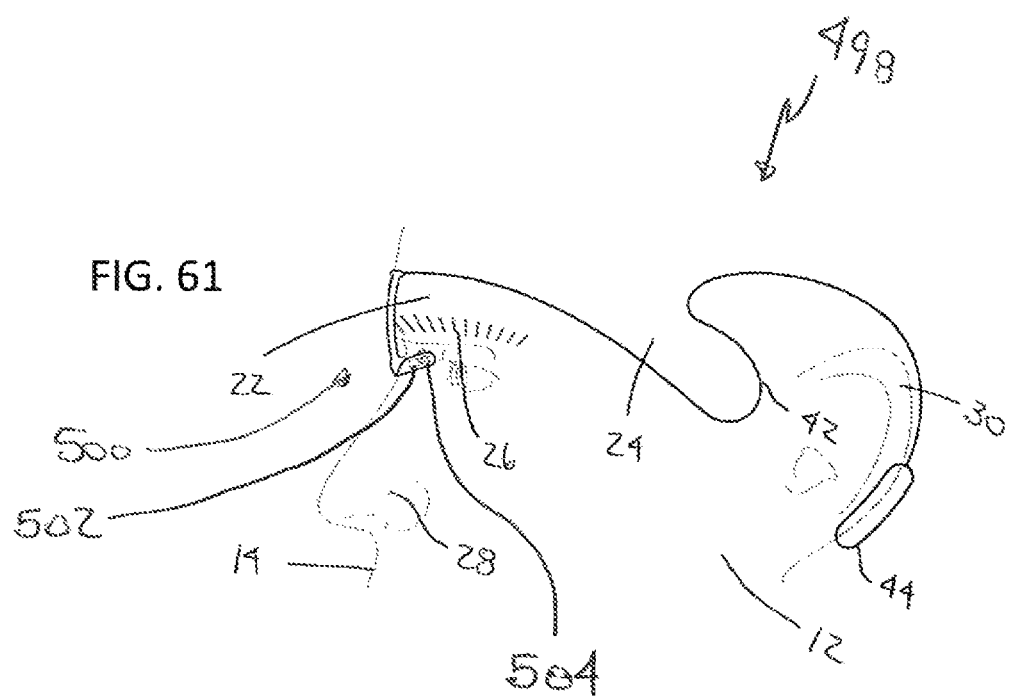
FIG. 61 shows a view of a thirty-fourth apparatus in accordance with an exemplary embodiment of the present disclosure.

FIG. 61 is the embodiment of FIG. 4 modified as a sensing frame 498 to include an emitter-detector assembly 500 having an emitter 502 and a detector 504.

Figure 62:
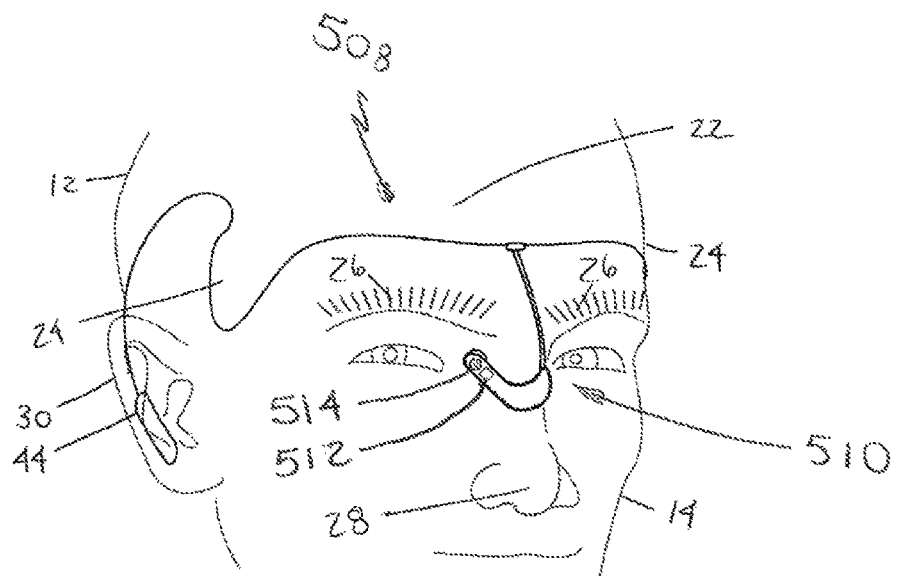
FIG. 62 shows a view of a thirty-fifth apparatus in accordance with an exemplary embodiment of the present disclosure.

FIG. 62 is the embodiment of FIG. 6 modified as a sensing frame 508 to include an emitter-detector assembly 510 having an emitter 512 and a detector 514.

Figure 63:
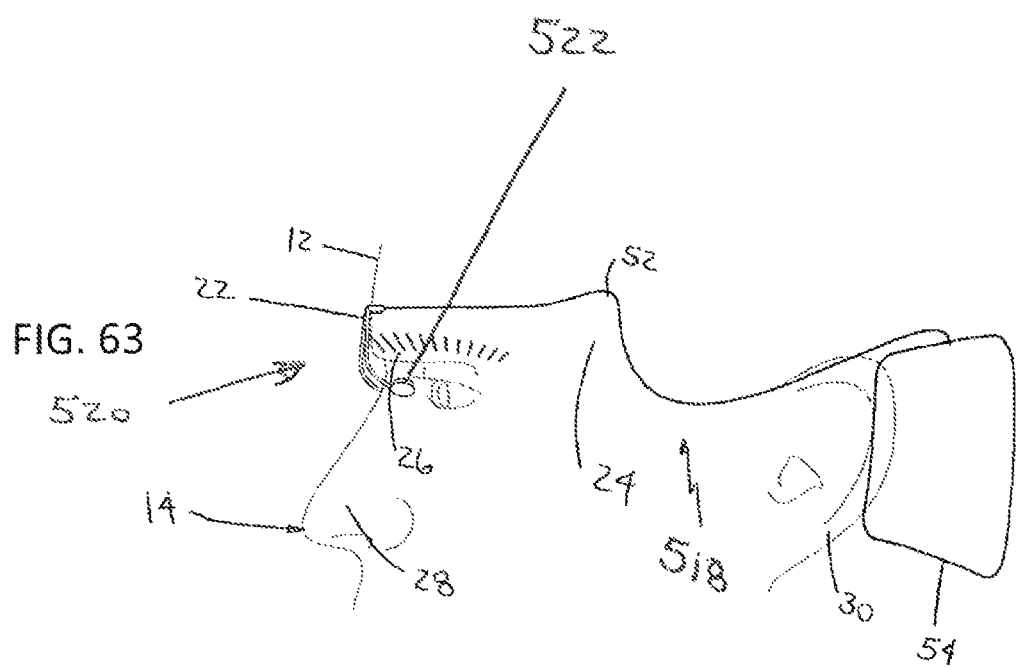
FIG. 63 shows a view of a thirty-sixth apparatus in accordance with an exemplary embodiment of the present disclosure.

FIG. 63 is the embodiment of FIG. 7 modified to include a dual sensor assembly 520 having a pair of non-contact sensors 522. Only left sensor 522 is shown.

Figure 64:
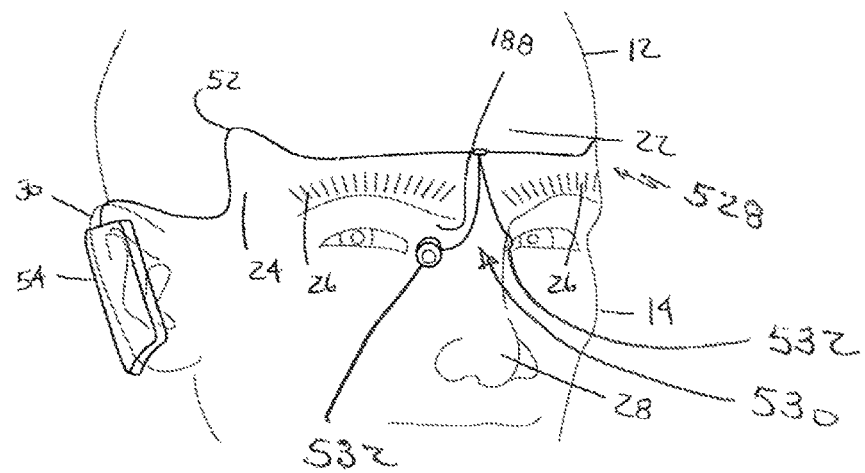
FIG. 64 shows a view of a thirty-seventh apparatus in accordance with an exemplary embodiment of the present disclosure.

FIG. 64 is the embodiment of FIG. 9 modified as a sensing frame 528 to include a dual sensor assembly 530 having a pair of non-contact sensors 532, showing right sensor 532 and left sensor 532.

Figure 65:
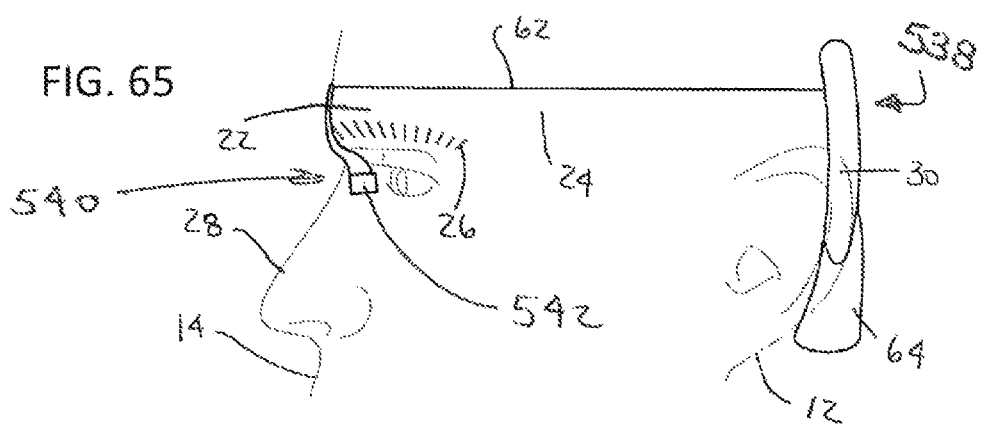
FIG. 65 shows a view of a thirty-eighth apparatus in accordance with an exemplary embodiment of the present disclosure.

FIG. 65 is the embodiment of FIG. 10 modified as a therapeutic frame 538 to include a temperature modification assembly 540 having temperature modification device 542, such as a Peltier device, a thermoelectric device, a resistive device (resistor-based heating device), and the like.

Figure 66:
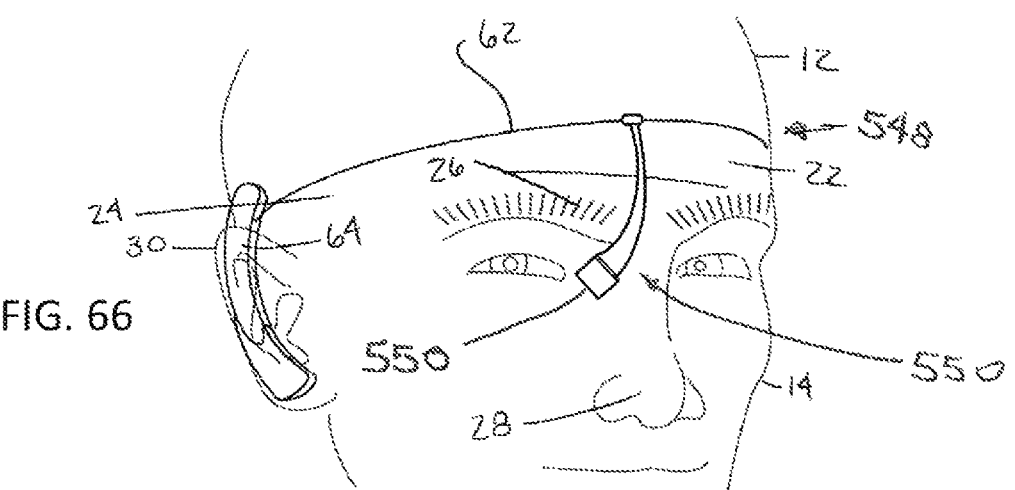
FIG. 66 shows a view of a thirty-ninth apparatus in accordance with an exemplary embodiment of the present disclosure.

FIG. 66 is the embodiment of FIG. 12 modified as a therapeutic frame 548 to include a temperature modification assembly 550 having a temperature modification device 542, such as a Peltier device, a thermoelectric device, a resistive device (resistor-based heating device), and the like.

Figure 67:
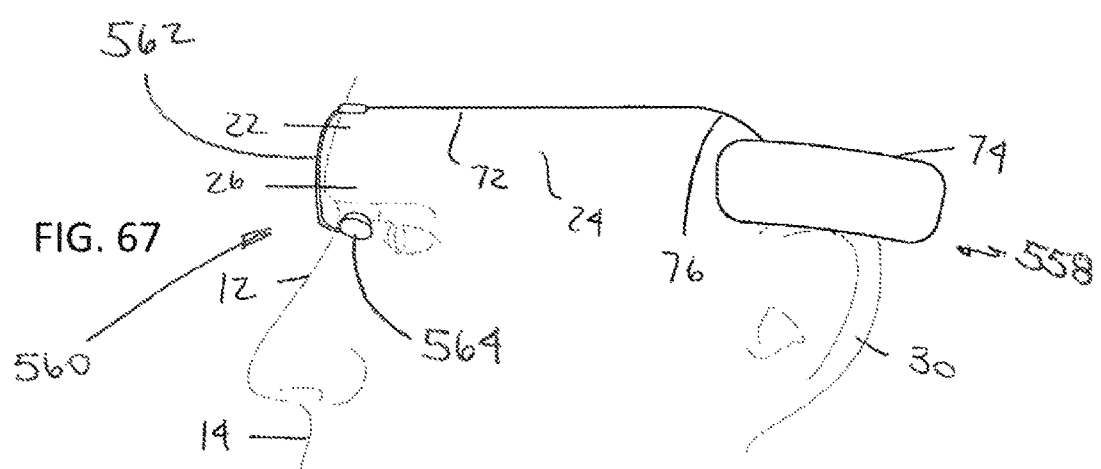
FIG. 67 shows a view of a fortieth apparatus in accordance with an exemplary embodiment of the present disclosure.

FIG. 67 is the embodiment of FIG. 13 modified as a sensing frame 558 to include a sensor assembly 560 having an arm 562 and a contact sensor 564, arm 562 being connected to wire portion 72.

Figure 68:
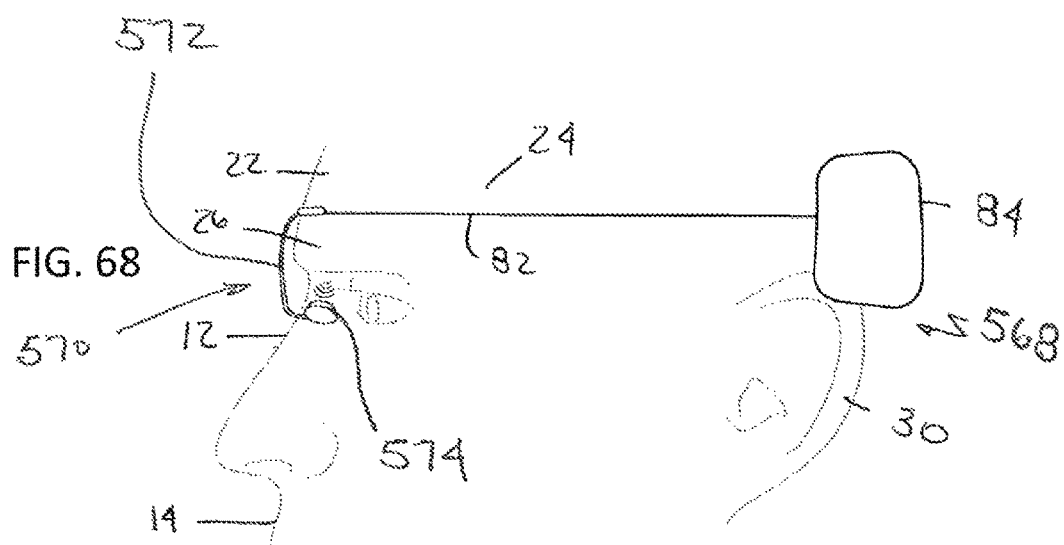
FIG. 68 shows a view of a forty-first apparatus in accordance with an exemplary embodiment of the present disclosure.

FIG. 68 is the embodiment of FIG. 14 modified as a sensing frame 568 to include a non-contact sensor assembly 570 having an arm 572 and a non-contact sensor 574, arm 572 being connected to wire portion 82.

Figure 69:
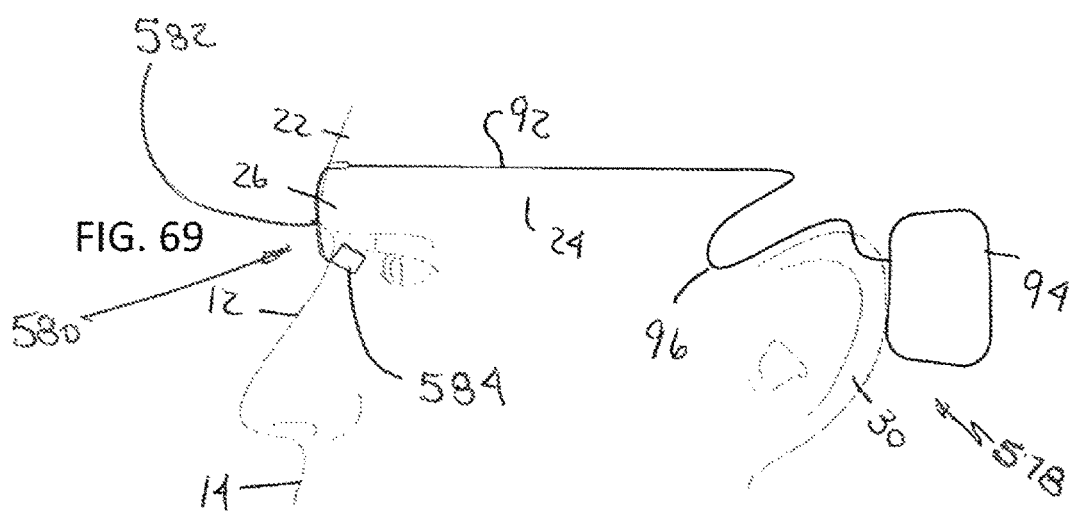
FIG. 69 shows a view of a forty-second apparatus in accordance with an exemplary embodiment of the present disclosure.

FIG. 69 is the embodiment of FIG. 15 modified as a therapeutic frame 578 to include a temperature modification assembly 580 having an arm 582 and a temperature modification device 584, arm 582 being connected to wire portion 92.

Figure 70:
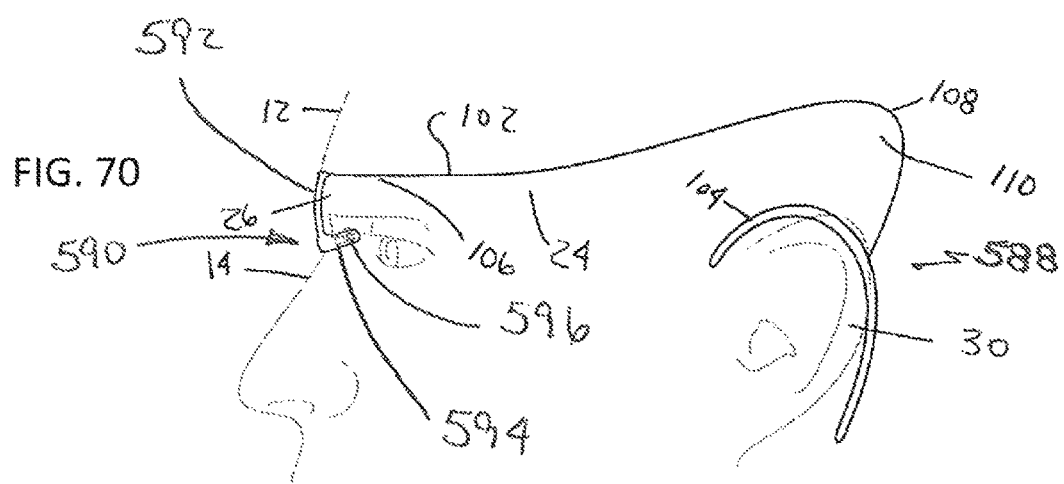
FIG. 70 shows a view of a forty-third apparatus in accordance with an exemplary embodiment of the present disclosure.

FIG. 70 is the embodiment of FIG. 16 modified as a sensing frame 588 to include an emitter-detector assembly 590 having an arm 592 and an emitter 594 and a detector 596, arm 592 being connected to wire portion 102.

Figure 71:
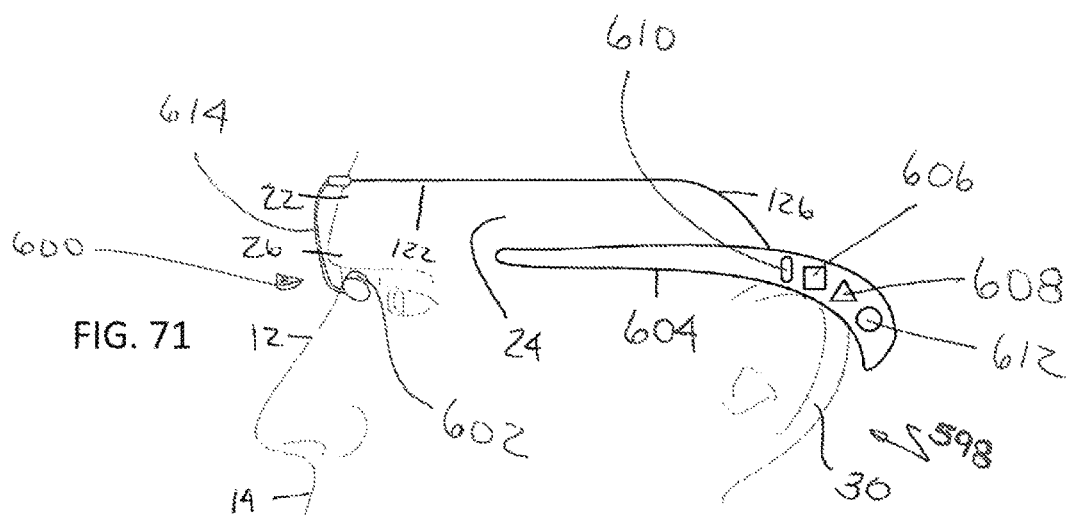
FIG. 71 shows a view of a forty-fourth apparatus in accordance with an exemplary embodiment of the present disclosure.

FIG. 71 is the embodiment of FIG. 17 modified as a sensing frame 598 to include a sensor assembly 600 having a sensor 602. Device 124 is replaced by a housing 604, and housing 604 includes a processor 606, a transmitter 608, a non-transitory memory 610, and a power source 612. Sensor 602 is connected to wire frame portion by an arm 614. In this manner, the hardware of apparatus 120, which can be described as a sensing frame when configured with sensor assembly 600, is located away from a front portion of the sensing frame, being thereby more cosmetically attractive and avoiding conflict with conventional eyewear being used by a user.

Figure 72:
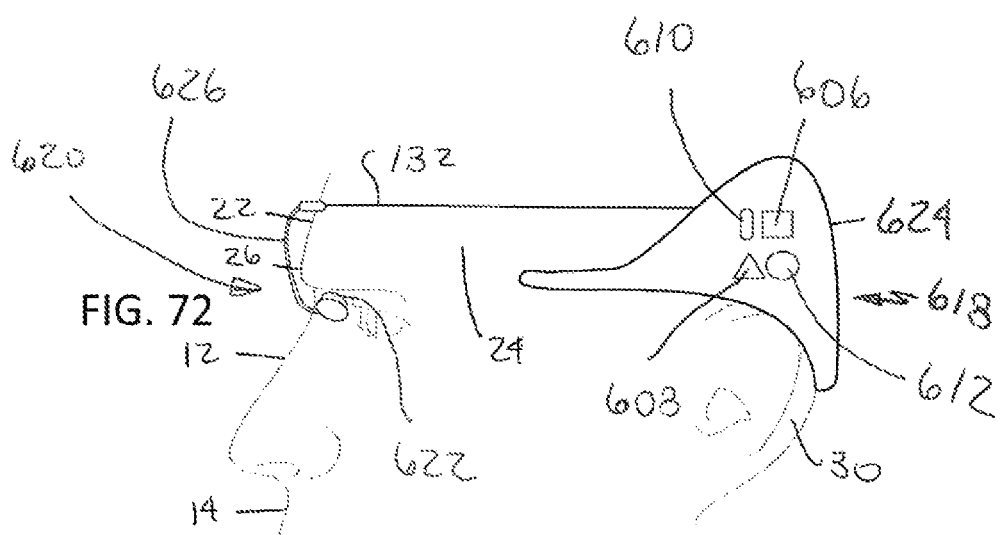
FIG. 72 shows a view of a forty-fifth apparatus in accordance with an exemplary embodiment of the present disclosure.

FIG. 72 is the embodiment of FIG. 18 modified as a sensing frame 618 to include a sensor assembly 620 having a sensor 622. Device 134 is replaced with a housing 624, and housing 624 includes processor 606, transmitter 608, non-transitory memory 610, and power source 612. Sensor 622 is connected to wire frame portion 132 by an arm 626. In this manner, the hardware of apparatus 130, which can be described as a sensing frame when configured with sensor assembly 620, is located away from a front portion of the sensing frame, being thereby more cosmetically attractive and avoiding conflict with conventional eyewear being used by a user.

Figure 73:
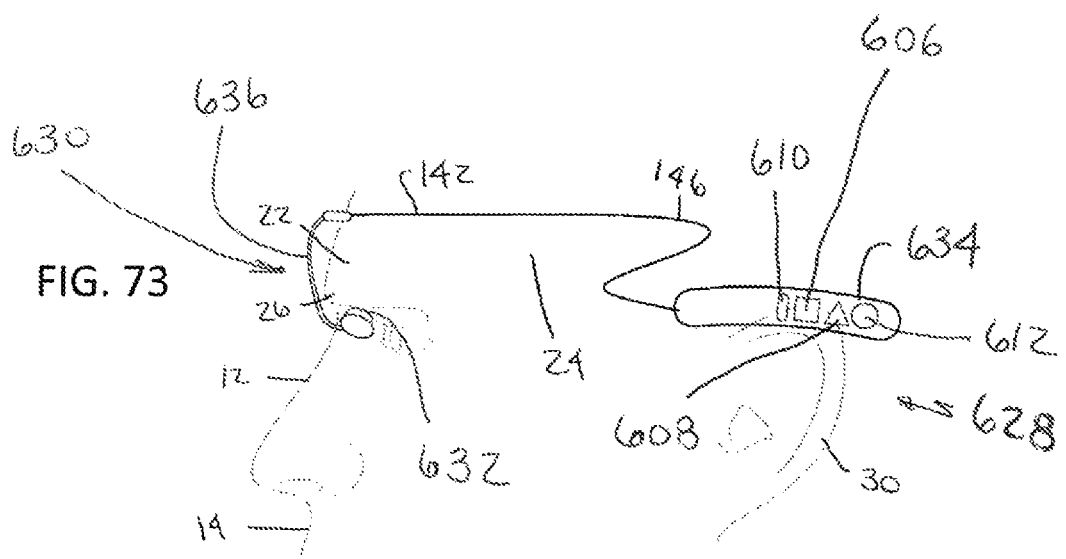
FIG. 73 shows a view of a forty-sixth apparatus in accordance with an exemplary embodiment of the present disclosure.

FIG. 73 is the embodiment of FIG. 19 modified as a sensing frame 628 to include a sensor assembly 630 having a sensor 632. Device 144 is replaced by a housing 634 and housing 634 includes processor 606, transmitter 608, non-transitory memory 610, and power source 612. Sensor 632 is connected to wire frame portion 142 by an arm 636. In this manner, the hardware of apparatus 140, which can be described as a sensing frame when configured with sensor assembly 630, is located away from a front portion of the sensing frame, being thereby more cosmetically attractive and avoiding conflict with conventional eyewear being used by a user.

Figure 74:
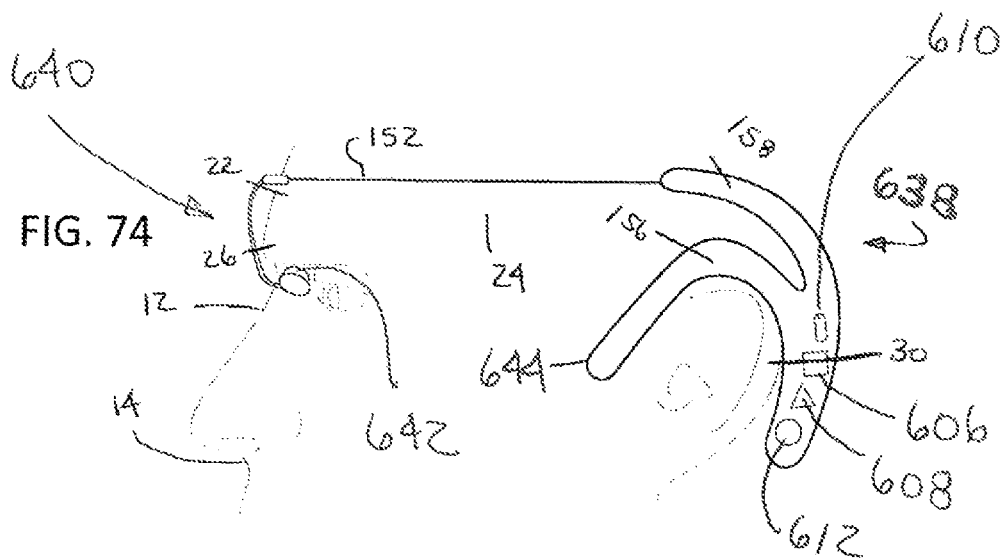
FIG. 74 shows a view of a forty-seventh apparatus in accordance with an exemplary embodiment of the present disclosure.

FIG. 74 is the embodiment of FIG. 20 modified as a sensing frame 638 to include a sensor assembly 640 having a sensor 642. Device 154 is replaced by a housing 644, and housing 644 includes processor 606, a transmitter 608, non-transitory memory 610, and power source 612. Sensor 642 is connected to wire frame portion 152 by an arm 646. In this manner, the hardware of apparatus 150, which can be described as a sensing frame when configured with sensor assembly 640, is located away from a front portion of the sensing frame, being thereby more cosmetically attractive and avoiding conflict with conventional eyewear being used by a user.

Figure 75:
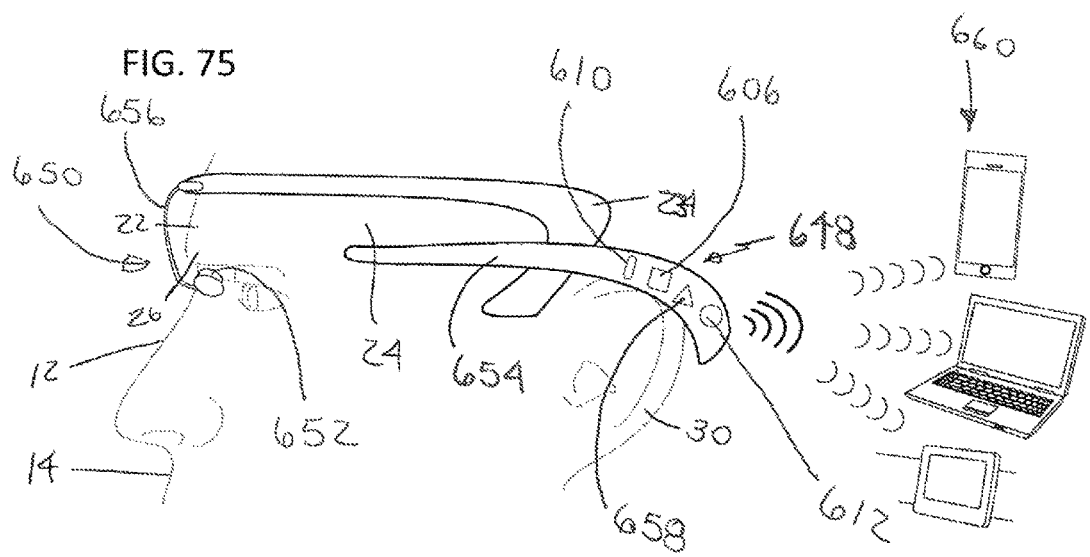
FIG. 75 shows a view of a forty-eighth apparatus in accordance with an exemplary embodiment of the present disclosure.

FIG. 75 is the embodiment of FIG. 30 modified as a sensing frame 648 to include a sensor assembly 650 having a sensor 652. First support 232 is replaced by a housing 654, and housing 654 includes processor 606, a transmitter or transceiver 658, non-transitory memory 610, and power source 612. Sensor 652 is connected to second support 234 an arm 656. Sensor assembly 650 communicates with a remote device 660 by way of a wireless signal transmitted by transmitter or transceiver 658. Remote device 660 can be, for example, a cell phone, a telephone, watch, computer, and the like.

Figure 76:
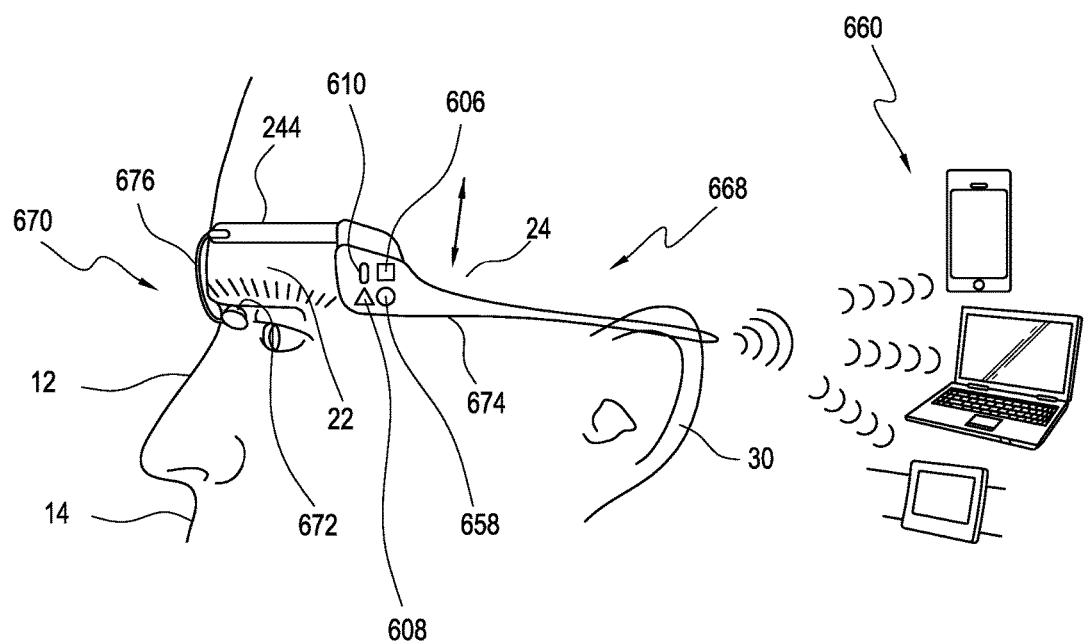
FIG. 76 shows a view of a forty-ninth apparatus in accordance with an exemplary embodiment of the present disclosure.

FIG. 76 is the embodiment of FIG. 31 modified as a sensing frame 668 to include a non-contact sensor assembly 670 having a non-contact sensor 672. First support 242 is replaced by a housing 674, and housing 674 includes processor 606, transmitter or transceiver 658, non-transitory memory 610, and power source 612. Sensor 672 is connected to second support 244 by an arm 676. Sensor assembly 670 communicates with remote device 660 by way of a wireless signal transmitted by transmitter or transceiver 658. Remote device 660 can be, for example, a cell phone, a telephone, watch, computer, and the like.

Figure 77:
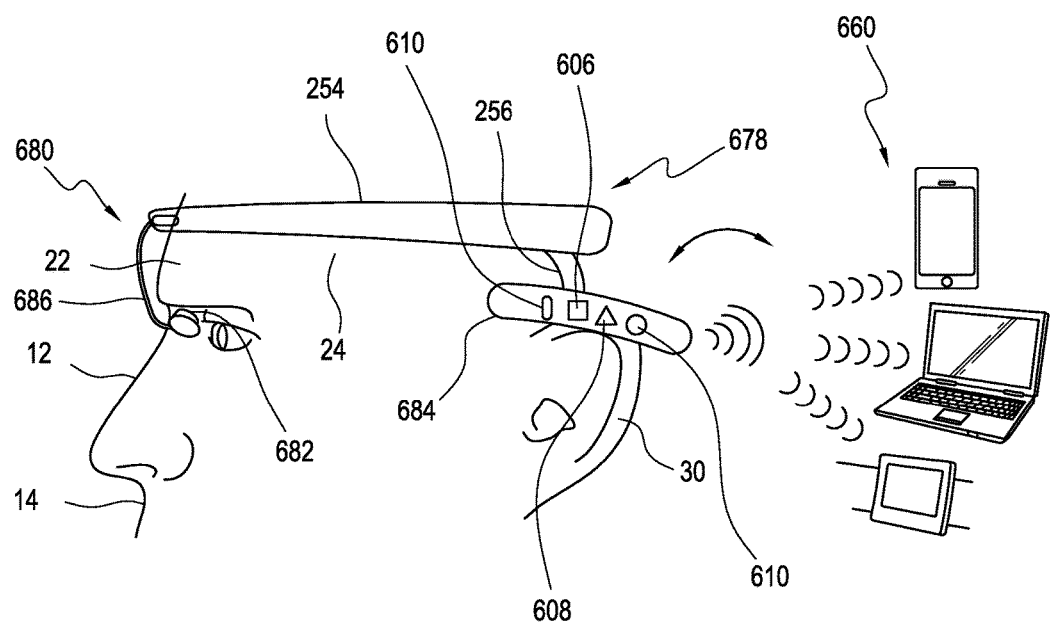
FIG. 77 shows a view of a fiftieth apparatus in accordance with an exemplary embodiment of the present disclosure.

FIG. 77 is the embodiment of FIG. 32 modified as a sensing frame 678 to include a temperature modification assembly 680 having a temperature modification device 682. First support 252 is replaced by a housing 684, and housing 684 includes processor 606, transmitter or transceiver 658, non-transitory memory 610, and power source 612. Temperature modification device 682 is connected to second support 254 by an arm 686. Temperature modification assembly 680 communicates with remote device 660 by way of a wireless signal transmitted by transmitter or transceiver 658. Remote device 660 can be, for example, a cell phone, a telephone, watch, computer, and the like.

Figure 78:
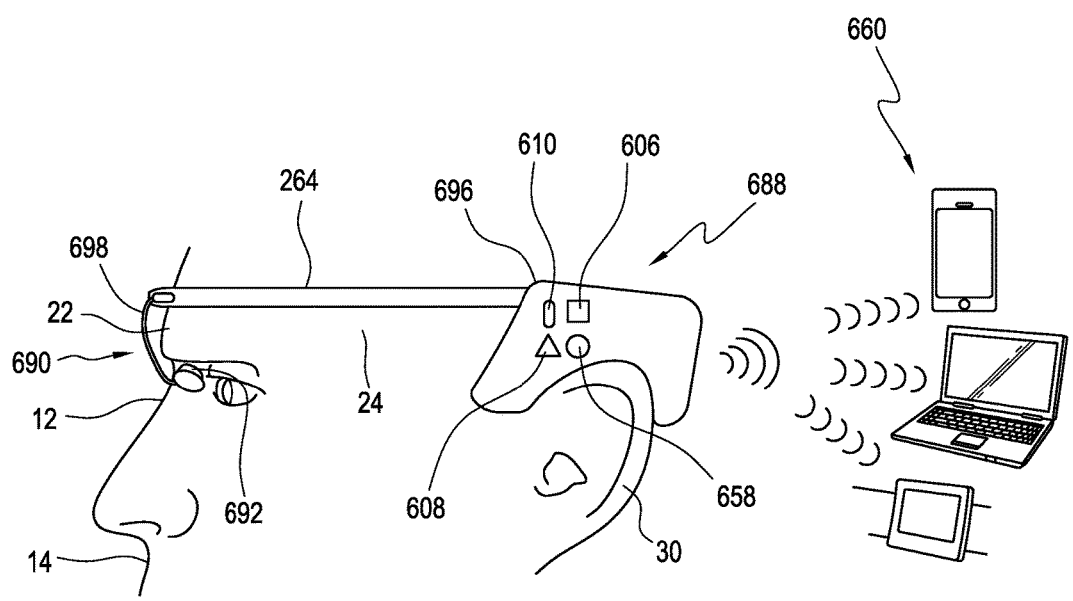
FIG. 78 shows a view of a fifty-first apparatus in accordance with an exemplary embodiment of the present disclosure.

FIG. 78 is the embodiment of FIG. 33 modified as a sensing frame 688 to include a temperature modification assembly 690 including a temperature modification device 692. First support 262 is replaced by a housing 696, and housing 696 includes processor 606, transmitter or transceiver 658, non-transitory memory 610, and power source 612. Temperature modification device 692 is connected to second support 264 by an arm 698. Temperature modification assembly 690 communicates with remote device 660 by way of a wireless signal transmitted by transmitter or transceiver 658. Remote device 660 can be, for example, a cell phone, a telephone, watch, computer, and the like.

Figure 79:
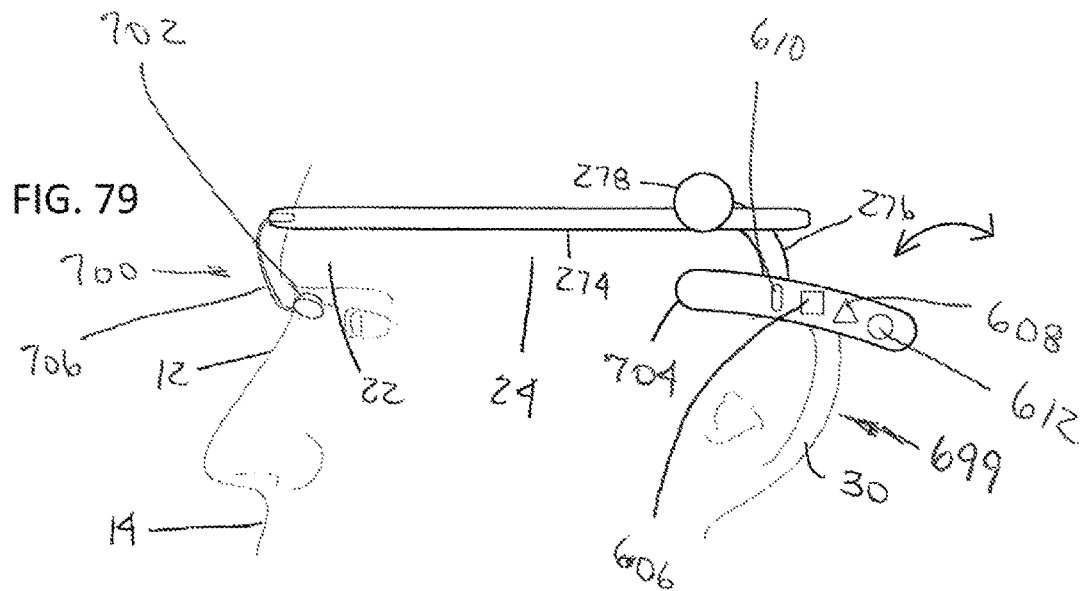
FIG. 79 shows a view of a fifty-second apparatus in accordance with an exemplary embodiment of the present disclosure.

FIG. 79 is the embodiment of FIG. 34 modified as a sensing frame 699 to include a sensor assembly 700 having a sensor 702. First support 272 is replaced by a housing 704, and housing 704 includes processor 606, transmitter 608, non-transitory memory 610, and power source 612. Sensor 702 is connected to second support 274 by an arm 706.

Figure 80:
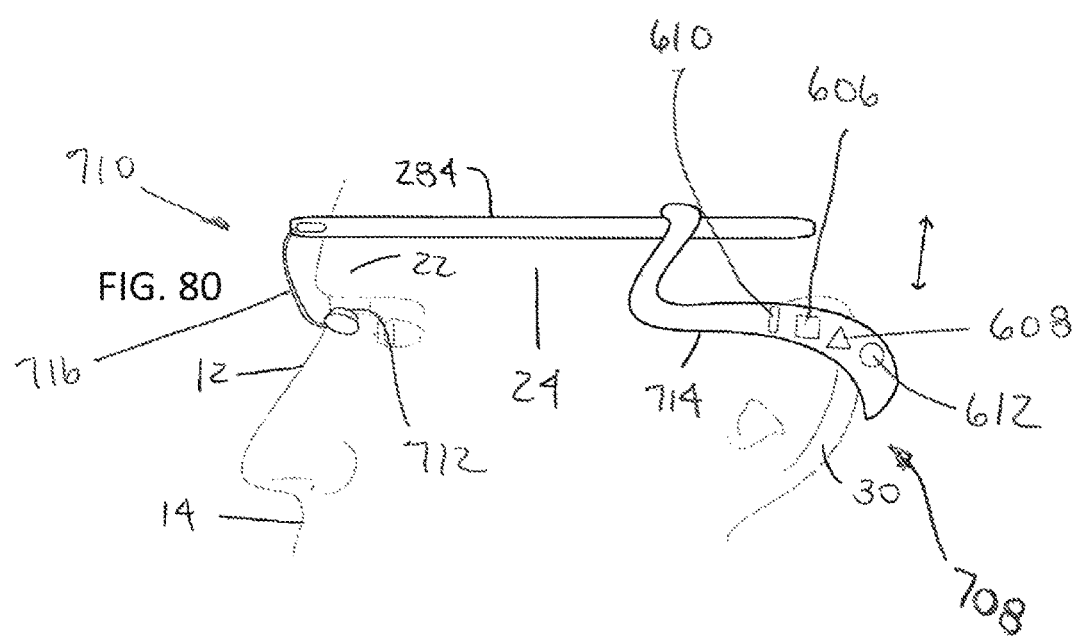
FIG. 80 shows a view of a fifty-third apparatus in accordance with an exemplary embodiment of the present disclosure.

FIG. 80 is the embodiment of FIG. 35 modified as a sensing frame 708 to include a sensor assembly 710 having a sensor 712. First support 282 is replaced by a housing 714. Housing 714 includes processor 606, transmitter 608, non-transitory memory 610, and power source 612. Sensor 712 is connected to second support 284 by an arm 716.

Figure 81:
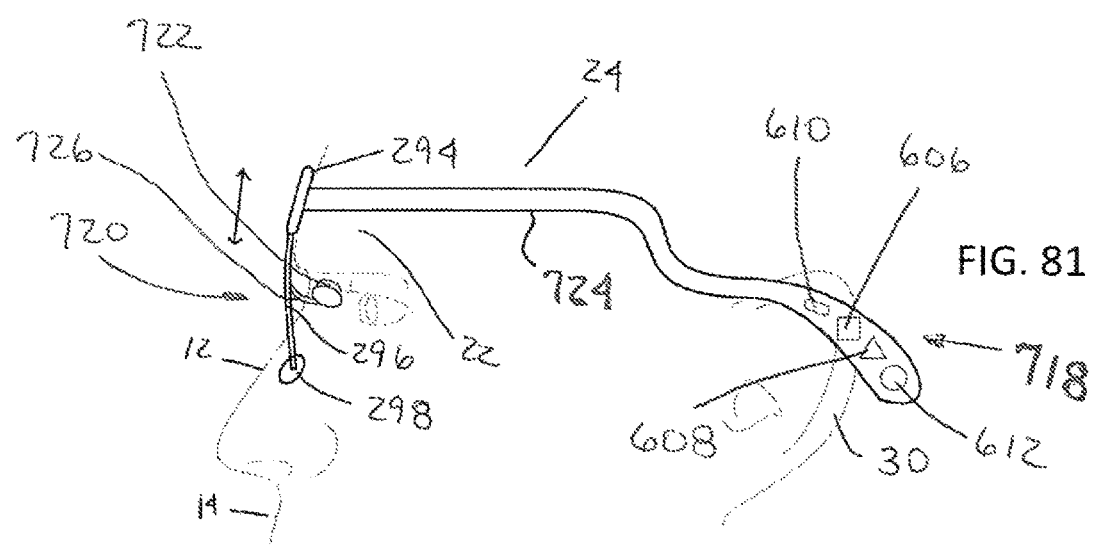
FIG. 81 shows a view of a fifty-fourth apparatus in accordance with an exemplary embodiment of the present disclosure.

FIG. 81 is the embodiment of FIG. 36 modified as a sensing frame 718 to include a sensor assembly 720 having a sensor 722. First support 292 is replaced by a housing 724. Housing 724 includes processor 606, transmitter 608, non-transitory memory 610, and power source 612. Sensor 722 is connected to second support 294 by an arm 726.

Figure 82:
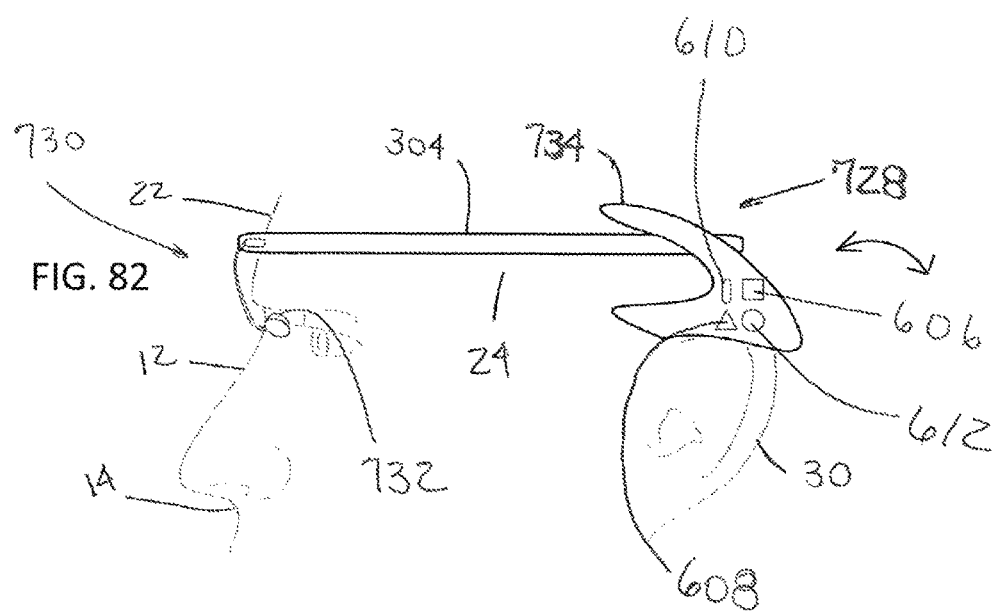
FIG. 82 shows a view of a fifty-fifth apparatus in accordance with an exemplary embodiment of the present disclosure.

FIG. 82 is the embodiment of FIG. 37 modified as a sensing frame 728 to include a sensor assembly 730 having a sensor 732. First support 302 is replaced by a housing 734. Housing 734 includes processor 606, transmitter 608, non-transitory memory 610, and power source 612. Sensor 732 is connected to second support 304 by an arm 736.

Figure 83:
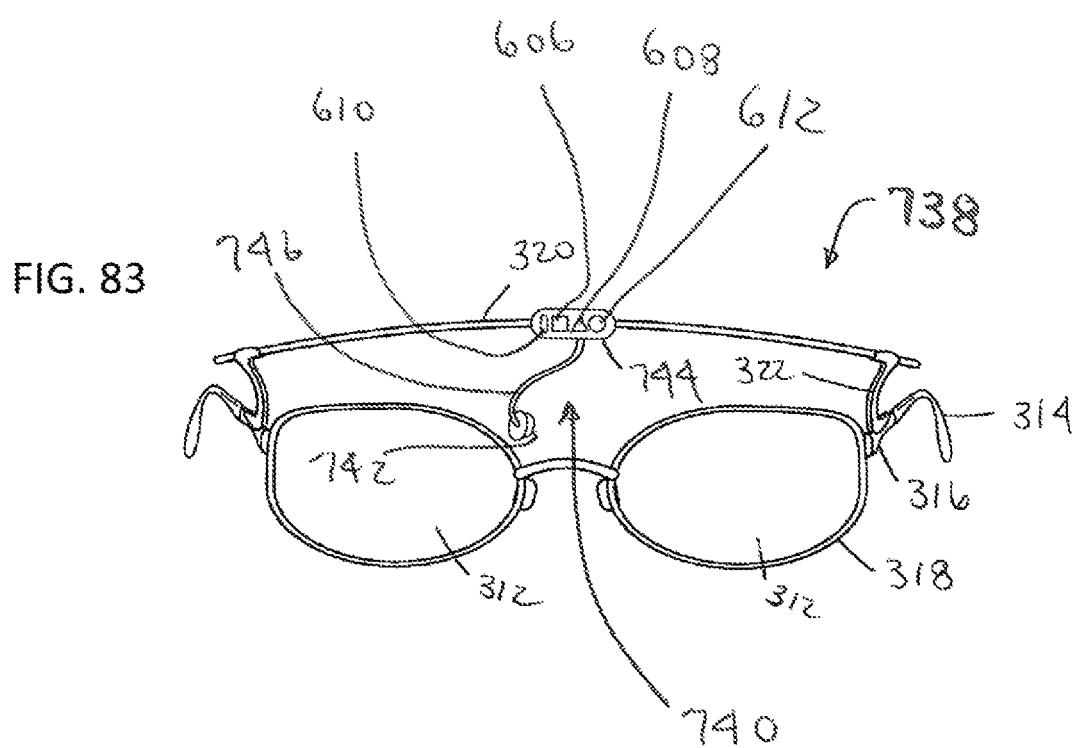
FIG. 83 shows a view of a fifty-sixth apparatus in accordance with an exemplary embodiment of the present disclosure.

FIG. 83 is the embodiment of FIG. 39 modified as a sensing frame 738 to include a sensor assembly 740 having a sensor 742 and a housing 744. Housing 744 includes processor 606, transmitter 608, non-transitory memory 610, and power source 612. Sensor 742 is connected to housing 744 by an arm 746. Housing 744 is supported on second frame support 320.

Figure 84:
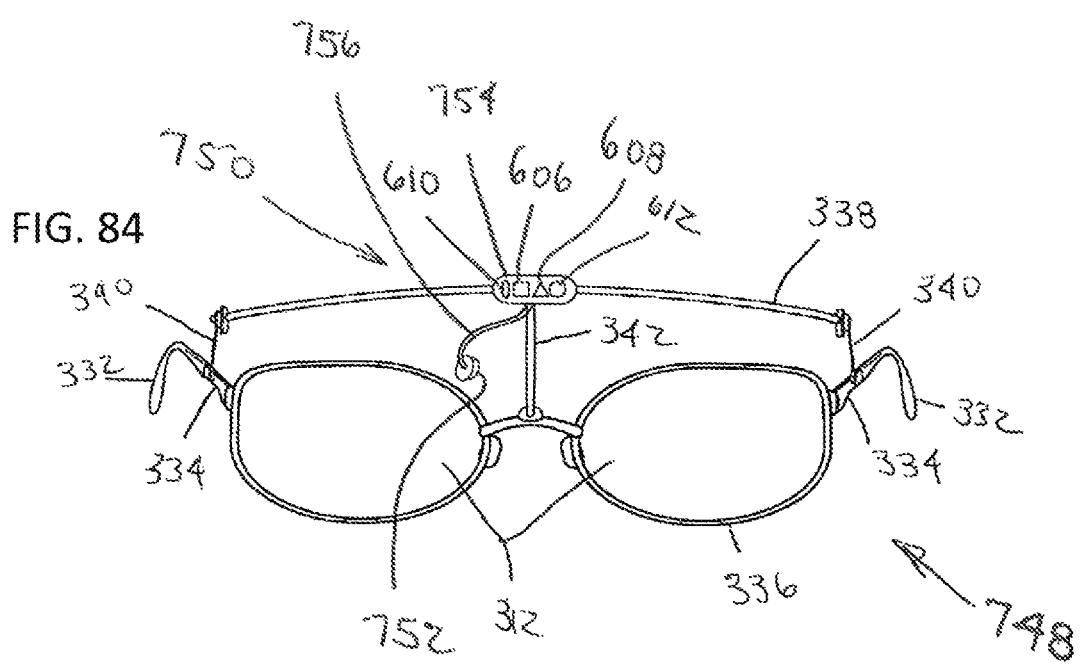
FIG. 84 shows a view of a fifty-seventh apparatus in accordance with an exemplary embodiment of the present disclosure.

FIG. 84 is the embodiment of FIG. 41 modified as a sensing frame 748 to include a sensor assembly 750 having a sensor 752 and at least one housing 754. Housing 754 includes electronics, which can include processor 606, transmitter 608, non-transitory memory 610, and power source 612. Sensor 752 is connected to housing 754 by an arm 756. Housing 754 is supported on second frame support 338.

Figure 85:
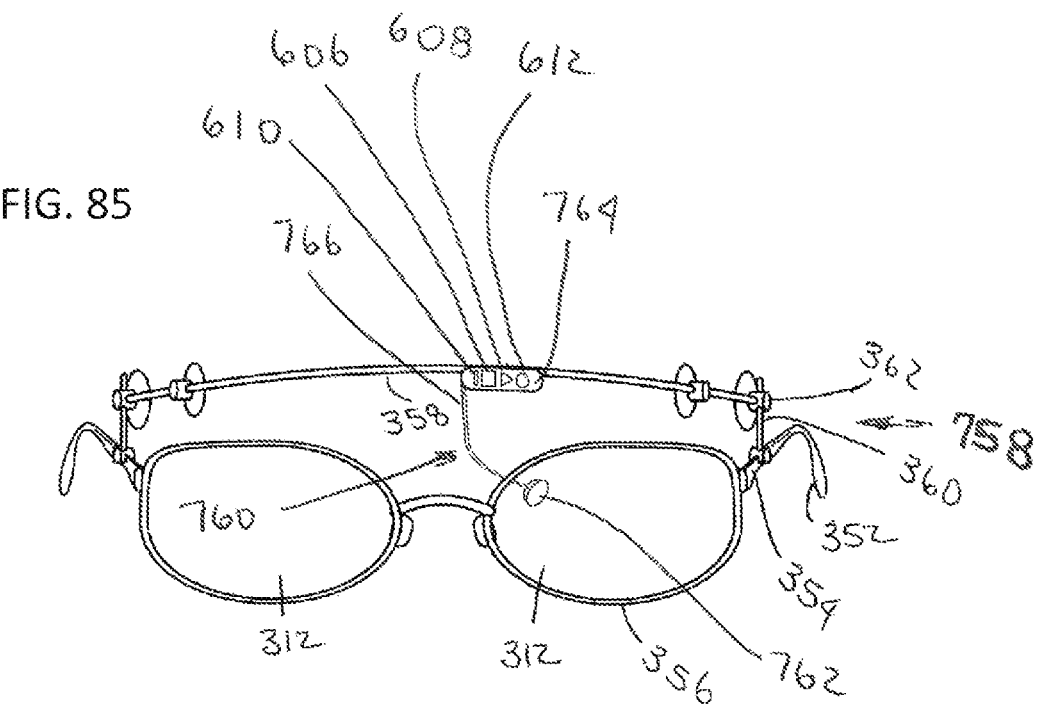
FIG. 85 shows a view of a fifty-eighth apparatus in accordance with an exemplary embodiment of the present disclosure.

FIG. 85 is the embodiment of FIG. 43 modified to include a sensor assembly 760 having a sensor 762 and at least one housing 764. Housing 764 includes electronics, which can include processor 606, transmitter 608, non-transitory memory 610, and power source 612. Sensor 762 is connected to housing 764 by an arm 766. Housing 764 is supported on second frame support 358.

Figure 86:
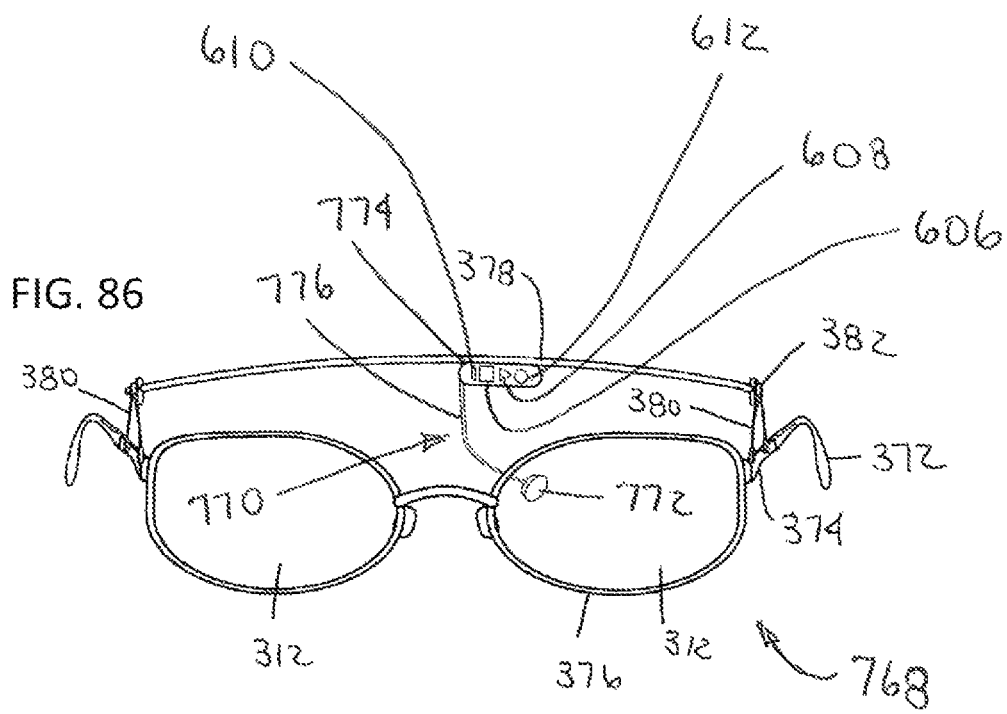
FIG. 86 shows a view of a fifty-ninth apparatus in accordance with an exemplary embodiment of the present disclosure.

FIG. 86 is the embodiment of FIG. 45 modified as a sensing frame 768 to include a sensor assembly 770 having a sensor 772 and at least one housing 774. Housing 774 includes electronics, which can include processor 606, transmitter 608, non-transitory memory 610, and power source 612. Sensor 772 is connected to housing 774 by an arm 776. Housing 774 is supported on second frame support 358.

Figure 47:
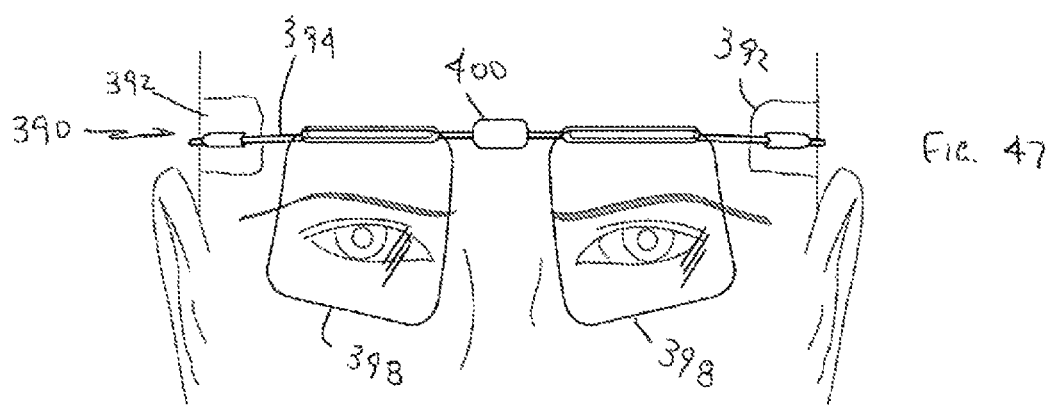
FIG. 47 shows another view of the twenty-sixth apparatus of FIG. 46.
Figure 48:
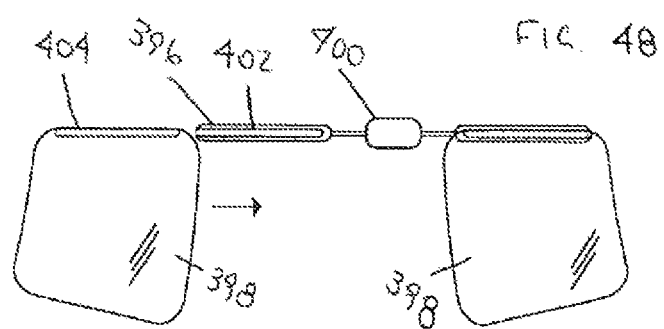
FIG. 48 shows a view of a portion of the twenty-sixth apparatus of FIG. 46.
Figure 49:
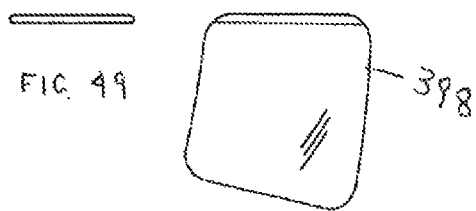
FIG. 49 shows another view of a portion of the twenty-sixth apparatus of FIG. 46.
Figure 87:
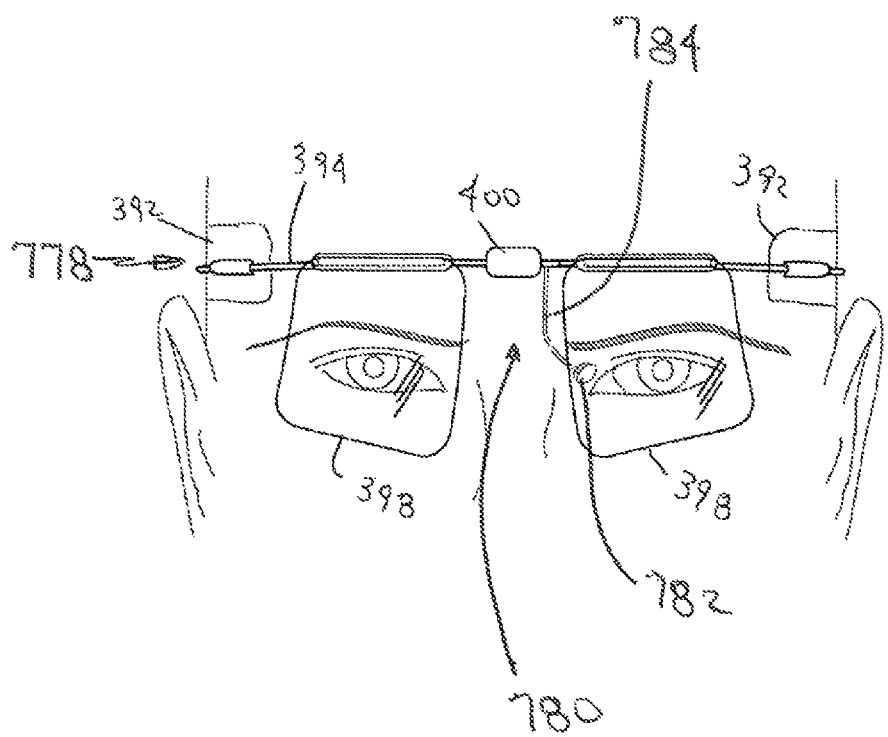
FIG. 87 shows a view of a sixtieth apparatus in accordance with an exemplary embodiment of the present disclosure.

FIG. 87 is the embodiment of FIG. 47 modified as a sensing frame 778 to include a sensor assembly 780 having an arm 784 and a sensor 782, arm 784 connecting sensor 782 to first frame support 394.

Figure 88:
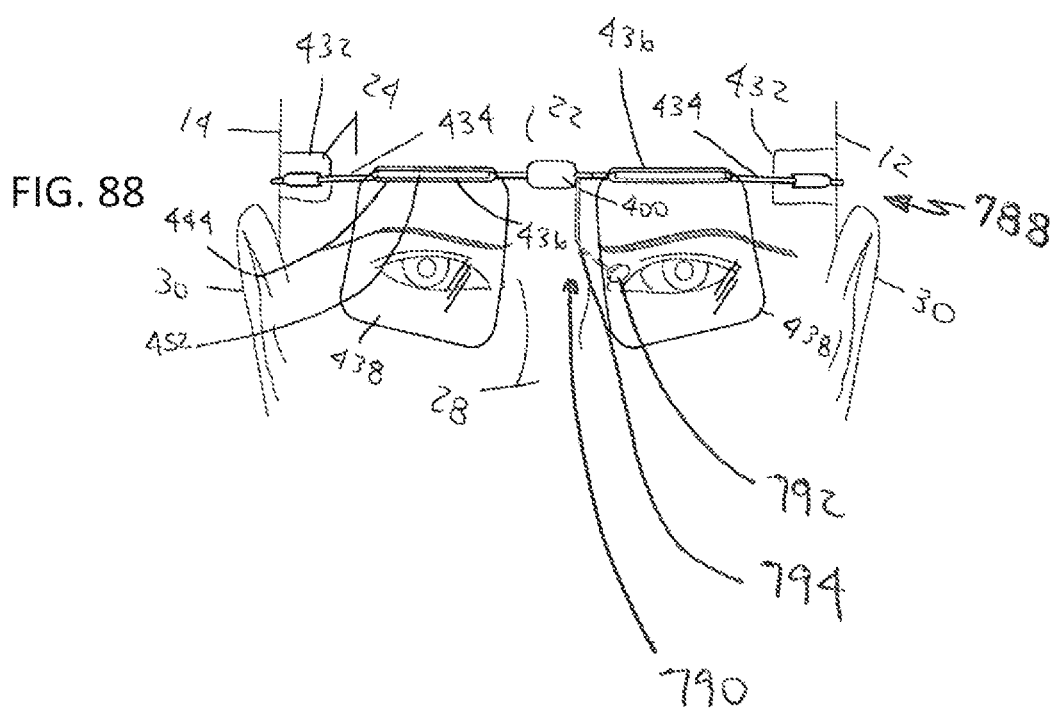
FIG. 88 shows a view of a sixty-first apparatus in accordance with an exemplary embodiment of the present disclosure.

FIG. 88 is the embodiment of FIG. 54 modified as a sensing frame 788 to include a sensor assembly 790 having an arm 794 and a sensor 792, arm 794 connecting sensor 792 to first frame support 434.

Figure 89:
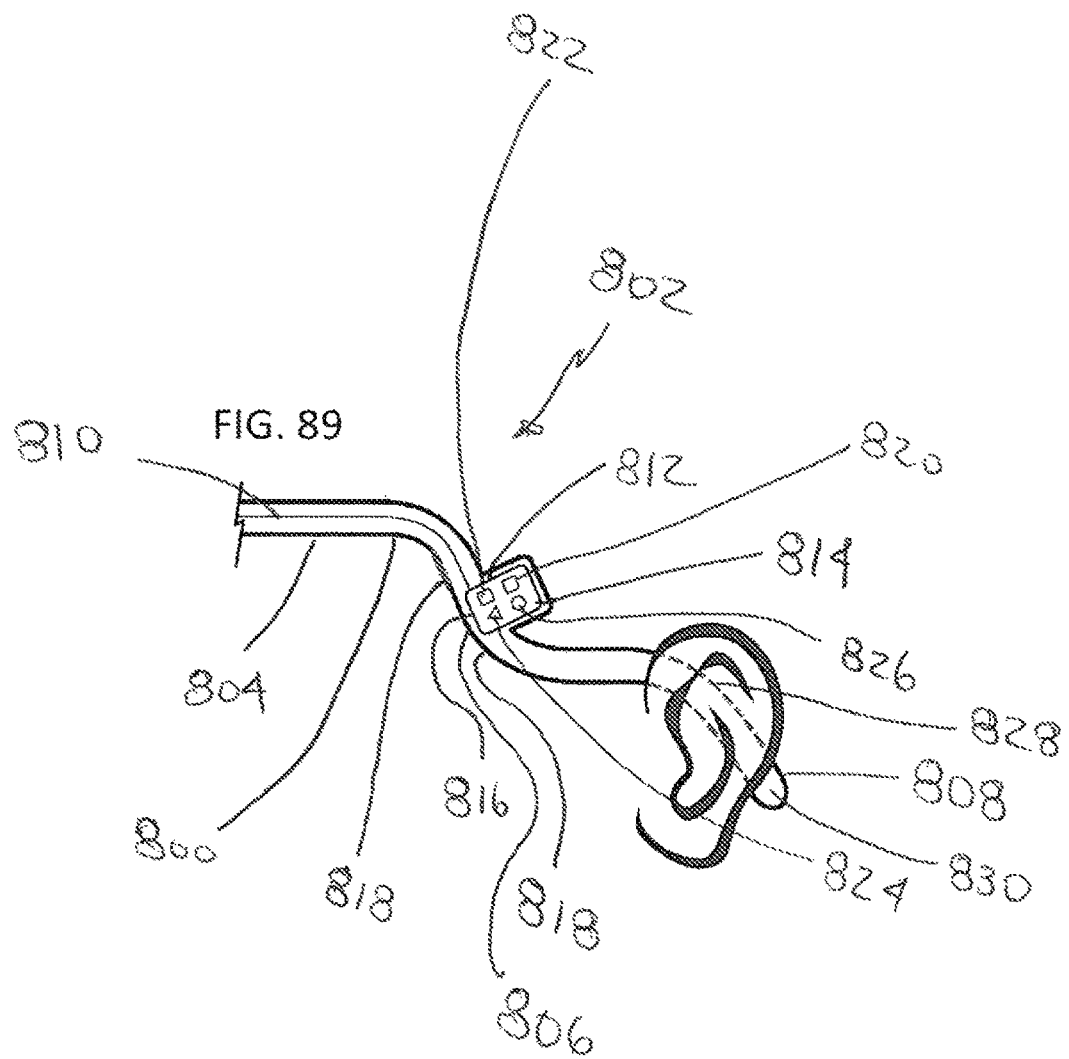
FIG. 89 shows a view of a sixty-second apparatus in accordance with an exemplary embodiment of the present disclosure.

FIG. 89 shows a view of a temple 800 of a sensing frame 802. Temple 800 includes three portions: a first portion 804, a middle portion 860, and a terminal portion 808. First portion 804 is essentially straight, and contains a wire 810 connecting a housing 812 positioned on essentially diagonal middle portion 860 to a sensor (not shown), such as, for example, sensor 298. Housing 812 includes a protruding portion 814 that extends on a superior side in an upward direction, and a flat portion 816 that extends on an inferior side and that accompanies a line 818 of temple frame 800.

Housing 812 includes a processor 820, a non-transitory memory 822, a wireless device 824, and a power source 826. Wire 810 ends in housing 812 and connects to one or more electronic components such as processor 820 in housing 812. Terminal portion 808 has a middle area 828 that is thinner and engages the ear, and a distal area 830 that is larger for anchoring to the head.

Figure 90:
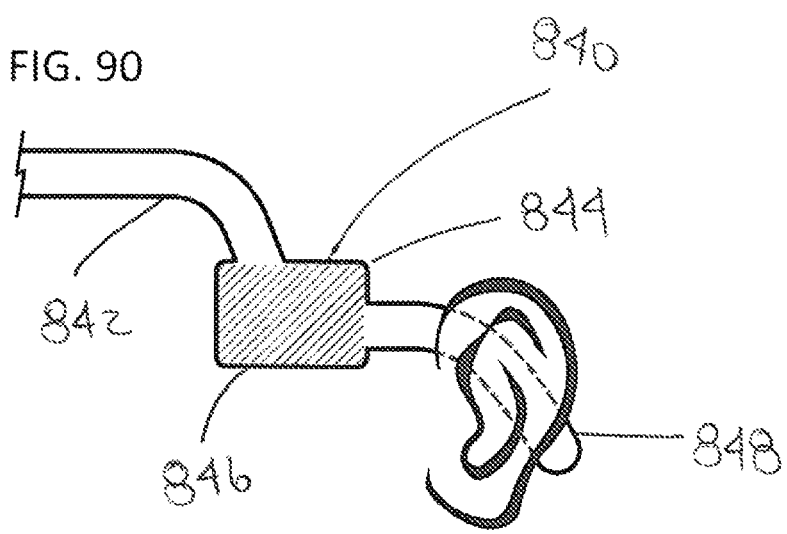
FIG. 90 shows a view of a sixty-third apparatus in accordance with an exemplary embodiment of the present disclosure.

FIG. 90 is an alternative embodiment of FIG. 89, which includes a first housing 840 that overlaps a temple wire or frame 842. First housing 840 includes a first protruding area 844 above temple wire or frame 842 and a second protruding area 846 below temple wire or frame 842, and a second housing 848 at the end of temple wire or frame 842.

Figure 91:
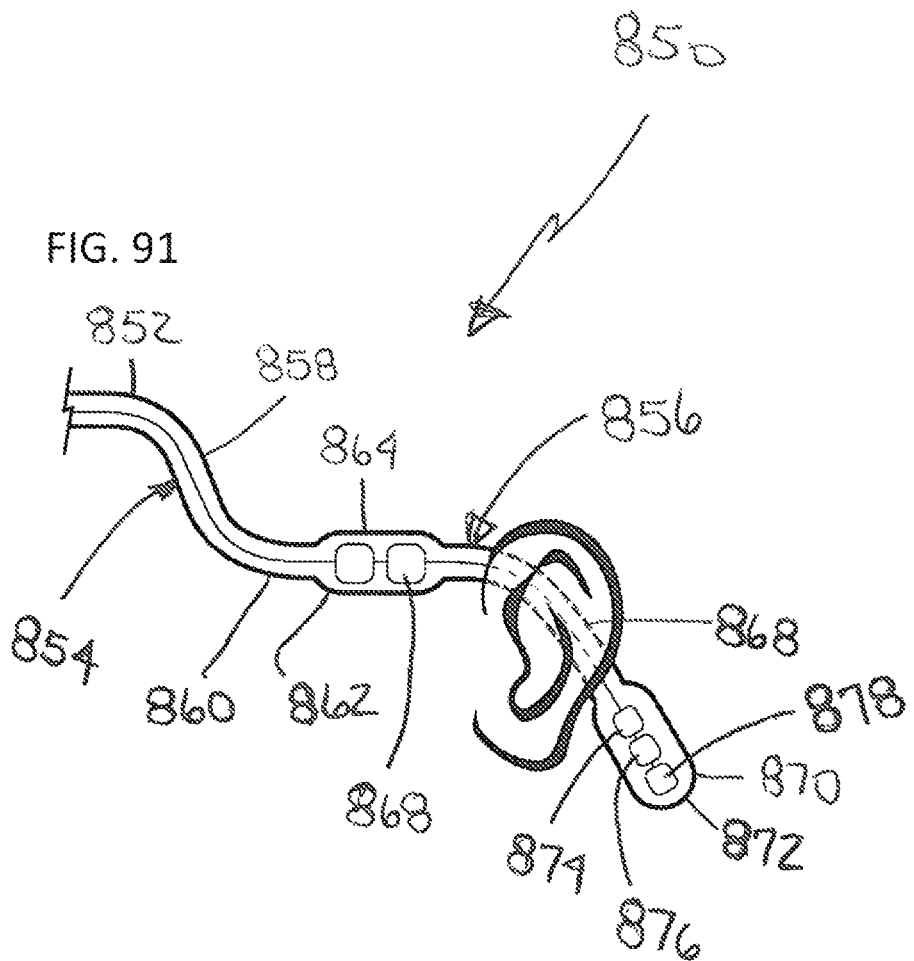
FIG. 91 shows a view of a sixty-fourth apparatus in accordance with an exemplary embodiment of the present disclosure.

FIG. 91 shows a view of a temple 852 of a sensing frame 850. Temple 852 includes two portions: first non-electronic portion 854 and terminal electronic portion 856. First non-electronic portion 854 includes a bent region 858 followed by a straight temple portion 860. Terminal electronic portion 856 includes at least three parts or portions: first part 862 having a first housing 864, first housing 864 including a power source 866; a second part 868 that is smaller in dimension (or thinner) than first part 862; and a third or end part 870. Third or end part 870 includes a second housing 872 in which are positioned or located a processor 874, a non-transitory memory 876, and a transmitter 878.

Figure 92:
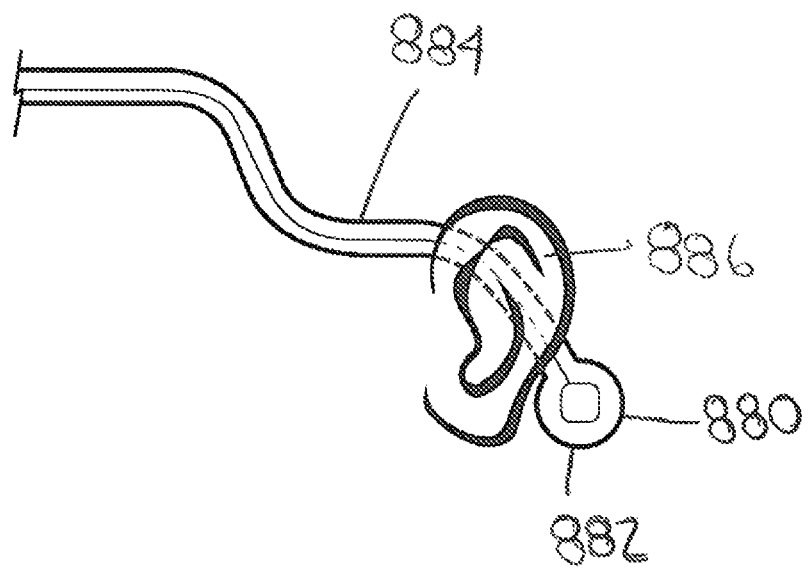
FIG. 92 shows a view of a sixty-fifth apparatus in accordance with an exemplary embodiment of the present disclosure.

FIG. 92 is an alternative embodiment of FIG. 91, but having a protruding part 880 only at a terminal end 882 of a temple frame 884, terminal end 882 engaging with an ear 886.

Figure 93:
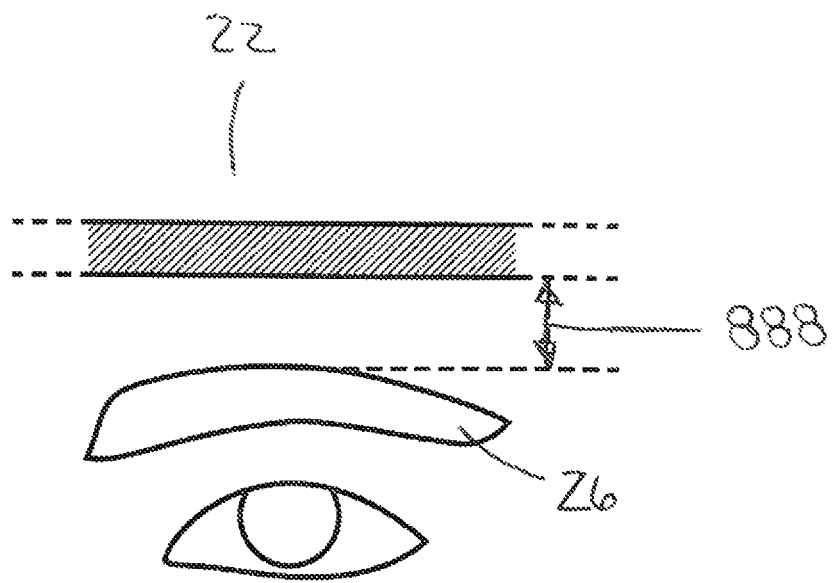
FIG. 93 shows a view of distances of a sensing frame from an eyebrow.

FIG. 93 shows a preferred embodiment of a distance 888 of a forehead support wire, frame, or upper frame to eyebrow 26, which is preferably equal to or less than 10 mm, and more preferably equal to or less than 5 mm, so in this manner, the forehead support wire, frame, or upper frame of the current disclosure is preferably covered by an upper or top portion of conventional frames (not shown).

Figure 94:
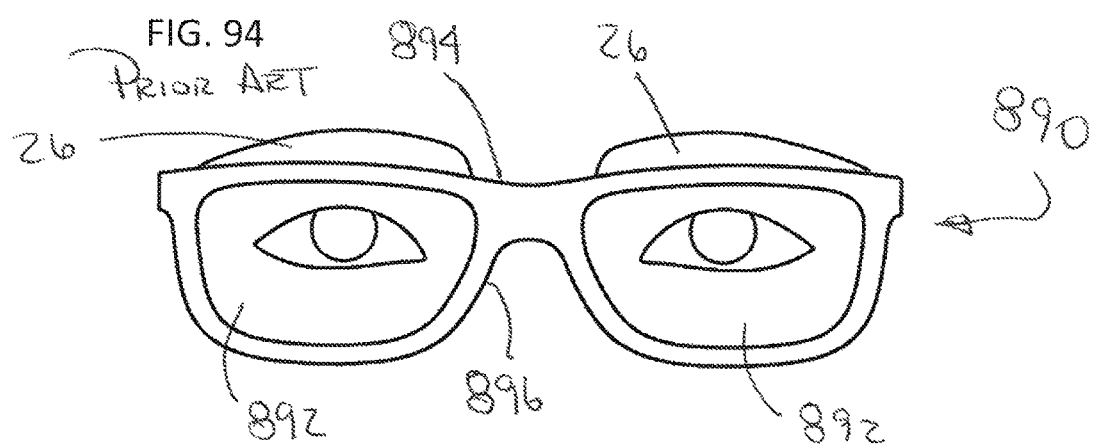
FIG. 94 shows a view of conventional eyeglasses.
Figure 95:
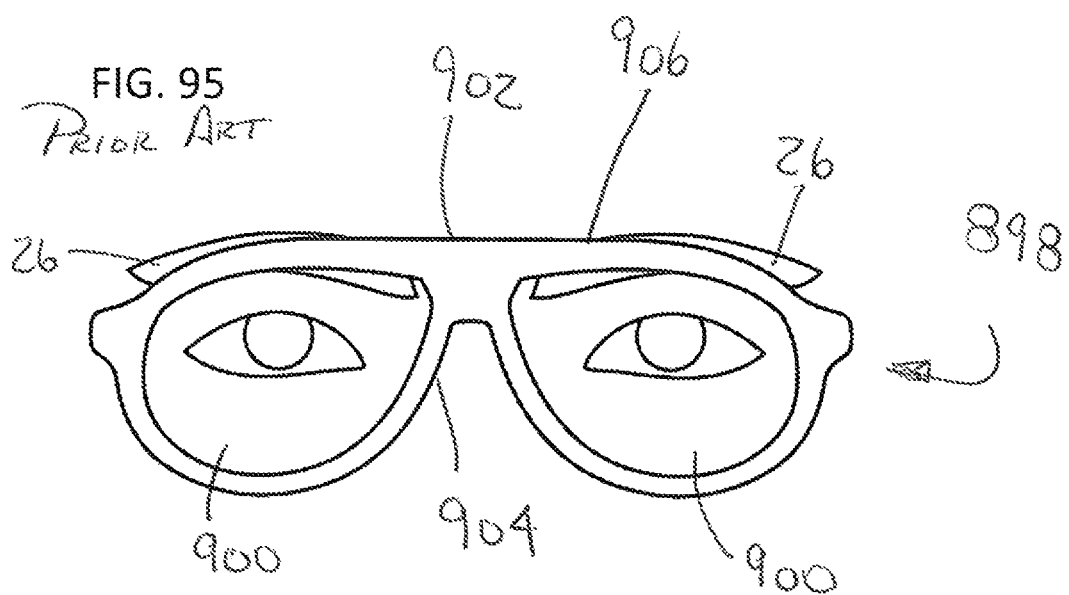
FIG. 95 shows another view of conventional eyeglasses.
Figure 96:
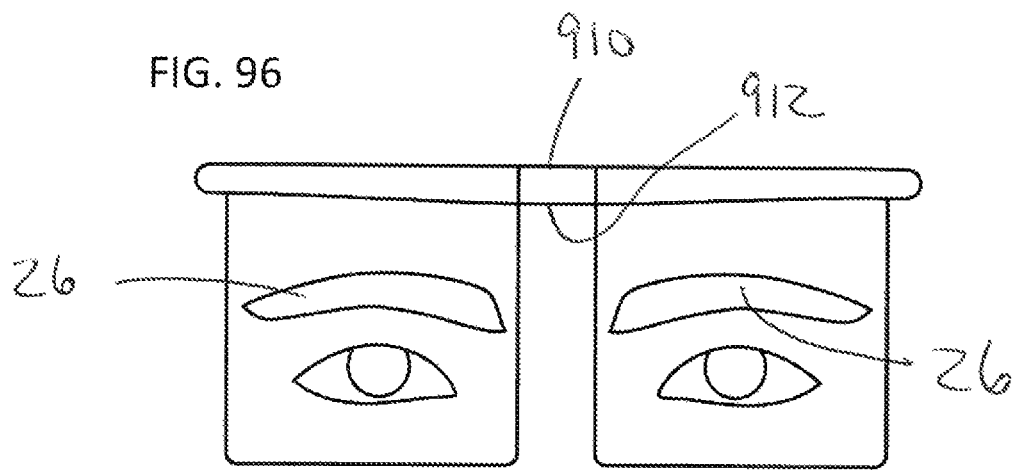
FIG. 96 shows a view of a sixty-sixth apparatus in accordance with an exemplary embodiment of the present disclosure.

FIGS. 94 to 96 show comparisons of a bridge of a nose portion of conventional eyewear with exemplary frames of the present disclosure.

FIG. 94 shows conventional eyewear 890 with conventional lenses 892, and a bridge 894 of a nose portion 896 located below eyebrow 26.

FIG. 95 shows conventional eyewear 898 with large lenses 900, and a bridge 902 of a nose portion 904 located below eyebrow 26, but an upper frame 906 and large lenses 900 being located over eyebrow 26, which may occur in designs of feminine sunglasses, which can have larger lenses.

In contrast to the conventional features of FIGS. 94 and 95, and as shown in FIG. 96, a connecting portion 910 of eyeglasses of present disclosure, including a nose portion 912, are located above eyebrow 26, and preferably between 5 mm to 10 mm above eyebrow 26.

Figure 97:
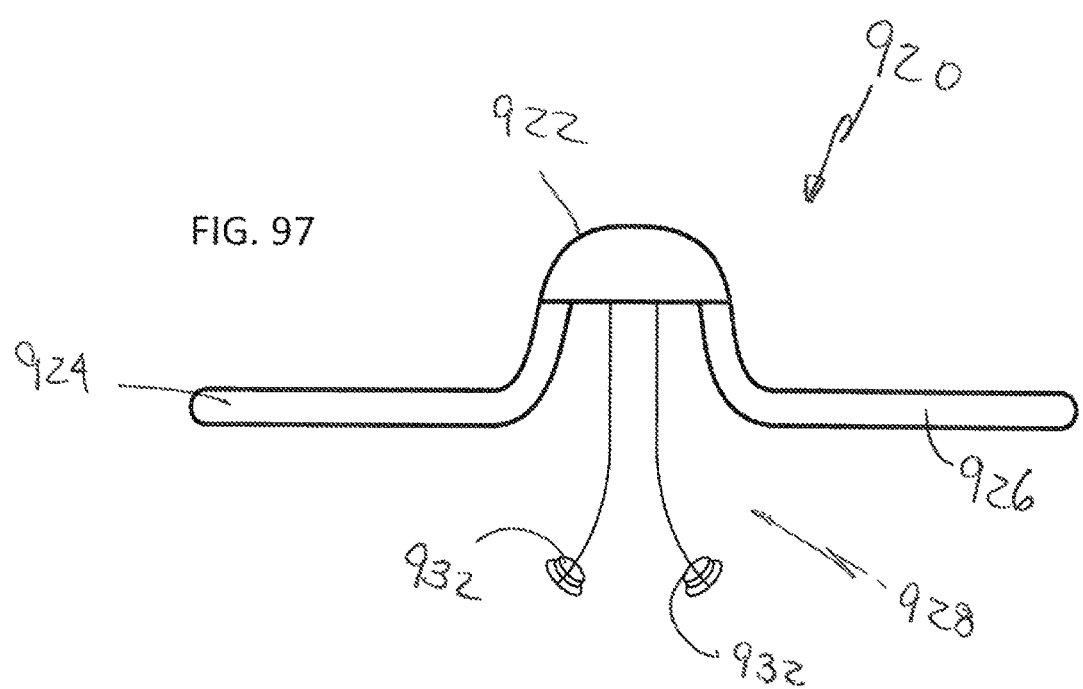
FIG. 97 shows a view of a sixty-seventh apparatus in accordance with an exemplary embodiment of the present disclosure.
Figure 98:
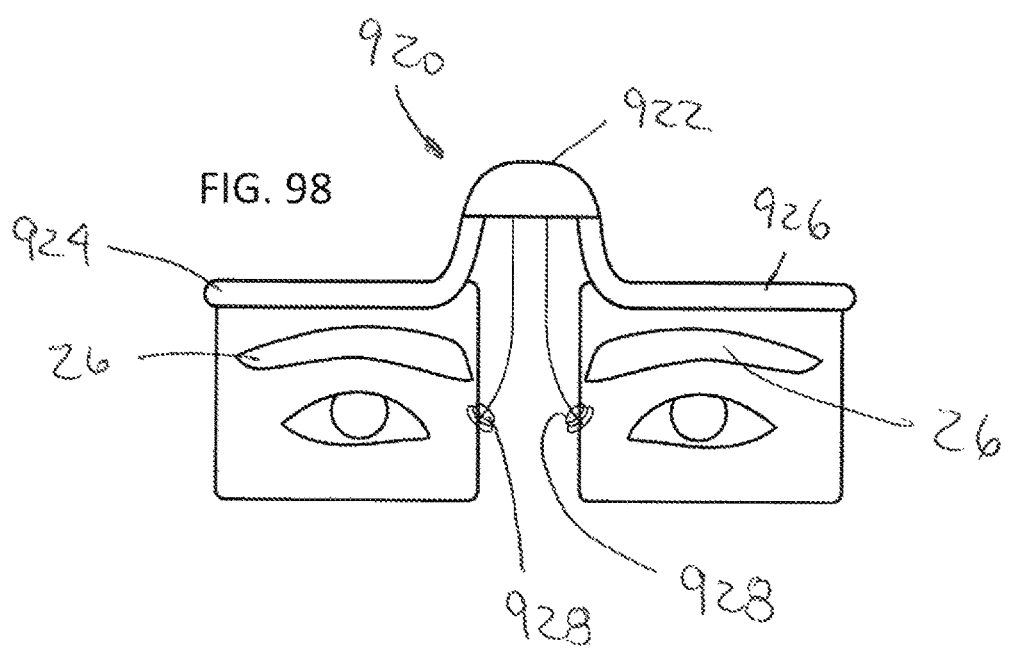
FIG. 98 shows a view of the sixty-eighth apparatus of FIG. 97 used in conjunction with eyeglasses in accordance with an exemplary embodiment of the present disclosure.

FIGS. 97 and 98 show a sensing frame 920, which may also be described as an upper frame, having three portions: a right side portion 924, a left side portion 926, and a central portion or nose area 922. Right side portion 924 and left side portion 926 are located at a same level and are on or adjacent to eyebrows 26. Central portion 922 is high and located above right side portion 924 and left side portion 926, while right side portion 924 and left side portion 926 are displaced inferiorly, and are aligned with eyebrows 26. Central portion 922 includes a sensor assembly 928 having sensor 932 and arms 934, arms 934 being connected to central portion or nose area 922.

Figure 99:
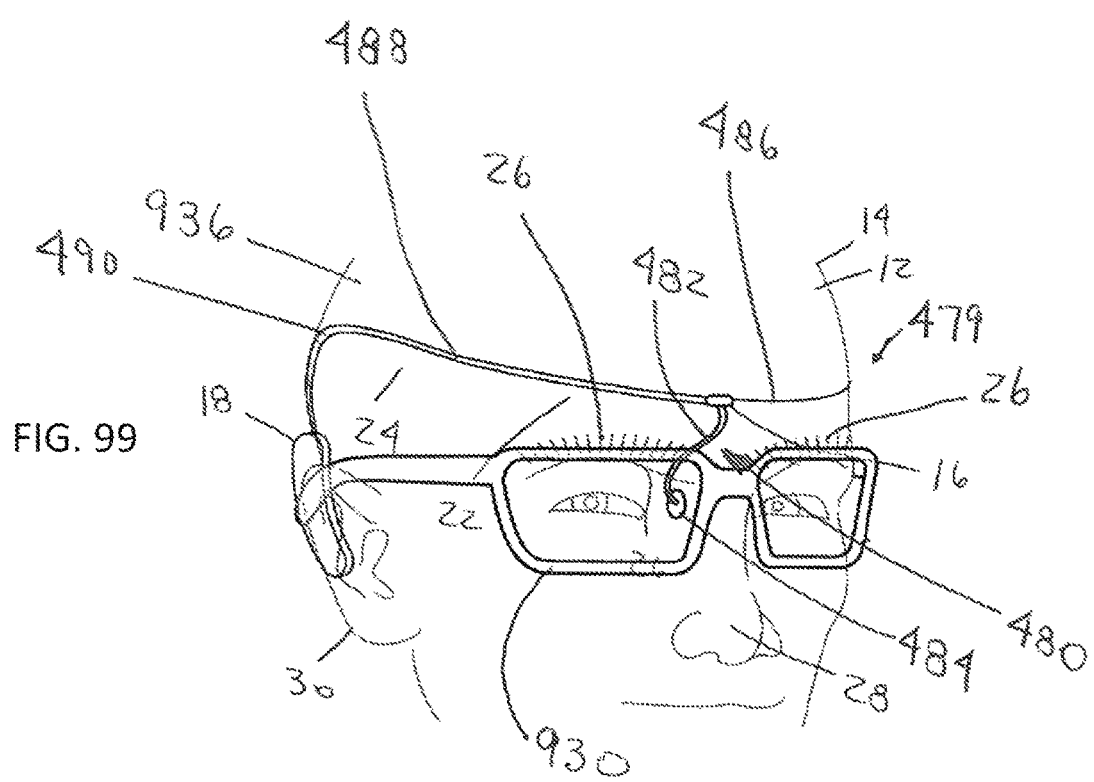
FIG. 99 shows a view of the embodiment of FIG. 60 used at the same time as a pair of conventional eyeglasses.

FIG. 99 shows sensing frame 479 of 60 being worn underneath conventional eyewear 930 by a user 936. Sensing frames of the present disclosure are adapted to be worn jointly with another eyewear and further adapted to have a sensing assembly to be adapted to be worn underneath the frames of conventional eyewear (eyeglasses and sunglasses are referred in the present disclosure as eyewear). Accordingly, FIG. 99 shows arm 482 of sensor assembly 480 extending under an upper portion 932 of a front frame 934 of conventional eyewear 930, including sensor 484 being positioned under eyebrow 26.

Figure 100:
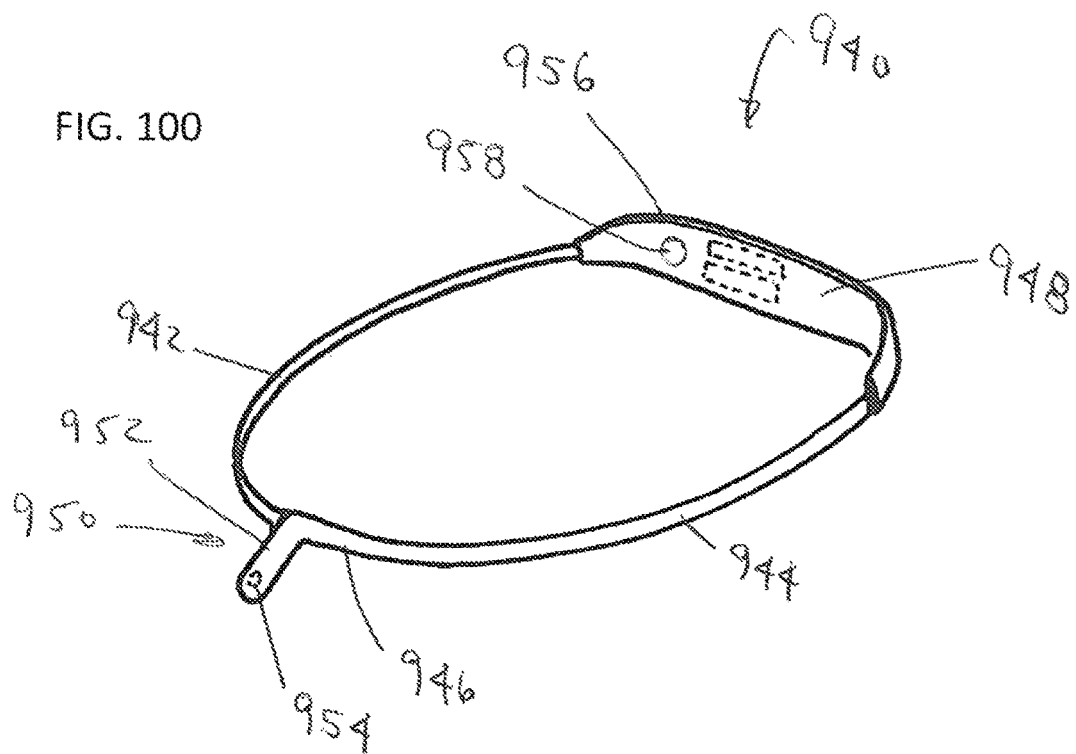
FIG. 100 shows a view of a sixty-ninth apparatus in accordance with an exemplary embodiment of the present disclosure.

FIG. 100 shows a sensing frame 940 configured as a band to be worn around the head or around a circular body portion or object, and referred to herein as a "sensing band." Sensing band 940 includes four portions: a right side portion 942, a left side portion 944, a front portion 946, and a back portion 948. Front portion 946 includes a sensing assembly 950 having an arm 952 and a sensor 954, which is electrically connected by wires (not shown) located in side portions 942 and 944 to back portion 948. Back portion 948 includes hardware 956 and a power source 958, said hardware 950 including an LED, a transmitter, a processor, non-transitory memory, a speaker, and a microphone.

Figure 101:
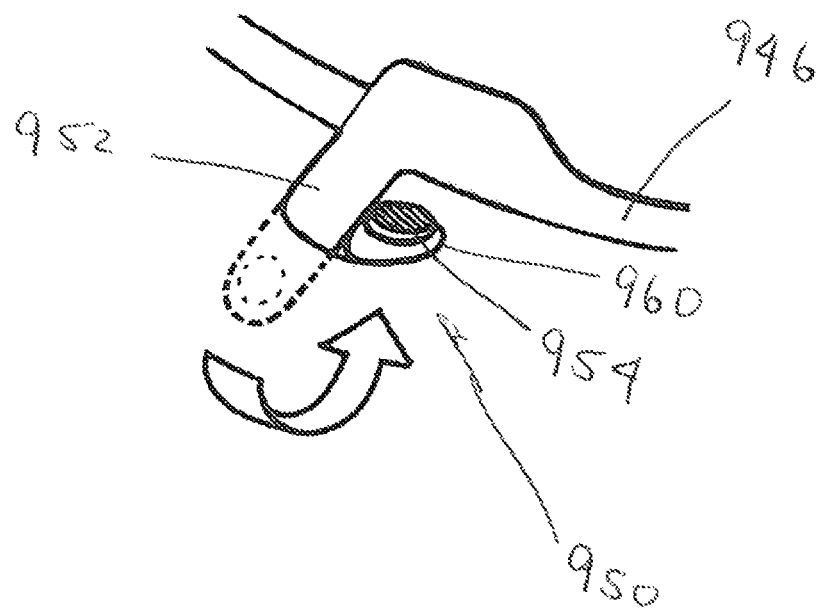
FIG. 101 shows a view of a portion of the sixty-ninth apparatus of FIG. 100.

FIG. 101 shows a view of sensor assembly 950 of FIG. 100. Sensor 954 is positioned at a terminal or end portion 960 of arm 954, which is configured to be bendable, adjustable, or positionable to position sensor 954 on or adjacent to ABTT terminus 188.

Figure 102:
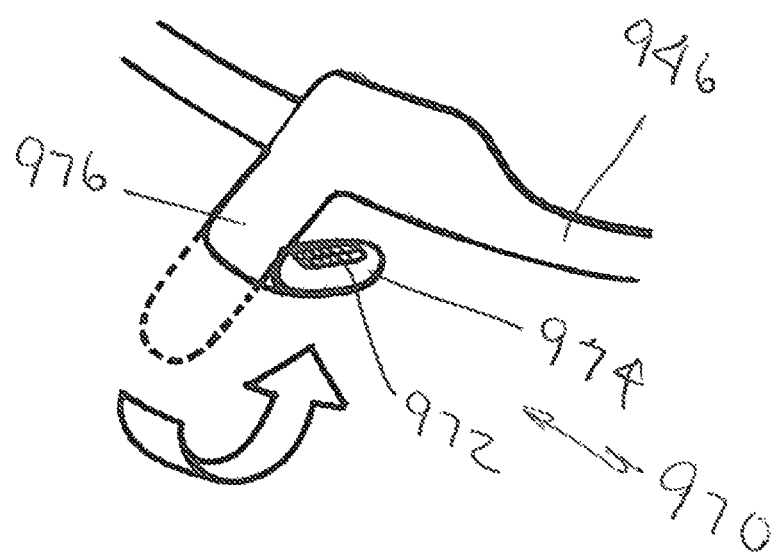
FIG. 102 shows a view of a seventieth apparatus in accordance with an exemplary embodiment of the present disclosure.

FIG. 102 shows an alternative embodiment sensor assembly 970, which includes a sensor array 972 positioned at a terminal, distal, or end portion 974 of a bendable, adjustable, or positionable arm 976.

Figure 103:
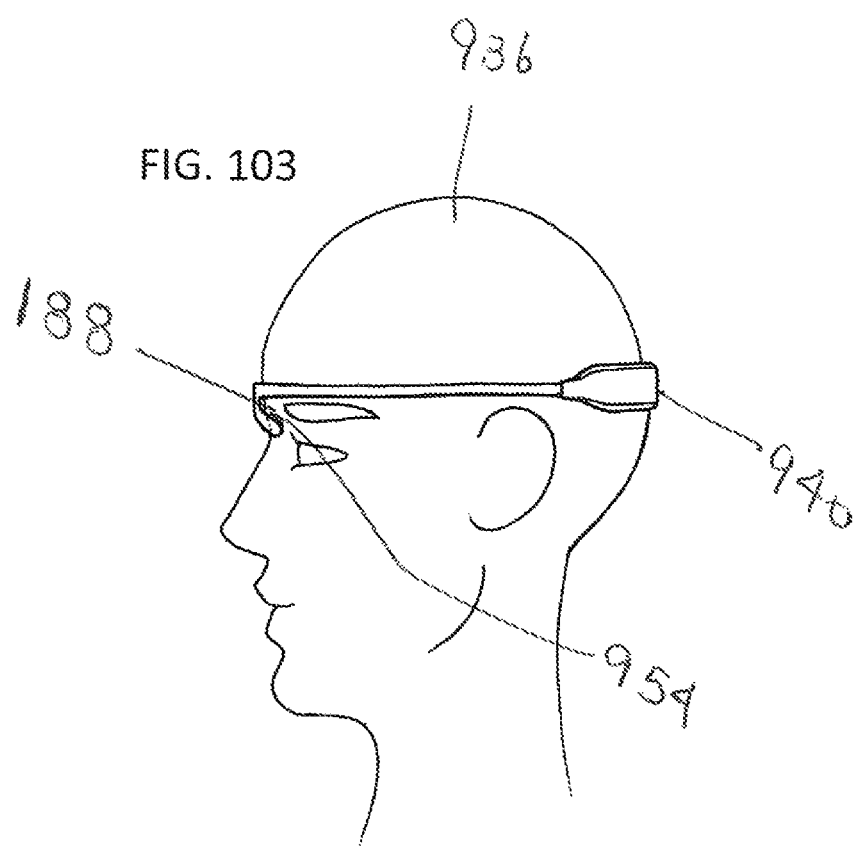
FIG. 103 shows the sixty-ninth apparatus of FIG. 100 positioned on a user in accordance with an exemplary embodiment of the present disclosure.

FIG. 103 shows sensing band 940 being worn by user 936 with sensor 954 being positioned on or adjacent to ABTT terminus 188.

Figure 104:
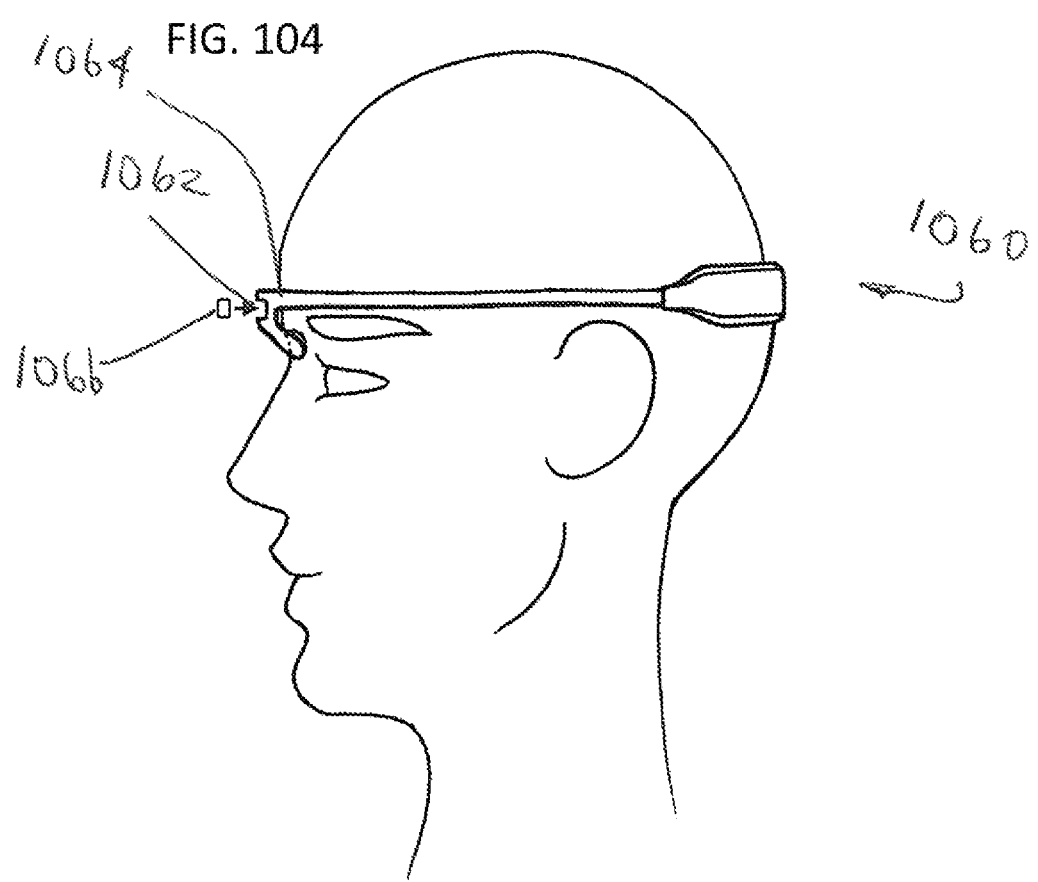
FIG. 104 shows a view of a seventy-first apparatus in accordance with an exemplary embodiment of the present disclosure.
Figure 104A:
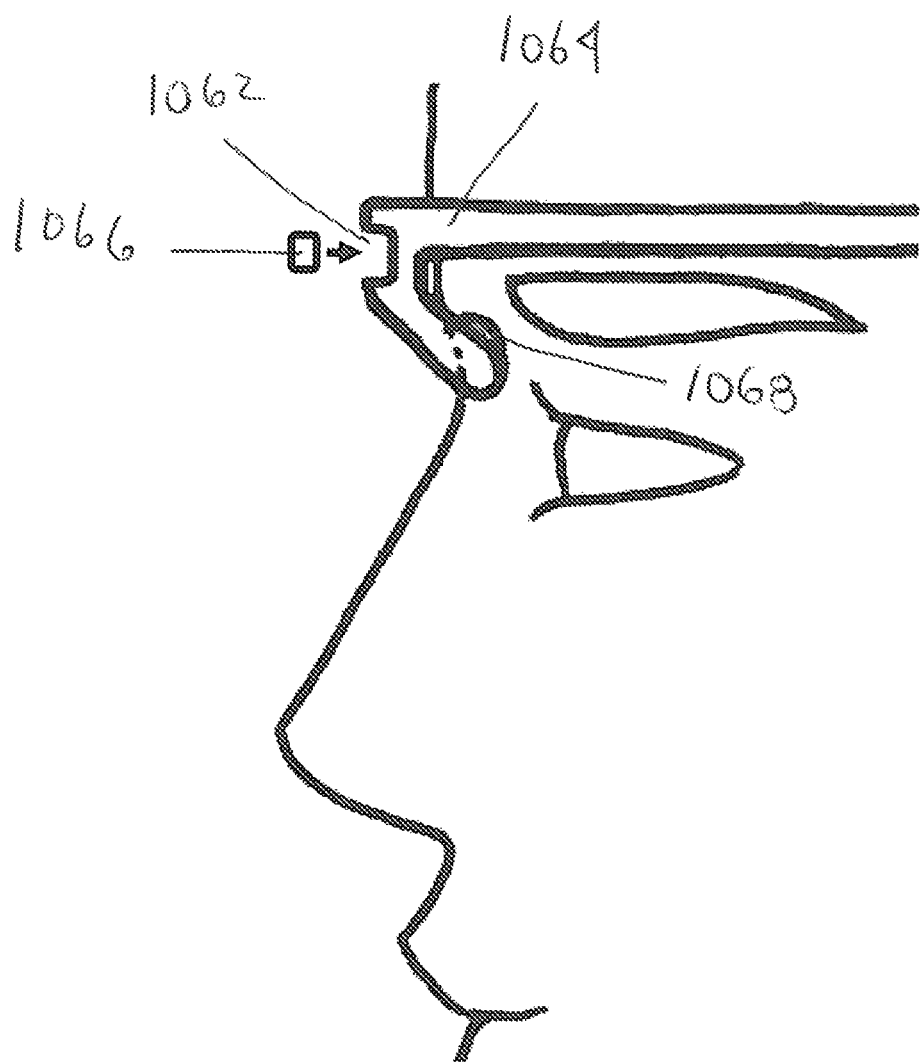
FIG. 104A shows a view of a portion of the seventy-first apparatus of FIG. 104.

FIG. 104 shows a sensing band, indicated generally at 1060, in accordance with an exemplary embodiment of the present disclosure. Sensing band 1060 includes a recess area 1062 in a front portion 1064 of sensing band 1060. Sensing band 1060 also includes a sensor 1068. Recess area 1062 being adapted to receive a frame portion 1066 of conventional eyewear. FIG. 104A shows a magnified view of recess area 1062.

FIG. 104B shows a view a portion of a sensing eyewear, indicated generally at 1080, in accordance with an exemplary embodiment of the present disclosure. Eyewear 1080 includes an arm 1082 which includes a relatively thin portion 1084, with a frame 1086 of conventional eyewear engaged into thin portion 1084.

Figure 105:
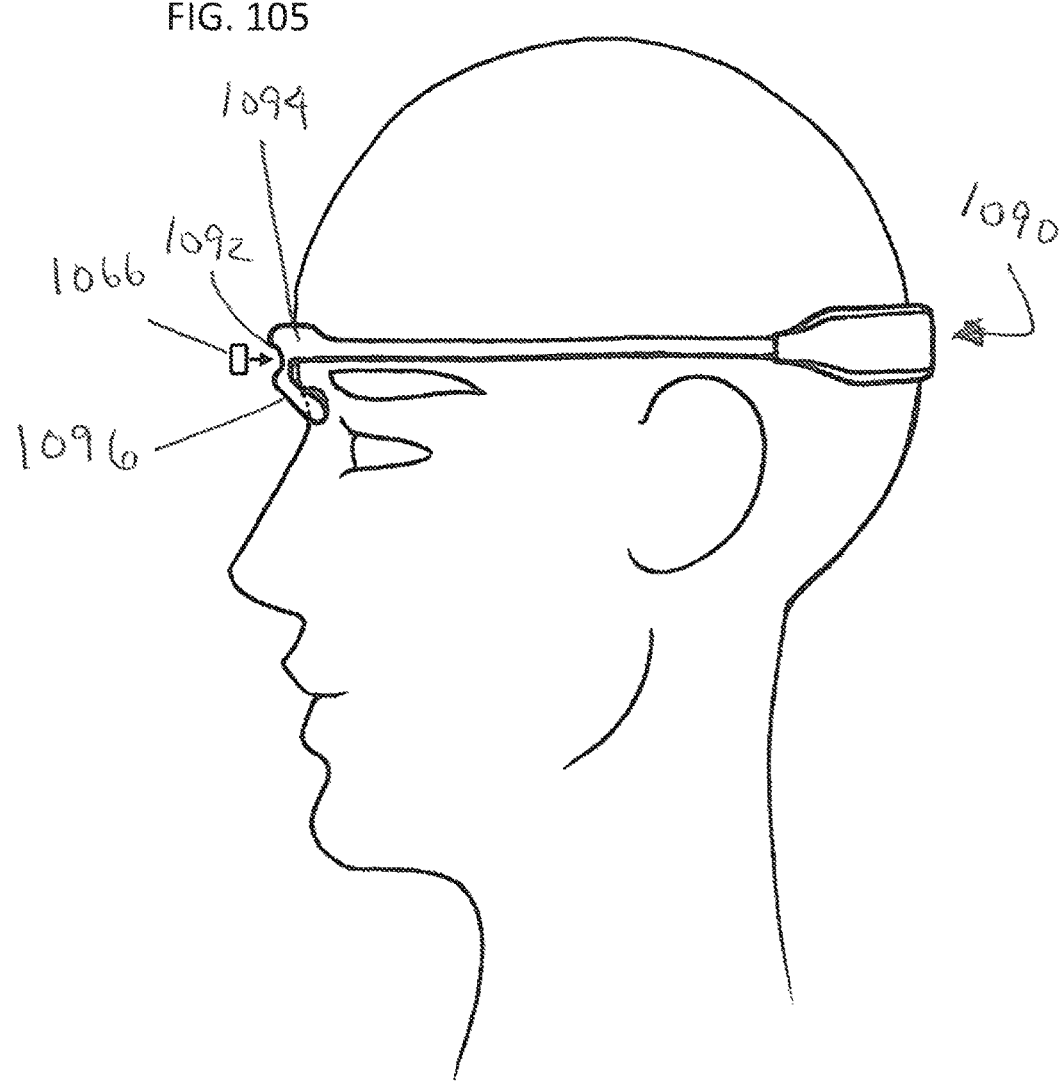
FIG. 105 shows a view of a seventy-third apparatus in accordance with an exemplary embodiment of the present disclosure.
Figure 105A:
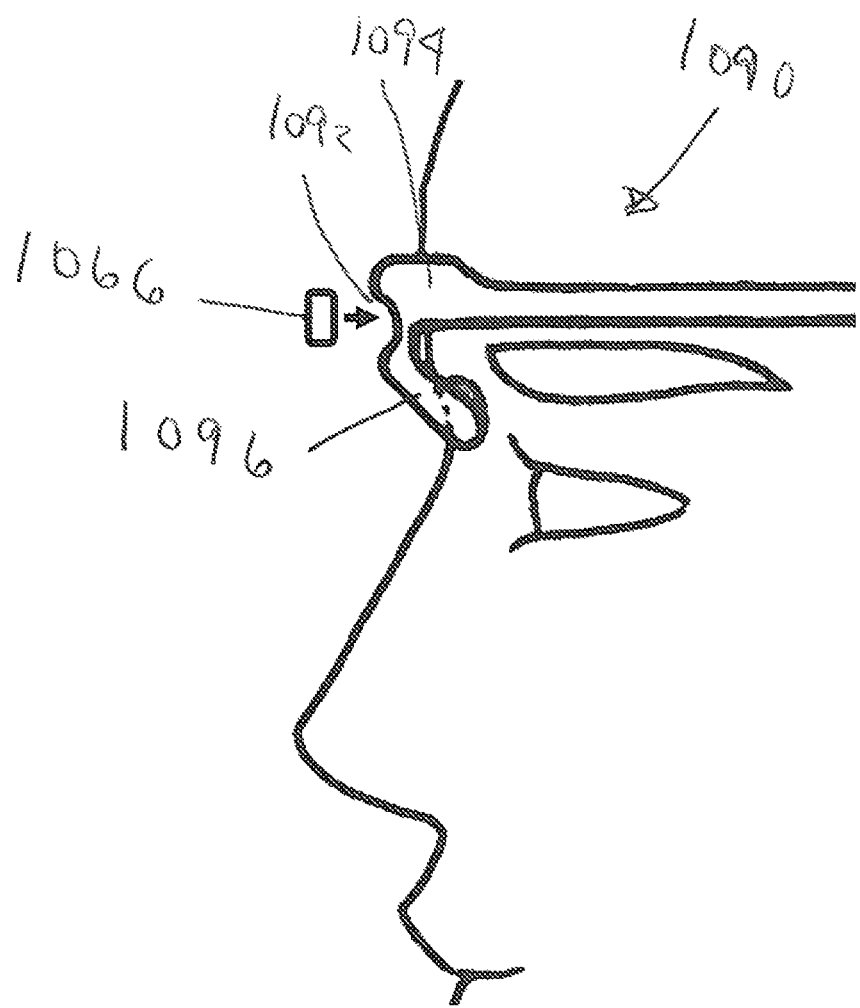
FIG. 105A shows a view of a portion of the seventy-third apparatus of FIG. 105.

FIG. 105 shows a view of a sensing band, indicated generally at 1090, in accordance with an exemplary embodiment of the present disclosure. Sensing band 1090 includes a recess area 1092 in a front portion 1094 of sensing band 1090 created by bending of a bendable arm 1096, said recess area 1092 being adapted to receive frame portion 1066 of conventional eyewear. FIG. 105A shows a magnified view of recess area 1092.

Figure 105B:
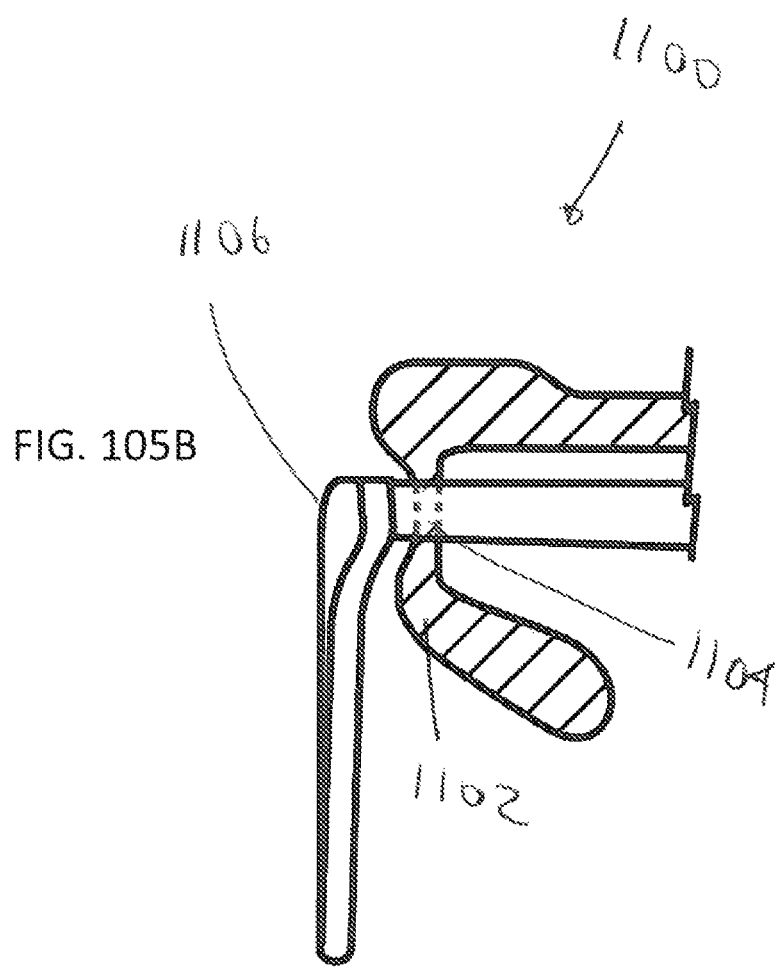
FIG. 105B shows a view of a seventy-fourth apparatus in accordance with an exemplary embodiment of the present disclosure.

FIG. 105B shows a view a portion of a sensing eyewear, indicated generally at 1100, in accordance with an exemplary embodiment of the present disclosure. Eyewear 1100 includes a bendable arm 1102 which includes a relatively thin portion 1104, with a frame 1106 of conventional eyewear engaged into thin portion 1104.

Figure 106:
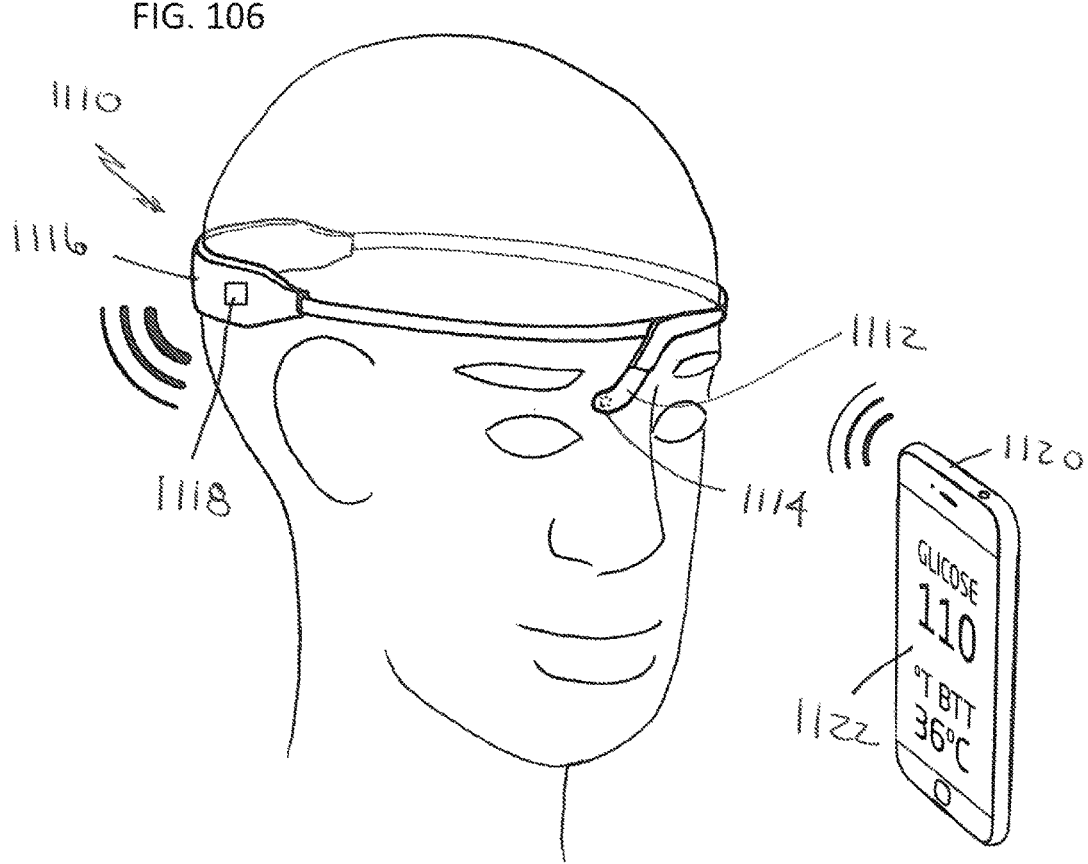
FIG. 106 shows a view of a seventy-fifth apparatus in accordance with an exemplary embodiment of the present disclosure.
Figure 107:
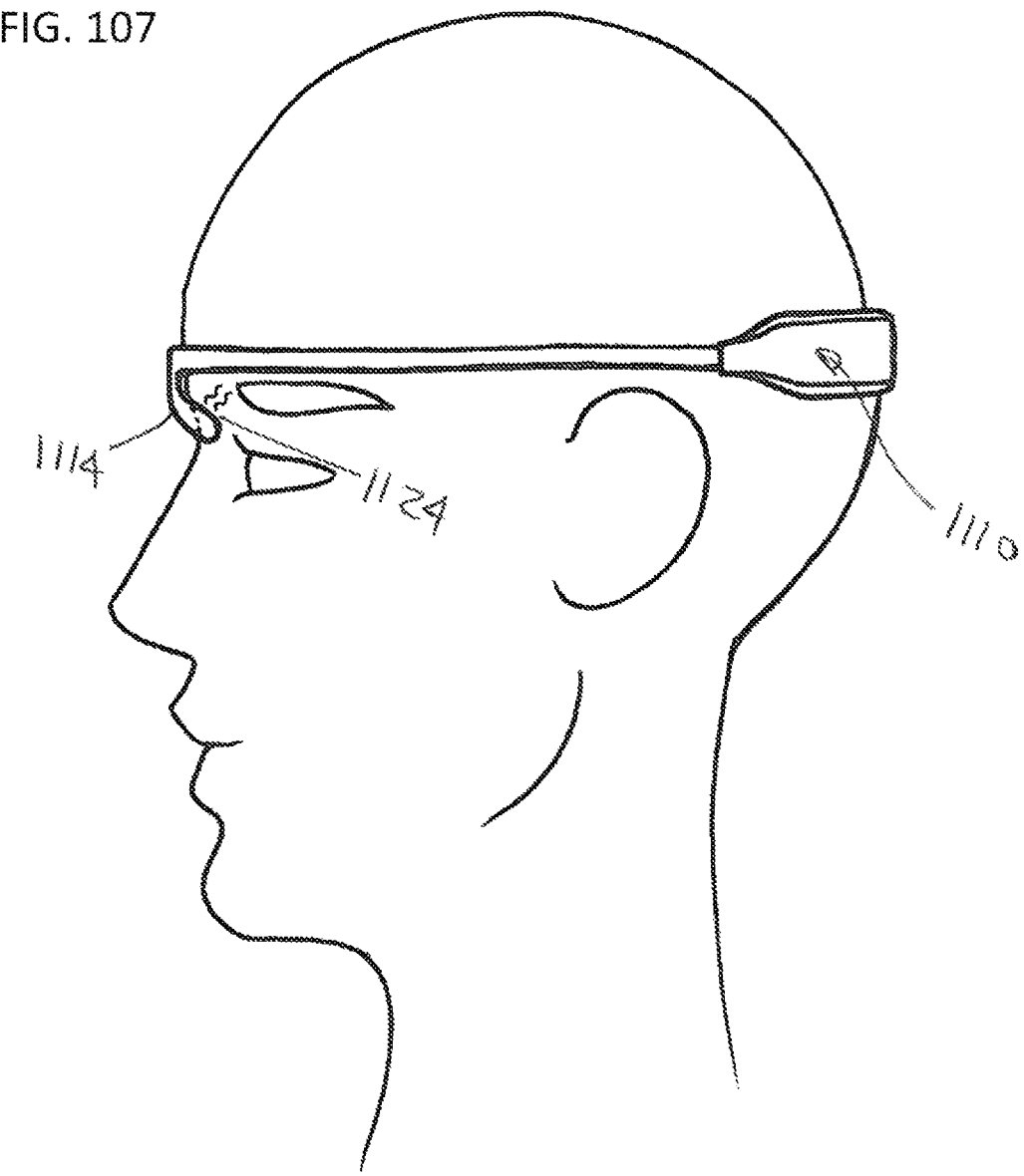
FIG. 107 shows another view of the seventy-fifth apparatus of FIG. 106.
Figure 108:
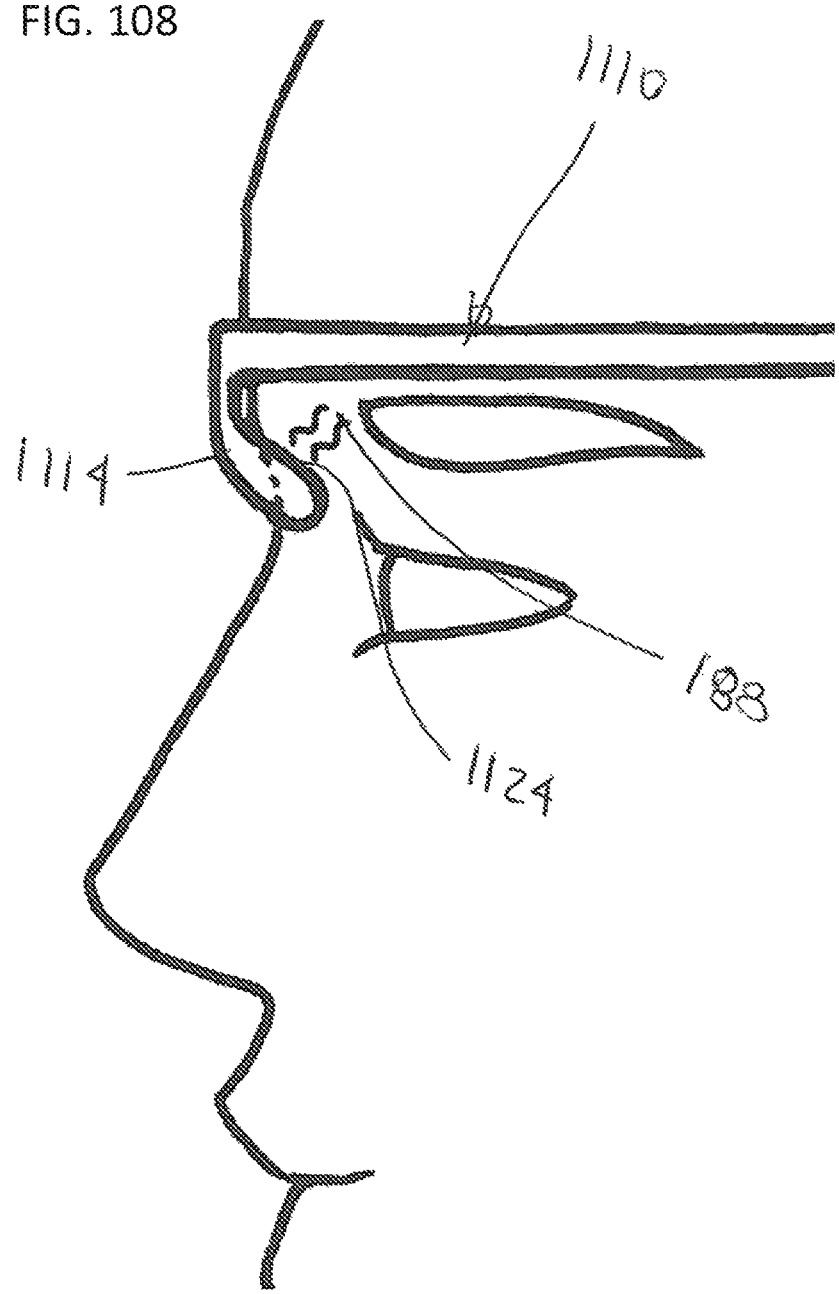
FIG. 108 shows another view of the seventy-fifth apparatus of FIG. 106.

FIGS. 106-108 show views of a sensing band, indicated generally at 1110, in accordance with an exemplary embodiment of the present disclosure. Sensing band 1110 includes a bendable arm 1112 and a dual sensor head 1114. Sensor head 1114 being adapted for infrared detection for measurement of glucose and of temperature. A back portion 1116 of sensing band 1110 has a wireless device 1118 and other electronics adapted to transmit a signal to a remote device 1120, illustrated herein as a cell phone having a display 1122 showing glucose level and temperature level. As shown in FIGS. 107 and 108, dual sensor head 1114 includes sensors 1124 configured to receive to receive radiation from ABTT terminus 188. Although FIGS. 107 and 108 show sensor 1124 receiving radiation from ABTT terminus 188, it should be understood that sensor 1124 of sensing band 1110 is adapted to receive radiation from any other body part or object.

Figure 109:
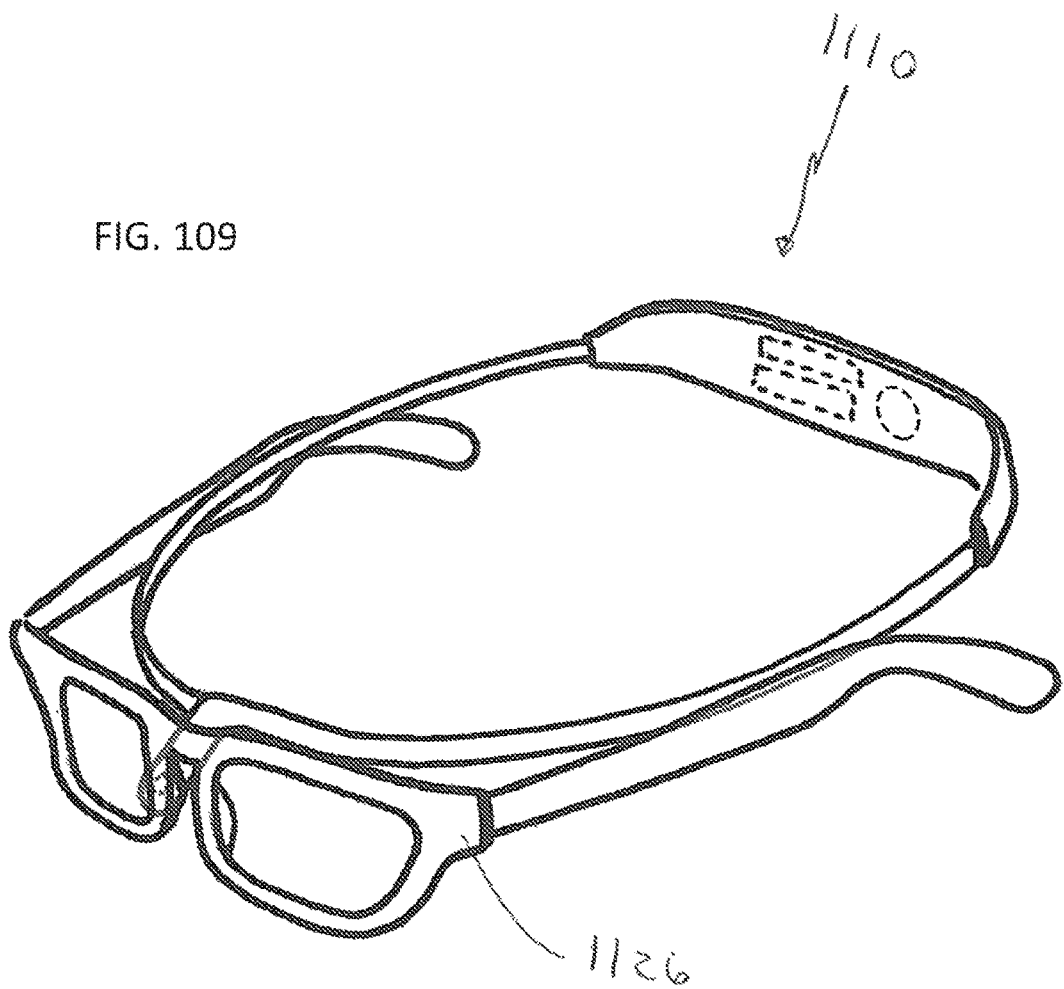
FIG. 109 shows a view of a seventy-sixth apparatus in accordance with an exemplary embodiment of the present disclosure.
Figure 110:
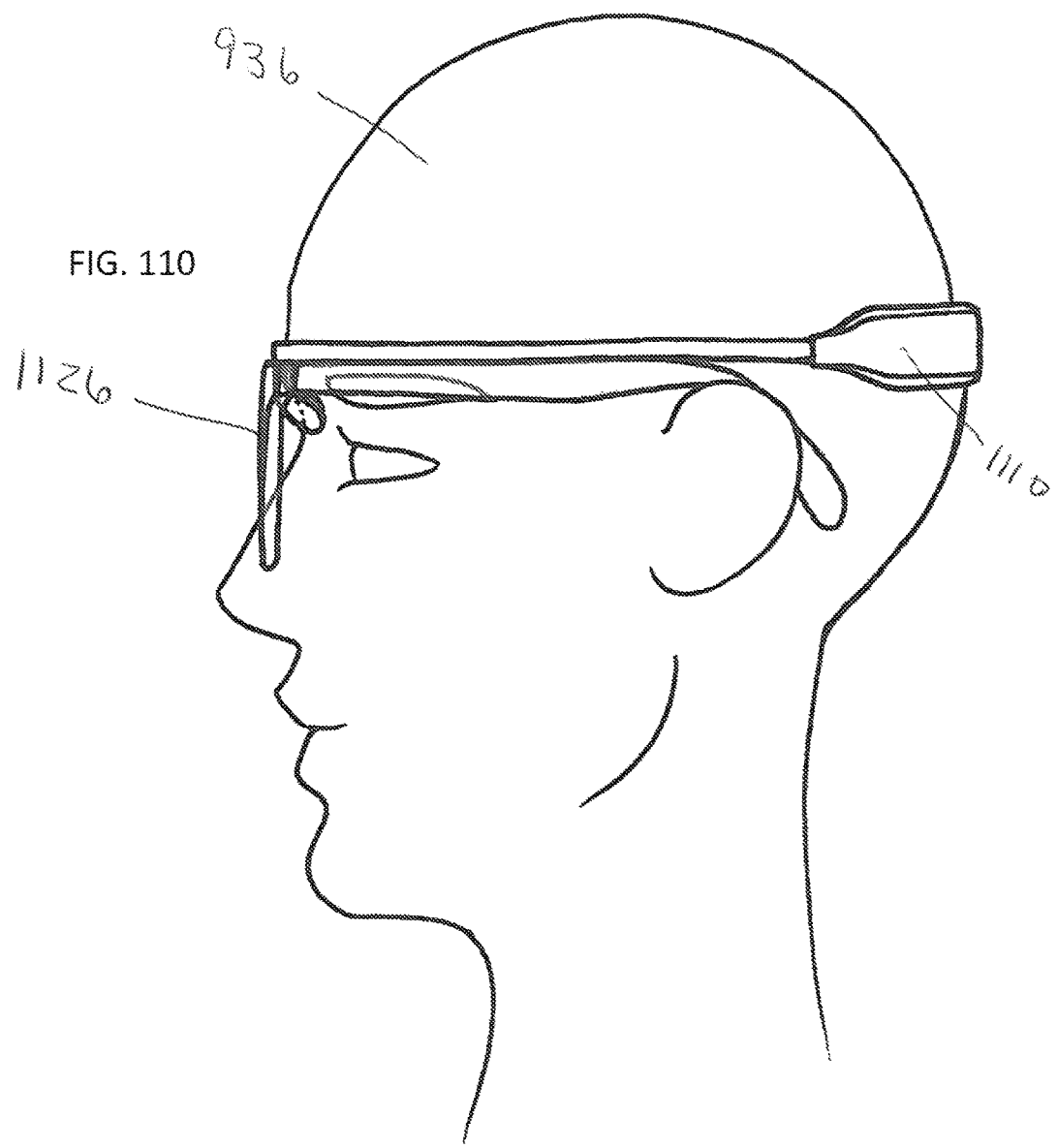
FIG. 110 shows another view of the seventy-sixth apparatus of FIG. 109.

FIGS. 109 and 110 show views of a configuration that includes sensing band 1110 in use with conventional eyewear 1126, thereby enabling a user to use conventional eyewear while simultaneously wearing sensing frames or sensing band 1110 of the current disclosure. FIG. 110 shows the configuration of FIG. 109 worn by user 936. FIG. 110A shows details of engagement of sensing frame or sensing band 1110 and conventional eyewear 1126. A side portion 1128 of sensing band 1110 is located just above and adjacent to a temple 1130 of conventional eyewear 1126. A conventional front frame 1132 of conventional eyewear 1126 includes lens 1134, conventional front frame 1132 overlapping sensing band 1110, and an upper portion 1136 of conventional front frame 1132 engaging into a recess area 1138 of sensing band 1110, with sensors 1124 located under temple 1130 of conventional eyewear 1126, sensors 1124 being positioned behind lens 1134 and on or adjacent to ABTT terminus 188 next to eyebrow 26.

Figure 111:
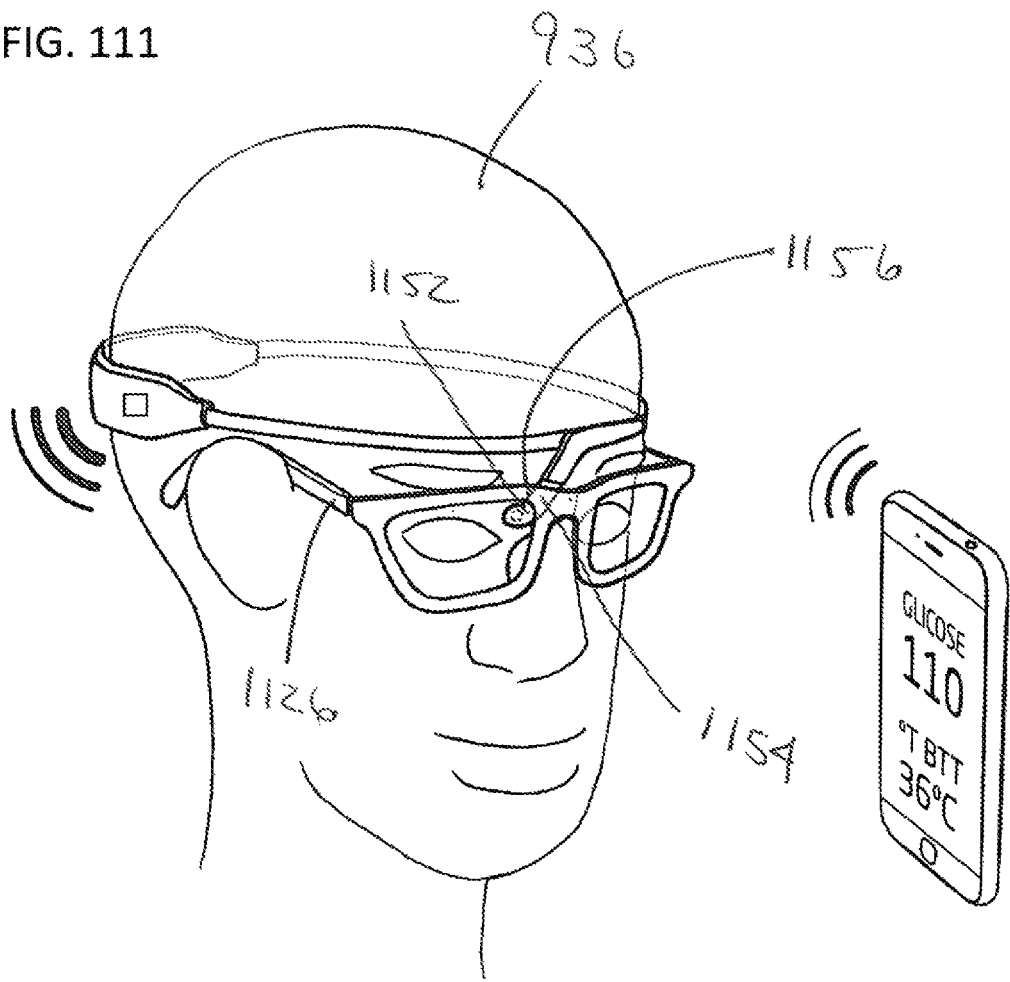
FIG. 111 shows a view of a seventy-seventh apparatus in accordance with an exemplary embodiment of the present disclosure.

FIG. 111 shows a sensing band, indicated generally at 1150, in accordance with an exemplary embodiment of the present disclosure. Sensing band 1150 includes features similar to sensing band 1110 shown in FIG. 106, and is labelled similarly where appropriate. User 936 is shown wearing sensing band 1150 jointly with conventional eyewear 1126. Sensing band 1150 includes an arm 1152 having an engaging area 1154 adapted to receive a frame 1156 of conventional eyewear 1126.

Figure 112:
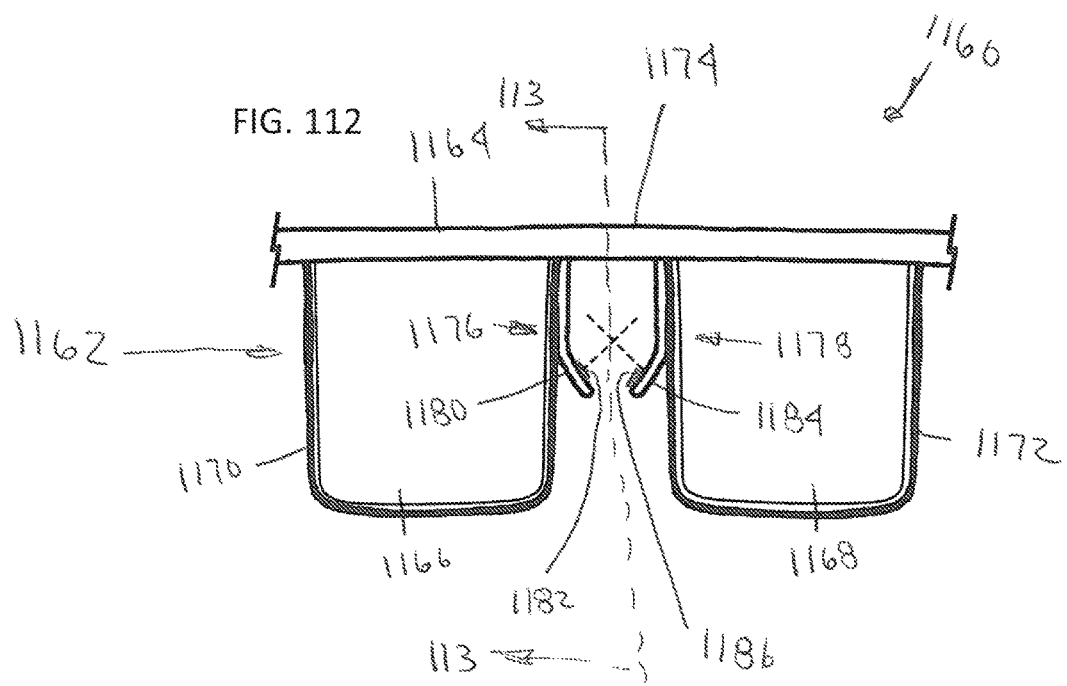
FIG. 112 shows a view of a seventy-eighth apparatus in accordance with an exemplary embodiment of the present disclosure.
Figure 113:
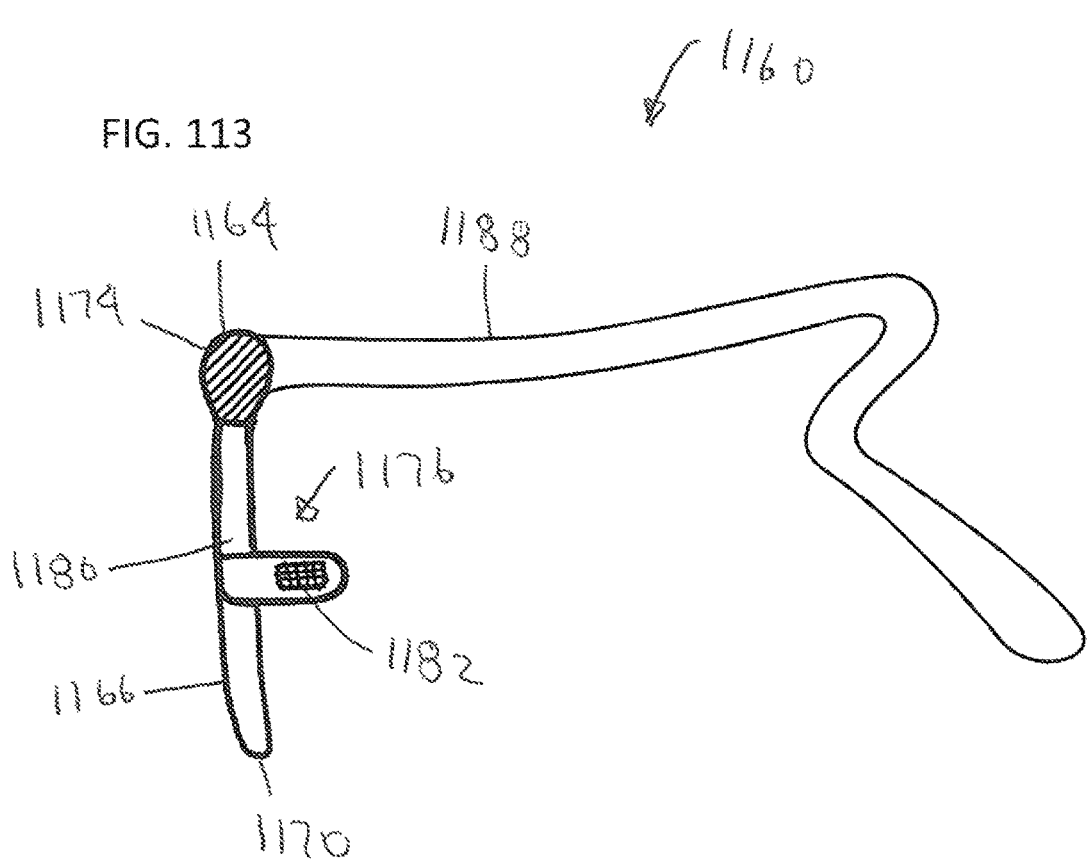
Figure 114:
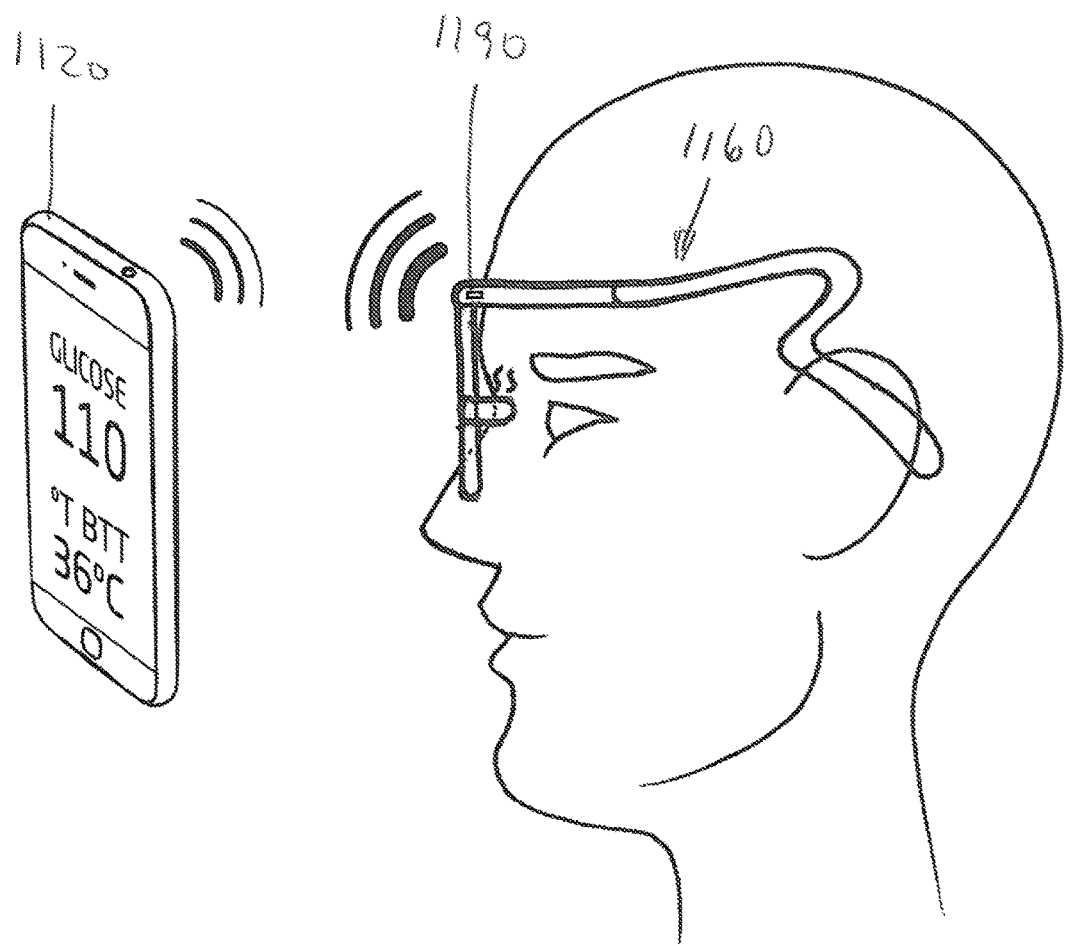

FIGS. 112-114 show views of a sensing eyewear, indicated generally at 1160, in accordance with an exemplary embodiment of the present disclosure. Sensing eyewear 1160 includes a front portion 1162. Front portion 1162 includes an upper frame 1164, a right oversized lens 1166, a left oversized lens 1168, a right lens rim 1170, a left lens rim 1172, an interconnection central portion 1174 connecting right lens rim 1170 and left lens rim 1172, a right sensor assembly 1176, and a left sensor assembly 1178. Right sensor assembly 1176 includes a right arm 1180 and a right sensor 1182. Left sensor assembly 1178 includes a left arm 1184 and left sensor 1186. As shown in FIG. 113, sensing eyewear 1160 also includes a right temple 1188 (and a left temple, which is not shown). As shown in FIG. 114, sensing eyewear 1160 can further include a wireless device 1190 configured for wireless signal communication with separate or remote device 1120.

Figure 115:
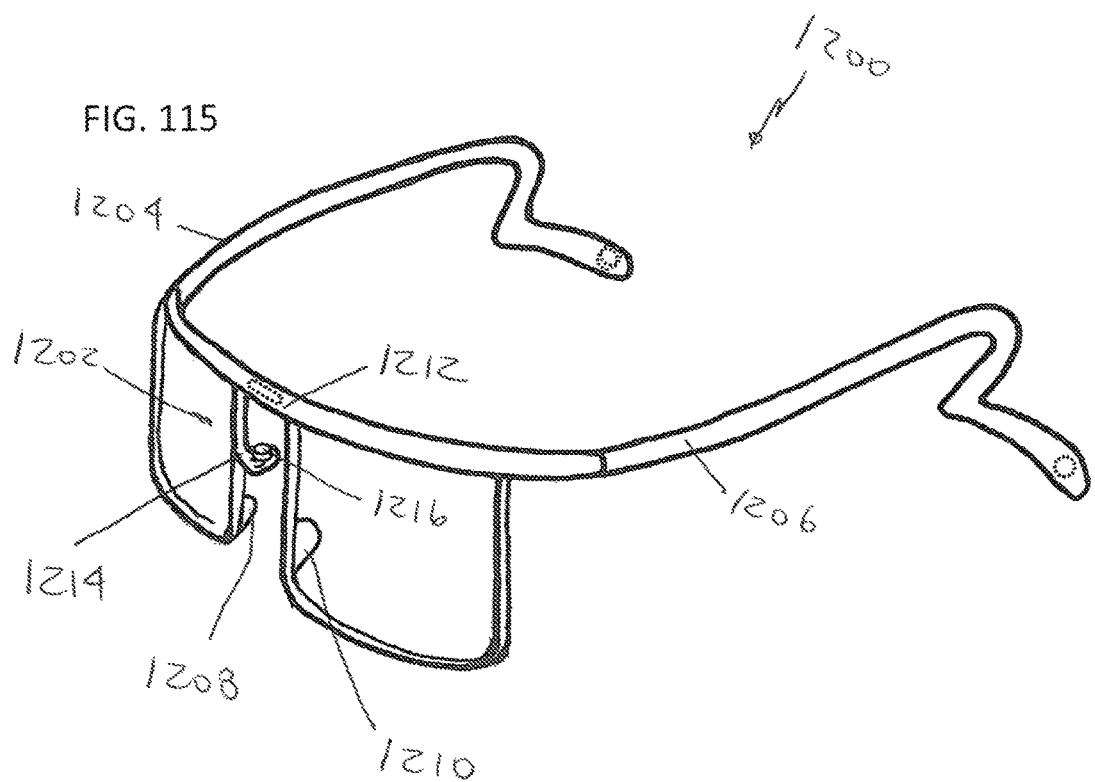

FIG. 115 shows a perspective view of a sensing frame, indicated generally at 1200, in accordance with an exemplary embodiment of the present disclosure. Sensing frame 1200 includes at least one sensor assembly 1202, shown as a right sensor assembly, a right temple 1204, a left temple 1206, and a right nose pad 1208 and a left nose pad 1210 that are located at a spaced distance from a central portion 1212 of sensing frame 1200 that would be over the bridge of the nose by virtue of the increased size of the right lens rim 1170 and left lens rim 1172. Right sensor assembly 1202 is located just above right nose pad 1208 and includes a supporting portion 1214 connected to right lens rim 1170 and a sensor 1216.

Figure 116:
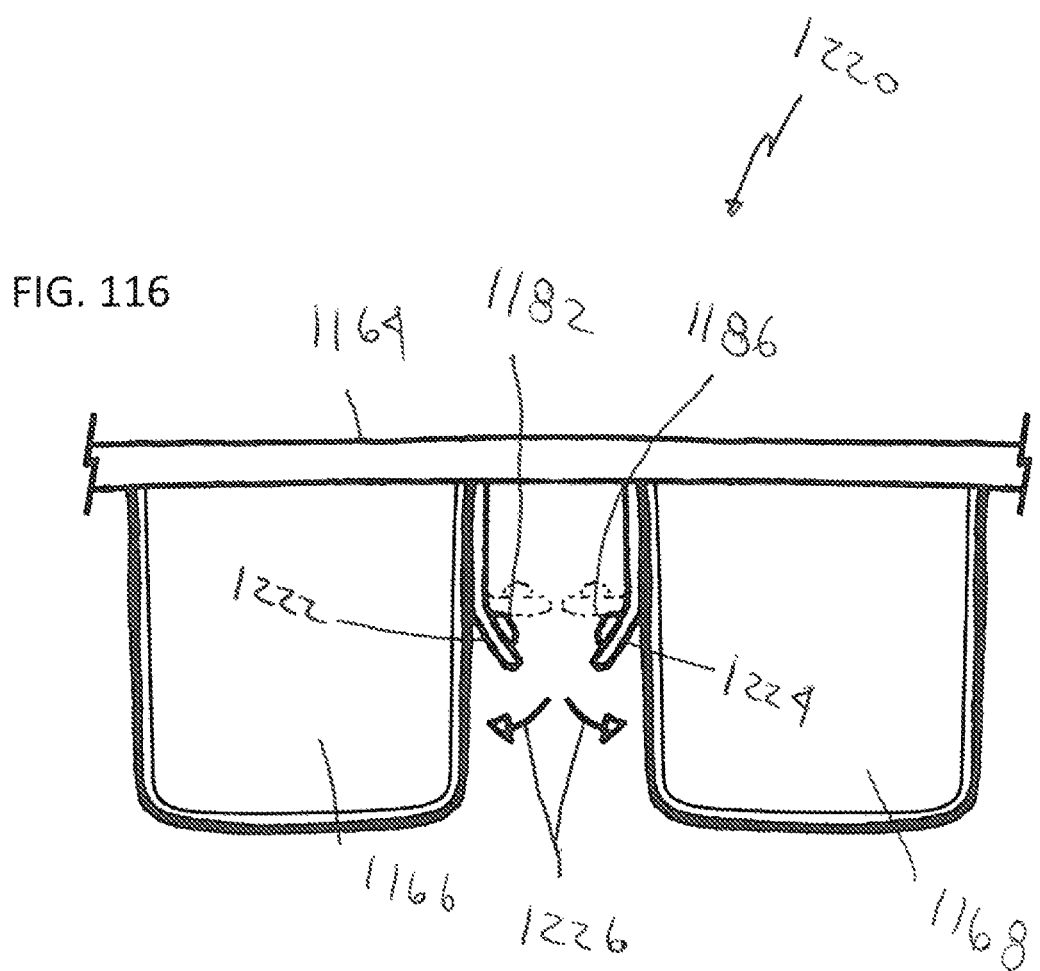

FIG. 116 shows a view of a sensing eyewear, indicated generally at 1220, in accordance with an exemplary embodiment of the present disclosure. Sensing eyewear 1220 includes some similarities to sensing eyewear 1160 shown in FIG. 112, and is similarly labelled where appropriate. Sensing eyewear 1220 includes bendable arms 1222 and 1224 with motion of bendable arms 1222 and 1224 shown by arrows 1226 for aligning right sensor 1182 and left sensor 1186 with ABTT terminus 188.

Figure 117:
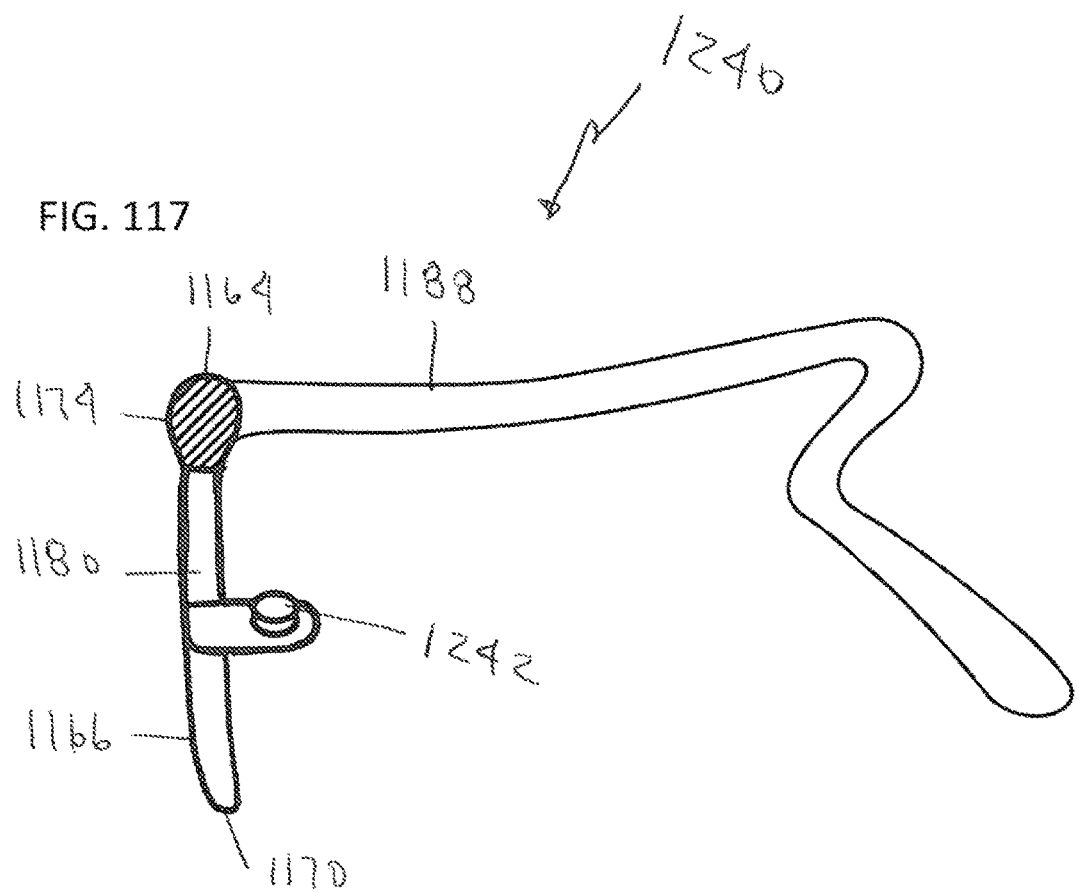
Figure 118:
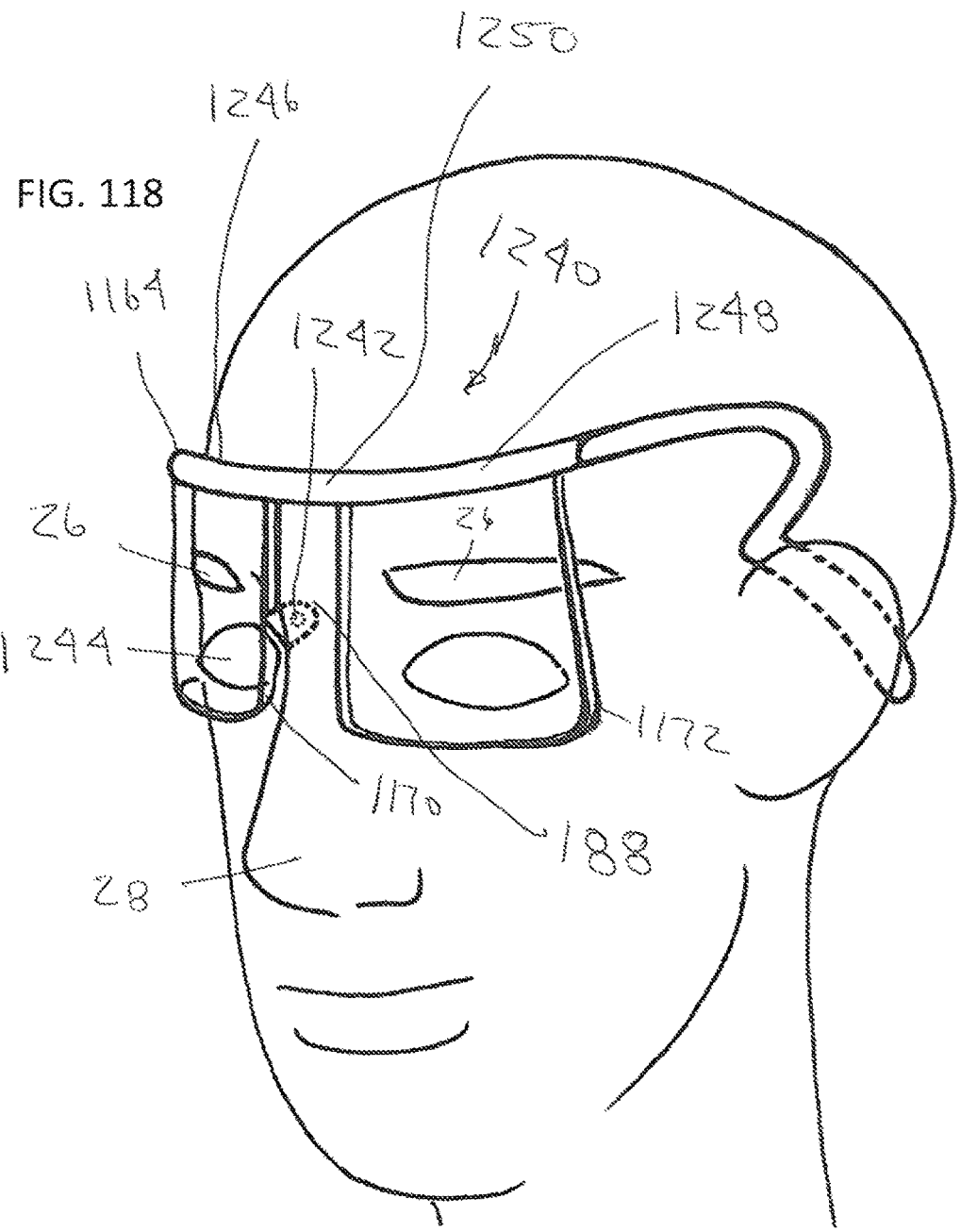

FIGS. 117 and 118 show views of a sensing eyewear, indicated generally at 1240, in accordance with an exemplary embodiment of the present disclosure. Sensing eyewear 1240 includes some similarities to sensing eyewear 1160 shown in FIG. 112, and is similarly labelled where appropriate. Sensing eyewear 1240 includes a single sensor 1242 in place of sensor array 1182. As shown in FIG. 118, sensing eyewear 1240 includes temple 1188, upper frame 1164, right lens rim 1170, and left lens rim 1172. Right lens rim 1170 has sensor 1242, which is positioned at, on, adjacent, alongside, or near ABTT terminus 188 between an eye 1244 and eyebrow 26, and adjacent to nose 28. Upper frame 1164 includes three portions: a right side portion 1246, left side portion 1248, and central portion 1250.

It should be understood that any embodiment or recess areas described for a sensing band are applicable to any eyewear or sensing eyewear of the present disclosure.

For the sake of brevity embodiments were shown as exemplary devices. Any part of any embodiment can be used in combination to create a single embodiment, and any part of any embodiment can be used as a replacement or addition to another embodiment, and all resultant embodiments are within the scope of the present disclosure.

While various embodiments of the disclosure have been shown and described, it should be understood that these embodiments are not limited thereto. The embodiments can be changed, modified, and further applied by those skilled in the art. Therefore, these embodiments are not limited to the detail shown and described previously, but also include all such changes and modifications.

I claim:

1. An apparatus supported by a human head, comprising:
   a self-supporting curvilinear wire including a first free end, a second free end, and an upper frame extending from the first end to the second end, the first free end and the second free end being spaced apart from each other so that the first end of the curvilinear wire is configured to be supported on the head adjacent to a first ear and the second end of the curvilinear wire is configured to be supported on the head adjacent to a second ear, the first ear being located opposite to the second ear on opposite sides of the head,
   the self-supporting curvilinear wire retaining a predetermined shape and extending less that a complete circumference of the head so that the first end and the second end grip opposite sides of the head by pressure to retain the upper frame in position,
   the upper frame is configured to grip at least temples at opposite sides of the head to support the upper frame on a forehead of the head at a location above a pair of eyebrows, and
   at least one device supported by the apparatus, the at least one device being positioned at one of the first end and the second end, with the at least one device being configured to be positioned behind and adjacent to one of the first ear and the second ear.

2. The apparatus of claim 1, wherein at least one of the first end and the second end connects to the at least one device.

3. The apparatus of claim 1, wherein the apparatus includes a temperature sensor supported by the upper frame.

4. The apparatus of claim 3, wherein the temperature sensor is positioned a spaced distance from the upper frame.

5. The apparatus of claim 1, wherein the device is one of an electroencephalograph, a spectral monitor, and a bispectral index (BIS) monitor.

6. The apparatus of claim 1, further comprising a movable mechanism adjustable to modify a position of the apparatus on the head.

7. The apparatus of claim 6, wherein the device is a temperature sensor and the adjustment of the movable mechanism changes the position of the temperature sensor with respect to an Abreu brain thermal tunnel (ABTT) location when the apparatus is positioned on the head.

8. The apparatus of claim 1, further comprising a transmitter configured to communicate with a separate electronic device and configured to at least receive a signal from the device or transmit a signal to the device.

9. The apparatus of claim 1, wherein one of the first end and the second end is configured to include a wire terminating in a connector, the wire being electrically connected to the device.

10. The apparatus of claim 1, wherein when the apparatus is positioned on the human head, a distance from a tip of an ear of the head to the upper frame is less than 35 mm.

11. The apparatus of claim 1, wherein when the apparatus is positioned on the human head the curvilinear wire extends in a downward curve from a location above the eyebrows to connect to the at least one device.

12. The apparatus of claim 1, wherein when the apparatus is positioned on the human head the curvilinear wire includes a double loop positioned on each side of the human head.

13. The apparatus of claim 1, wherein the first end and the second end of the curvilinear wire extend downward from the upper frame to extend down behind the first ear and the second ear.

* * * * *